US011737436B2

(12) United States Patent
Koukidou et al.

(10) Patent No.: US 11,737,436 B2
(45) Date of Patent: Aug. 29, 2023

(54) GENE EXPRESSION SYSTEM

(71) Applicant: Oxitec Limited, Abingdon (GB)

(72) Inventors: Martha Koukidou, Abingdon (GB); Luke Alphey, Abingdon (GB); Simon Warner, Abingdon (GB)

(73) Assignee: Oxitec Limited, Abingdon (GB)

( * ) Notice: Subject to any disclaimer, the term of this patent is extended or adjusted under 35 U.S.C. 154(b) by 370 days.

(21) Appl. No.: 16/997,416

(22) Filed: Aug. 19, 2020

(65) Prior Publication Data

US 2021/0137083 A1 May 13, 2021

Related U.S. Application Data

(63) Continuation of application No. 15/313,922, filed as application No. PCT/GB2015/051633 on Jun. 4, 2015, now abandoned.

(51) Int. Cl.

*C12N 15/85* (2006.01)
*A01K 67/033* (2006.01)
*C12Q 1/6888* (2018.01)

(52) U.S. Cl.

CPC ...... *A01K 67/0339* (2013.01); *C12N 15/8509* (2013.01); *C12Q 1/6888* (2013.01); *A01K 2217/072* (2013.01); *A01K 2217/15* (2013.01); *A01K 2217/203* (2013.01); *A01K 2217/206* (2013.01); *A01K 2217/30* (2013.01); *A01K 2227/706* (2013.01); *A01K 2267/02* (2013.01); *C12N 2800/90* (2013.01); *C12N 2830/006* (2013.01); *C12N 2830/008* (2013.01); *C12N 2830/15* (2013.01); *C12N 2840/007* (2013.01); *C12N 2840/44* (2013.01); *C12N 2840/75* (2013.01); *C12N 2999/007* (2013.01); *C12Q 2600/158* (2013.01)

(58) Field of Classification Search

None
See application file for complete search history.

(56) References Cited

U.S. PATENT DOCUMENTS 5,254,801 A 10/1993 Dotson et al.
5,278,057 A 1/1994 Jorgensen
5,670,353 A 9/1997 Ahlquist et al.
5,674,747 A 10/1997 Hammock et al.
5,773,697 A 6/1998 Tomes et al.
5,851,796 A 12/1998 Schatz
5,977,441 A 11/1999 Oliver et al.
6,200,800 B1 3/2001 Choulika et al.
6,235,278 B1 5/2001 Miller et al.
6,338,040 B1 1/2002 Buman et al.
6,962,810 B2 11/2005 Fraser et al.
7,998,475 B2 8/2011 Alphey
8,124,404 B2 2/2012 Alphey
8,704,041 B2 4/2014 Gordon-Kamm et al.
9,121,036 B2 9/2015 Alphey
9,125,388 B2 9/2015 Alphey et al.
9,133,477 B2 9/2015 Alphey
9,487,801 B2 11/2016 Alphey
9,970,025 B2 5/2018 Alphey
10,059,961 B2 8/2018 Alphey
10,844,402 B2 11/2020 Alphey
10,941,416 B2 3/2021 Alphey
2003/0150007 A1 8/2003 Savakis et al.
2003/0213005 A1 11/2003 Alphey et al.
2004/0082032 A1 4/2004 Bovi et al.
2005/0221430 A1 10/2005 Prentice
2006/0212949 A1 9/2006 Alphey
2006/0242717 A1 10/2006 Alphey
2006/0275276 A1 12/2006 Alphey
2007/0056051 A1 3/2007 Alphey
2008/0115233 A1 5/2008 Alphey et al.
2009/0170793 A1 7/2009 Gaur
2009/0183269 A1 7/2009 Alphey
2013/0298266 A1 11/2013 Alphey et al.
2015/0143552 A1 5/2015 Alphey
2016/0044902 A1 2/2016 Alphey et al.
2016/0060651 A1 3/2016 Alphey
2016/0122780 A1 5/2016 Alphey
2017/0009253 A1 1/2017 Alphey
2017/0188559 A1 7/2017 Koukidou et al.
2018/0251785 A1 9/2018 Alphey
2018/0312870 A1 11/2018 Alphey
2020/0407748 A1 12/2020 Alphey et al.

(Continued)

FOREIGN PATENT DOCUMENTS

CA 2012311 C 6/2003
EP 0636310 A1 2/1995
EP 0955364 A2 11/1999

(Continued)

OTHER PUBLICATIONS

Windbichler et al., "Targeting The X Chromosome During Spermatogenesis Induces Y Chromosome Transmission Ratio Distortion And Early Dominant Embryo Lethality In Anopheles Qarnbiae", PLOS Genetics, vol. 4, No. 12, 2008.
Wobus et al., "A New Transposable Element in Chironomus thummi", Molecular Genetics and Genomics, vol. 222, 1990, pp. 311-316.
Woltjen et al., "Piggybac Transposition Reprograms Fibroblasts to Induced Pluripotent Stem Cells", Nature, vol. 458, No. 7239, 2009, 766-770.
Wool et al., "Genetically-Induced Susceptibility to Malathion in Tribolium Castaneum Despite Selection for Resistance", Entomologia Experimentalis et Applicata, 1980, pp. 183-190.

(Continued)

*Primary Examiner* — Celine X Qian
(74) *Attorney, Agent, or Firm* — Morrison & Foerster LLP

(57) ABSTRACT

Two or more conditional, dominant, lethal gene expression systems provide high levels of penetrance in insects. Lethality is induced at an earlier stage of development and the risk of biochemical resistance is reduced, as compared to a single insect conditional, dominant, lethal gene expression system. The invention is useful for the control of insect populations.

4 Claims, 10 Drawing Sheets

Specification includes a Sequence Listing.

(56) References Cited

U.S. PATENT DOCUMENTS

| | | | |
|---|---|---|---|
| 2021/0324409 | A1 | 10/2021 | Turkle et al. |
| 2022/0098597 | A1 | 3/2022 | Joyce et al. |

FOREIGN PATENT DOCUMENTS

| | | | |
|---|---|---|---|
| EP | 3152311 | B1 | 8/2019 |
| GB | 2355459 | A | 4/2001 |
| GB | 2404382 | A | 2/2005 |
| GB | 2443186 | A | 4/2008 |
| GB | 2500113 | A | 9/2013 |
| JP | 2008-67678 | A | 3/2008 |
| WO | 1990/08830 | A1 | 8/1990 |
| WO | 1994/03619 | A2 | 2/1994 |
| WO | 1996/04393 | A2 | 2/1996 |
| WO | 1996/24605 | A1 | 8/1996 |
| WO | 1997/30162 | A1 | 8/1997 |
| WO | 1998/08960 | A1 | 3/1998 |
| WO | 1999/10488 | A1 | 3/1999 |
| WO | 2000/73510 | A1 | 12/2000 |
| WO | 2001/39599 | A2 | 6/2001 |
| WO | 2001/59088 | A2 | 8/2001 |
| WO | 2001/91802 | A1 | 12/2001 |
| WO | 2002/46444 | A2 | 6/2002 |
| WO | 2002/101061 | A2 | 12/2002 |
| WO | 2004/044150 | A2 | 5/2004 |
| WO | 2004/098278 | A1 | 11/2004 |
| WO | 2004/108933 | A1 | 12/2004 |
| WO | 2005/003364 | A2 | 1/2005 |
| WO | 2005/012534 | A1 | 2/2005 |
| WO | 2007/091099 | A1 | 8/2007 |
| WO | 2008/134068 | A2 | 11/2008 |
| WO | 2009/016627 | A1 | 2/2009 |
| WO | 2009/115569 | A1 | 9/2009 |
| WO | 2009/157771 | A2 | 12/2009 |
| WO | 2013/131920 | A1 | 9/2013 |
| WO | WO-2014135604 | A1 | 9/2014 |
| WO | WO-2015185933 | A1 | 12/2015 |
| WO | WO-2018029534 | A1 | 2/2018 |
| WO | WO-2019186175 | A1 | 10/2019 |
| WO | WO-2020035673 | A1 | 2/2020 |

OTHER PUBLICATIONS

Wu et al., "Expression of Highly Controllable Genes in Insect Cells using a Modified Tetracycline-regulated Gene Expression System", Journal of Biotechnology, vol. 80, Issue 1, Jun. 2000, pp. 75-83.

Zhao et al., "Male Germ Cell Specification and Differentiation", Developmental Cell, vol. 2, No. 5, May 2002, pp. 537-547.

Zimowska et al., "The Beta2-tubulin Gene from three Tephritid Fruit Fly Species and Use of Its Promoter for Sperm Marking", Insect Biochemistry and Molecular Biology, vol. 39, No. 8, 2009, pp. 508-515.

Krafsur et al., "Bionomics of the Face Fly, Musca Autumnalis", Annual Review of Entomology, vol. 42, 1997, pp. 503-523.

Lankenau et al., "Comparison of Targeted-Gene Replacement Frequencies in *Drosophila melanogaster* at the Forked and White Loci", Molecular and Cellular Biology, vol. 16, No. 7, 1996, pp. 3535-3544.

Loew et al., "Improved Tet-Responsive Promoters with Minimized Background Expression", BMC Biotechnology, vol. 10, No. 81, 2010.

Louis et al., "A Theoretical Model for the Regulation of Sex-Lethal, a Gene that Controls Sex Determination and Dosage Compensation in *Drosophila melanogaster*", Genetics, vol. 165, Nov. 2003, pp. 1355-1384.

Loukeris et al., "Gene Transfer Into the Medfly, Ceratitis Capitata, with a *Drosophila hydei* Transposable Element", Science, vol. 270, No. 5244,1999, pp. 2002-2005.

Loukeris et al., "Introduction of the Transposable Element Minos into the Germ Line of *Drosophila melanogaster*", Proceedings of the National Academy of Sciences, vol. 92, 1995, pp. 9485-9489.

Lycett et al., "Conditional Expression in the Malaria Mosquito Anopheles stephensi with Tet-On and Tet-Off Systems", Genetics, vol. 167, No. 4, Aug. 2004, pp. 1781-1790.

Mahfouz et al., "De nova-engineered transcription activator-like effector (TALE) hybrid nuclease with novel DNA binding specificity creates double-strand breaks", Proc Natl Acad Sci, vol. 101, No. 6, 2011, pp. 2623-2628.

Malacrida et al., "A transgenic sperm marking system in the medfly, as a tool for pest control strategies and sperm use analysis", Entomological Research, vol. 37, 2007, pp. A56.

Marrelli et al., "Mosquito Transgenesis: what is the fitness cost?", Trends Parasitol, Vo. 22, No. 5, 2006, pp. 197-202.

Mattox et al., "Alternative splicing of the sex determination gene transformer-2 is sex-specific in tile germ line but not in the soma", Genes & Development, vol. 4, No. 5, 1990, pp. 789-805.

Mattox et al., "Autoregulation of the splicing of transcripts from the transformer-2 gene of *Drosophila*", Genes & Development, vol. 5, 1991, pp. 786-796.

Matz et al., "Fluorescent Proteins from Nonbioluminescent Anthozoa Species", Nature Biotechnology, vol. 17, No. 10, 1999, pp. 969-973.

May et al., "Tropical Arthropod Species, More or Less?", Science, vol. 329, 2010, pp. 41-42.

Maynard-Smith et al., "A Directed Approach for Engineering Conditional Protein Stability Using Biologically Silent Small Molecules", Journal of Biological Chemistry, vol. 282, No. 34, 2007, pp. 24866-24872.

Michiels et al., "A 14 Bp Promoter Element Directs the Testis Specificity of the *Drosophila* B2 Tubulin Gene", The EMBO Journal vol. 8, No. 5, 1989, pp. 1559-1565.

Miller et al., "A TALE Nuclease Architecture for Efficient Genome Editing", Nature Biotechnology, vol. 29, No. 2, 2011, pp. 143-148.

Miller et al., "An Improved Zinc-finger Nuclease Architecture for Highly Specific Genome Editing", Nature Biotechnology, vol. 25, No. 7, 2007, pp. 778-785.

Mishra et al., "Understanding Forest Biology", Discovery publishing house, 2009, 3 pages.

Morrison et al., "Engineered repressible lethality for controlling the pink bollworm, a lepidopteran pest of cotton", PLOS One, vol. 7, No. 12:e50922, 2012.

Morrison et al., "Genetic Improvements to The Sterile Insect Technigue for Agricultural Pests", Asia-Pacific Journal of Molecular Biology and Biotechnology, vol. 18, No. 2, 2010, pp. 275-295.

Mounier et al., "Insect Muscle Actins Differ Distinctly from Invertebrate and Vertebrate Cytoplasmic Actins", Journal of Molecular Evolution, vol. 34, No. 5, 1992, pp. 406-415.

Munoz et al., "The AeAct-4 Gene is Expressed in the Developing Flight Muscles of Female Aedes Aeqypti", Insect Molecular Biology, vol. 13, No. 5, Oct. 2004, pp. 563-568.

Namciu et al., "Human Matrix Attachment Regions Insulate Transgene Expression from Chromosomal Position Effects in *Drosophila melanogaster*", Molecular and Cellular Biology, vol. 18, No. 4, 1998, pp. 2382-2391.

Nene et al., "Genome sequence of Aedes aegypti, a major arbovirus vector", Science, vol. 316, No. 5832, 2007, pp. 1718-1723.

Nielsen et al., "Axoneme-specific Beta-tubulin Specialization: A Conserved C-terminal Motif Specifies The Central Pair", Current Biology, vol. 11, No. 7, 2001, pp. 529-533.

Nitasaka et al., "Repressor of P Elements in *Drosophila melanogaster*: Cytotype Determination by a Defective P Element Carrying Only Open Reading Frames 0 Through 2", Proceedings of the National Academy of Sciences of the United States of America, vol. 84, No. 21, 1987, pp. 7605-7608.

Nongthomba et al., "Expression and Function of the *Drosophila* Act88F Actin Isoform is not Restricted to the Indirect Flight Muscles", Journal of Muscle Research and Cell Motility, vol. 22, No. 2, 2001, 1 Page.

O'Brochta et al., "Gene Vector and Transposable Element Behavior in Mosquitos", The Journal of Experimental Biology, vol. 206, 2003, pp. 3823-3834.

Ohshima et al., "Reassessment of 79B actin gene expression in the abdomen of adult *Drosophila melanogaster*", Insect Molecular Biology, vol. 6, No. 3, 1997, 2 pages.

(56) References Cited

OTHER PUBLICATIONS

Olsen, "Fibroblast Growth Factor (FGF) Homologous Factors Share Structural but Not Functional Homology with FGFs", J. Biol. Chem. vol. 278, 2003, pp. 34226-34236.
Osanal-Futahasi et al., "A Visible Dominant Marker for Insect Transgenesis", Nature Communications, vol. 3, No. 1295, 2012.
Osterwalder et al., "A Conditional Tissue-specific Transgene Expression System using Inducible GAL4", Proceedings of the National Academy of Sciences of the United States of America, vol. 98, No. 22, 2001, pp. 12596-12601.
Pane et al., "The Transformer Gene in Ceratitis Capitata Provides a Genetic Basis for Selecting and remembering the Sexual Fate", Dipartimento di Genetica, Biologia Generale e Molecolare, Development 129, 2002, pp. 3715-3725.
Papathanos et al., "Sex Separation Strategies: Past Experience and New Approaches", Malaria Journal, vol. 8, 2009.
Parker et al., "Functional Interaction between Nuclear Inhibitor of Protein Phosphatase Type 1 (NIPP1) and Protein Phosphatase Type 1 (PP1) in *Drosophila*: Consequences of Overexpression Of NIPP1 in Flies and Suppression by Co-expression of PP1", Biochemical Journal, vol. 368, 2002, pp. 789-797.
Parker et al., "Mass-rearing for Sterile Insect Release", The Netherlands, Springer, 2005, pp. 209-232.
Peloquin et al., "Germ-line Transformation of Pink Bollworm (*Lepidoptera gelechiidae*) Mediated by The Piggybac Transposable Element", Insect Molecular Biology, vol. 9, No. 3, 2000, pp. 323-333.
Perera et al., "Germ-line Transformation of the South American Malaria Vector, *Anopheles albimanus*, with a Piggybac/Egfp Transposon Vector, is Routine and Highly Efficient", Insect Molecular Biology, vol. 11, No. 4, 2002, pp. 291-297.
Perezgasga et al., "Regulation of Transcription of Meiotic Cell Cycle and Terminal Differentiation Genes by the Testis-specific Zn-finger Protein Matotopetli", Development, vol. 131, No. 8, 2004, pp. 1691-1702.
Perrin et al., "The Actin Gene Family: Function follows Isoform", Cytoskeleton, vol. 67, No. 10, 2010, pp. 630-634.
Phuc et al., "Late-acting Dominant Lethal Genetic Systems and Mosquito Control", BMC Biology, vol. 5, No. 11, 2007.
Pinkerton et al., "Green Fluorescent Protein as a Genetic Marker in Transgenic Aedes Aegypti", Insect Molecular Biology, vol. 9, No. 1, 2000, pp. 1-10.
Prasher et al., "Primary Structure of the Aequorea Victoria Green-fluorescent Protein", Gene, vol. 111, No. 2, 1992, pp. 229-233.
Qin et al., "Systematic Comparison of Constitutive Promoters and the Doxycycline-inducible Promoter", PLOS One, vol. 5, No. 5, 2010.
Raja et al., "Replacement by *Drosophila melanogaster* Protamines and Mst77F of Histones during Chromatin Condensation in Late Spermatids and Role of Sesame in the Removal of These Proteins from the Male Pronucleus", Molecular and Cellular Biology, vol. 25, No. 14, 2005, pp. 6165-6177.
Remy et al., "Zinc-finger Nucleases: A Powerful Tool for Genetic Engineering of Animals", Transgenic Research, vol. 19,2010, pp. 363-371.
Rendon et al., "Medfly (*Diptera tephritidae*) Genetic Sexing: Large-scale Field Comparison of Males-only and Bisexual Sterile Fly Releases in Guatemala", Journal of Economic Entomology, vol. 97, No. 5,2004, pp. 1547-1553.
Robinson et al., "", Mutation Research, vol. 511, 2002, pp. 113-132.
Robinson et al., "Ceratitis Capitata-a Suitable Case for Genetic Sexing", Genetica, vol. 58, No. 3, 1982, pp. 229-237.
Black et al., "Why RIDL is not SIT", Trends Parasitol, vol. 27, No. 8, 2001, pp. 362-370.
Blitvich et al., "Developmental- and tissue-specific expression of an inhibitor of apoptosis protein 1 homologue from Aedes triseriatus mosquitos", Insect Molecular Biology, vol. 11, No. 5, 2002, pp. 431-442.
Boudrez et al., "Identification of MYPT1 and NIPP1 as subunits of protein phosphatase 1 in rat liver cytosol", FEBS Letters, vol. 455, 1999, pp. 175-178.
Brand et al., "Ectopic expression in *Drosophila*", Methods Cell Biol, vol. 44, 1994, pp. 635-654.
Brand et al., "Targeted gene expression as a means of altering cell fates and generating dominant phenotypes", Development, vol. 118, No. 2, 1993, pp. 401-415.
Burcin et al., "A regulatory system for target gene expression", Frontiers in Biosc. vol. 3(c), 1998, pp. 1-7.
Burn et al., "Alternative 5C actin transcripts are localized in different patterns during *Drosophila* embryogenesis", Dev Biol, vol. 131, No. 2, 1989, pp. 345-355.
Burt et al., "Site-specific selfish genes as tools for the control and genetic engineering of natural populations", Proc Biol Sci. vol. 270, 2003, pp. 921-928.
Cabrera et al., "Expression Pattern of Gal4 Enhancer Trap Insertions into the brie a brae Locus Generated by P Element Replacement", Genesis, vol. 34, 2002, pp. 62-65.
Caceres et al., "Mass rearing of temperature sensitive genetic sexing strains in the Mediterranean fruitfly (*Ceratitis capitata*)", Genetica, vol. 115, No. 1, 2002, pp. 107-116.
Cagan et al., "Spermatogenesis: Borrowing the Apoptotic Machinery", Curr Biol, vol. 13, 2003, pp. R600-R602.
Carriere and Tabashnik,"Reversing Insect Adaptation to Transgenic Insecticidal Plants", Proc. R. Soc. Lond. B. vol. 268, 2001, pp. 1475-1480.
Catteruccia et al., "An Anopheles transgenic sexing strain for vector control", Nat Biotechnol, vol. 23, No. 11, 2005, pp. 1414-1417.
Catteruccia et al., "Impact of genetic manipulation on the fitness of *Anopheles stephensi* mosquitoes", Science, vol. 299, No. 5610, 2000, pp. 1225-1227.
Catteruccia et al., "Stable germline transformation of the malaria mosquito *Anopheles stephensi*", Nature, vol. 105, No. 6789, 2000, pp. 959-962.
Catteruccia et al., "Transgenic technologies to induce sterility", Malaria Journal, vol. 8(SUPP2)S7, 2009.
Cenik et al., "Genome analysis reveals interplay between 5'UTR intrans and nuclear mRNA export for secretory and mitochondrial genes", PLoS Genet, vol. 794:e1001366, 2011.
Cha et al., "Expression of green fluorescent protein in insect larvae and its application for heteroloaous protein production", Biotechnol Bioena, vol. 56, No. 3, 1997, pp. 239-247.
Chalfie et al., "Green fluorescent protein as a marker for gene expression", Science, vol. 263, No. 5148, 1994, pp. 302-805.
Chen et al., "Apoptotic Activity of REAPER is Distinct from Signaling by the Tumor Necrosis Factor Receptor 1 Death Domain", The Journal of Biological Chemistry, vol. 271, No. 42, 1996, pp. 25735-25737.
Chen et al., "The Use of Modified Tetracycline Regulatory Expression System with Reduced Basal Level to Develop and In Vivo Biopesticide Expression System", Food Science Agriculture Chem. vol. 2, No. 4, Oct. 2000, pp. 220-225.
Cheng et al., "Cellular transformation by Simian Virus 40 and Murine Polyoma Virus T antiqens", Semin Cancer Biol, vol. 19, No. 4, 2009, pp. 218-228.
Chintapalli et al., "Using FlyAtlas to identify better *Drosophila melanogaster* models of human disease", Nature Genetics, vol. 39, No. 6, 2007, pp. 715-720.
Cho,"Enhancers", WIREs Dev Biol vol. 1, 2012, pp. 469-478.
Curtis et al., "Assessment of the impact of potential tetracycline exposure on the phenotype of Aedes aegypti OX513A: Implications for field use", PLOS Neglected Tropical Diseases, vol. 9, No. 8, 2015.
Davis et al., "Engineered Underdominance Allows Efficient and Economical Introgression of Traits into Pest Populations", J Theor. Biol., vol. 212, No. 1, 2001, pp. 83-98.
De Valdez et al., "Genetic Elimination of Dengue Vector Mosquitoes", Proceedings of the National Academy of Sciences of the United States of America, vol. 108, No. 12, 2011, 4772-4775.
Deng et al., "A targeted gene silencing technique shows that *Drosophila myosin* VI is required for egg chamber and maginal disc morphogenesis", J Cell Science, vol. 112, 1999, pp. 3677-3690.

(56) References Cited

OTHER PUBLICATIONS

Deredec et al., "The population genetics of using homing endonuclease genes in vector and pest management", Genetics, vol. 179, No. 4, 2008, pp. 2013-2026.
Devault et al., "Biotechnology and new integrated pest management approaches", Nature Biotechnology, vol. 14, 1996, pp. 46-49.
Dhillon, "The melon fruit fly, *Bactrocera cucurbitae*: A review of its biology and management", J Insect Sci., vol. 5, 2005, 40 Pages.
Dyck et al., "Genetic sexing strains in the Mediterranean Fruit Fly, an example for other species amenable to large-scale rearing for the sterile insect technique", Sterile Insect Technique, Principles and Practice in Area-Wide Integrated Pest Management and The Netherlands, Springer, 2005, pp. 427-451.
Egloff et al., "Structural basis for the recognition of regulatory subunits by the catalytic subunit of protein phosphatase 1", EMBO J, vol. 16, No. 8, 1997, pp. 1876-1887.
Elick et al., "Analysis of the Cis-Acting DNA Elements Required for piggyback Transposable Element Excision", Mol. Gen. Genet., vol. 255, 1997, pp. 605-610.
Ernst U, "Regulation of Sexual Differentiation in *Drosophila*: Alternative Splicing of the Transformer Primary Transcript Requires Masking of the Non-Specific Acceptor Site in Females", Inaugural Dissertation, Aus Frankfurt I Main, BRO., 1991.
Eynde et al., "Molecular Cloning of NIPP-1, A Nuclear Inhibitor of Protein Phosphatase-1, Reveals Homology with Polypeptides Involved in RNA Processing", Journal of Biological Chemistry, vol. 270, No. 47, 1995, pp. 28068-28074.
Eynde et al., "Organization and Alternate Splice Products of the Gene Encoding Nuclear Inhibitor of Protein Phosphatase-1 (NIPP-1)", European Joumalof Biochemistry, vol. 261, No. 1,1999, pp. 291-300.
Franz, "Recombination between homologous autosomes in medfly (*Ceratitis capitata*) males: type-1 recombination and the implications for the stability of genetic sexing strains", Genetica, vol. 116, No. 1, 2012, pp. 73-84.
Fraser, "Insect transgenesis: current applications and future prospects", Annu Rev Entomol, vol. 57, 2012, pp. 267-289.
Fryxell et al., "Autocidal biological control: a general strategy for insect control based on genetic transformation with a highly conserved gene", J Econ Entomol, vol. 88, No. 5, 1995, pp. 1221-1232.
Fu et al., "Female-specific flightless phenotype for mosquito control", Proc Natl Acad Sci USA, vol. 107, No. 10, 2010, pp. 4550-4554.
Fu et al., "Female-specific insect lethality engineered using alternative splicing", Nature Biotechnology, vol. 25, No. 3, 2007, pp. 353-357.
FULLER,"Spermatogenesis", The Development of *Drosophila melanogaster*, BATE et al., Cold Spring Harbor Laboratory Press, 1993, pp. 71-147.
Funaguma et al., "The Bmdsx transgene including trimmed introns is sex-specifically spliced in tissues of the silkworm, *Bombyx mori*", Journal of Insect Science (online), vol. 5, No. 17, 2005, pp. 1-6.
Fussenegger et al., "Autoregulated multicistronic expression vectors provide one-step cloning of regulated product gene expression in mammalian cells", Biotechnol. Prog., vol. 13, 1997, pp. 733-740.
Fussenegger et al., "Regulated Multicistronic Expression Technology for Mammalian Metabolic Engineering", Cytotechnology, vol. 28, 1998, pp. 111-126.
Fussenegger et al., "Streptogramin-based gene regulation systems for mammalian cells", Nat Biotechnol, vol. 18, No. 11, 2000, pp. 1203-1208.
Fussenegger et al., "The impact of mammalian gene regulation concepts on functional genomic research, metabolic engineering, and advanced gene therapies", Biotechnol Prog, vol. 17, No. 1, 2001, pp. 1-51.
Fux et al., "Novel Macrolide-Adjustable Bidirectional Expression Modules for Coordinated Expression of Two Different Transgenes in Mice", J Gene Medicine, vol. 5, 2003, pp. 1067-1079.
Ghosh et al., "Transcription factor binding and induced transcription alter chromosomal c-myc replicator activity", Mol Cell Biol, vol. 24, No. 23, 2004, pp. 10193-10207.
Alignment of SEQ ID No. 22 of D1 (WO 2005/012534) with tTAV, Jul. 4, 2014.
Definition of "pest" from the Concise Oxford American Dictionary, Concise Oxford American Dictionary, 2006, 661 pages.
GSN: AAD40186, Retrieved from the internet: <http://ibis.internal.epo.org/exam/dbfetch.jsp?id=GSN:AAD40186>, Oct. 22, 2002.
GSN: BB010346, Retrieved from the internet:<http://ibis.internal.epo.org/exam/dbfetch.jsp?id=GSN:BB010346> , Nov. 6, 2014.
International Preliminary Examination Report for PCT/GB00/04541, dated Apr. 4, 2002, 2 pages.
International Preliminary Report on Patentability for PCT/EP2014/054290, dated Sep. 8, 2015, 7 pages.
International Preliminary Report on Patentability for PCT/GB2004/002021, dated Nov. 18, 2005, 6 pages.
International Preliminary Report on Patentability for PCT/GB2004/002869, dated Jan. 3, 2006, 9 pages.
International Preliminary Report on Patentability for PCT/GB2004/003263, dated Jan. 30, 2006, 6 pages.
International Preliminary Report on Patentability for PCT/GB2007/000488, dated May 5, 2008, 11 pages.
International Search Report and Written Opinion for PCT/EP2013/054417, dated Jul. 12, 2013, 14 pages.
International Search Report and Written Opinion for PCT/EP2014/054290, dated Jun. 18, 2014, 11 pages.
International Search Report and Written Opinion received for PCT Patent Application No. PCT/GB2015/051633, dated Oct. 16, 2015, 11 pages.
International Search Report and Written Opinion received for PCT Patent Application No. PCT/IB2017/001128, dated Dec. 13, 2017, 17 pages.
International Search Report for PCT/GB2000/04541, dated Nov. 19, 2001.
International Search Report for PCT/GB2004/002021, dated Oct. 6, 2004, 3 pages.
International Search Report for PCT/GB2004/002869, dated Jan. 11, 2005, 5 pages.
International Search Report for PCT/GB2004/003263, dated Nov. 5, 2004, 3 pages.
International Search Report for PCT/GB2007/000488, dated Jun. 6, 2007, 3 pages.
Oxitec, Newsletter, http://www.oxitec.com/our-news/newsletters/november-2011-newsletter/, downloaded, Dec. 13, 2011, 6 pages.
PiggyBac Website, http://piaavbac.bio.nd.edu/, Mar. 21, 2006.
Written Opinion received from International Preliminary Examining Authority for PCT Patent Application No. PCT/GB2007/000488, dated Jun. 6, 2007, 8 pages.
Written Opinion received from International Preliminary Examining Authority for PCT Patent Application No. PCT/GB2004/002021, dated Oct. 4, 2004, 5 pages.
Written Opinion received from International Preliminary Examining Authority for PCT Patent Application No. PCT/GB2004/002869, dated Jan. 12, 2005, 8 pages.
Written Opinion received from International Preliminary Examining Authority for PCT Patent Application No. PCT/GB2004/003263, dated Nov. 5, 2004, 5 pages.
Adelman,"Formation and loss of large, unstable tandem arrays of the piggyBac transposable element in the yellow fever mosquito, *Aedes aegypti*", Transgenic Res, vol. 13, No. 5, 2004, pp. 411-425.
Allen et al., "Flight muscle-specific expression of act88F: GFP in transgenic Culex quinauefasciatus Say (*Diptera culicidae*)", Parasitoloqy Int vol. 53, No. 4, 2004, pp. 307-317.
Allen et al., "PiggyBac transformation of the New World screwworm, *Cochliomyia hominivorax*, produces multiple distinct mutant strains", Med. Vet. Entomol vol. 18, Mar. 2004, pp. 1-9.
Allen et al., "Stable, germ-line transformation of Culex quinguefasciatus (*Diptera culicidae*)", J Med Entomol vol. 38, No. 5, 2001, pp. 701-710.
Alphey et al., "Dominant Lethality and Insect Population Control", Mol. Biochem Parasitol. vol. 121 No. 2, May 2002, pp. 173-178.

(56) References Cited

OTHER PUBLICATIONS

Alphey et al., "Malaria control with genetically manipulated insect vectors", Science vol. 298, Oct. 4, 2002, pp. 119-121.
Alphey et al., "Managing Insecticide Resistance by Mass Release of Engineered Insects", J. Econ. Entomol, vol. 100, No. 5, 2007, pp. 1642-1649.
Alphey et al., "Modeling resistance to genetic control of insects", Journal of Theoretical Biology, vol. 270, 2011, pp. 42-55.
Ant et al., "Control of the olive fruit fly using genetics-enhanced sterile insect technique", BMC Biology vol. 10, No. 51, 2012, 8 pages.
Arama et al., "Caspase activity and a specific cytochrome Care required for sperm differentiation in *Drosophila*", Dev Cell vol. 4, No. 5, May 1, 2003, pp. 687-697.
Arribas et al., "The ubiquitin genes in *D. melanogaster*: transcription and polymorphism", Biochimica et Biophysica Acta, vol. 868, 1986, pp. 119-127.
Arya et al., "Basic principles of real-time quantitative PCR", Expert Rev Mol Diagn, vol. 5, No. 2, 2005, pp. 209-219.
Atkinson et al., "Genetic transformation systems in insects", Annu Rev Entomol vol. 46, Jan. 2001, pp. 219-235.
Atkinson et al., "Hermes and Other hAT Elements as Gene Vectors in Insects", Insect Transgenesis: Methods and Applications, Hadler et al. (eds), Boca Raton CRC Press, 2000, pp. 219-235.
Barreau et al., "Post-Meiotic Transcription in *Drosophila* Testes", Development, vol. 135, No. 11, 2008, pp. 1897-1902.
Bauer Dumont et al., "Recurrent positive selection at bgcn, a key determinant of germ line differentiation, does not appear to be driven by simple coevolution with its partner protein bam", Mol Biol Evol vol. 24 No. 1, 2007, pp. 182-191.
Beall et al., "Discovery of tMAC: a *Drosophila* testis-specific meiotic arrest complex paraloqous to Myb-Muv B", Genes Dev vol. 21, No. 8, 2007, pp. 904-919.
Bello et al., "Spatial and temporal targeting of gene expression in *Drosophila* by means of a tetracycline-dependent transactivator system", Development vol. 125, No. 12, 1998, pp. 2193-2202.
Berghammer et al., "A universal marker for transgenic insects", Nature vol. 402, No. 6760, 1999, pp. 370-371.
Beullens et al., "Inactivation of nuclear inhibitory polypeptides of protein phosphatase-1 (NIPP-1) by protein kinase A", J Biol Chem vol. 268, No. 18, 1993, pp. 13172-13177.
Beullens et al., "Molecular determinants of nuclear protein phosphatase-1 regulation by NIPP-1", J Biol Chem, vol. 274, No. 20, 1999, pp. 14053-14061.
Beullens et al., "The isolation of novel inhibitory polypeptides of protein phosphatase 1 from bovine thymus nuclei", J Biol Chem vol. 267, No. 23, 1992, pp. 16538-16544.
Beumer et al., "Efficient gene targeting in *Drosophila* with zinc-finger nucleases", Genetics, vol. 172, No. 4, 2006, pp. 2391-2403.
Bibikova et al., "Targeted chromosomal cleavage and mutagenesis in *Drosophila* using zincfinaer nucleases", Genetics, vol. 161, No. 3, 2002, pp. 1169-1175.
Bieschke et al., "Doxycycline-Induced Transgene Expression During *Drosophila* Development and Aaina", Mol. Gen Genet. vol. 258, No. 6, Jun. 1998, pp. 571-579.
Robinson et al., "Genetic Basis of the Sterile Insect Technique", in: Sterile Insect Technique, Principles and Practice in Area-Wide Integrated Pest Management, 2005, pp. 95-114.
Robinson et al., "Prospects for The Future Development and Application of the Sterile Insect Technique", The Netherlands, Springer, 2005, pp. 727-760.
Ronaldson et al., "Two independent cis-acting elements regulate the sex- and tissuespecific expression of yp3 in *Drosophila melanogaster*", Genet Res., vol. 6, No. 1, 1995, pp. 9-17.
Rong et al., "A Targeted Gene Knockout in *Drosophila*", Genetics, vol. 157, No. 3, 2001, pp. 1307-1312.
Rong et al., "Gene Targeting by Homologous Recombination in *Drosophila*", Science, vol. 288, No. 5473, 2000, pp. 2013-2018.
Rong et al., "Targeted Mutagenesis by Homologous Recombination in *D. melanogaster*", Genes & Development, vol. 16, 2002, pp. 1568-1581.
Roper et al., "Contribution of Sequence Variation in *Drosophila* Actins to their Incorporation Into Actin-based Structures in Vivo", Journal of Cell Science, vol. 118, 2005, pp. 3937-3948.
Rossler et al., "The Genetics of the Mediterranean Fruit Fly: A "White Pupae" Mutant", Annals of the Entomological Society of America, vol. 72, 1979, pp. 583-585.
Rubin et al., "Genetic Transformation of *Drosophila* with Transposable Element Vectors", Science, vol. 218, No. 1570, 1982, pp. 348-353.
Russ et al., "Self-Deleting Retrovirus Vectors for Gene Therapy", Journal of Virology, vol. 70, No. 8, 1996, pp. 4927-4932.
Saccone et al., "Sex Determination in Flies, Fruit Flies and Butterflies", Genetica, vol. 116, 2002, pp. 15-23.
Saccone et al., "Sex Determination in Medfly: A Molecular Approach", Area-Wide Control of Fruit Flies and Other Insect Pests | IAEA, 2000, pp. 491-496.
Salvemini et al., "Genomic organization and splicing evolution of the doublesex gene, a *Drosophila* regulator of sexual differentiation, in the dengue and yellow fever mosquito *Aedes aegypti*", BMC Evolutionary Biology, vol. 11, No. 1:41, 2011.
Santel et al., "The *Drosophila* Don Juan (Dj) Gene Encodes a Novel Sperm Specific Protein Component Characterized by an Unusual Domain of a Repetitive Amino Acid Motif", Mechanisms of Development, vol. 64, No. 1-2, 1997, pp. 19-30.
Scali et al., "Identification of Sex-specific Transcripts of the Anopheles Gambiae Doublesex Qene", Journal of Experimental Bioloqy, vol. 208, No. 19, Oct. 2005, pp. 3701-3709.
Schetelig et al., "Strategy for Enhanced Transgenic Strain Development for Embryonic Conditional Lethality in Anastrepha Suspensa", Proceedings of the National Academy of Sciences of the United States of America, vol. 24, 2012, pp. 9348-9353.
Schwechheimer et al., "Transactivation of a Target Gene Through Feedforward Loop Activation in Plants", Functional & Integrative Genomics, vol. 1, 2000, pp. 35-43.
Sepp et al., "Conversion of Lacz Enhancer Trap Lines to Gal4 Lines using Targeted Transposition in *Drosophila melanogaster*", Genetics, vol. 151, 1999, pp. 1093-1101.
Shah et al., "Cardiac remodeling in *Drosophila* arises from changes in actin gene expression and from a contribution of lymph gland-like cells to the heart musculature", Mechanisms of Development, vol. 128, No. 3, 2011, pp. 222-233.
Shelton et al., "Field Tests on Managing Resistance to Bt-engineered Plants", Nature Biotechnology, vol. 18, 2000, pp. 339-342.
Shockett et al., "A Modified Tetracycline-Regulated System Provides Autoregulatory, Inducible Gene Expression in Cultured Cells and Transgenic Mice", Proceedings of the National Academy of Sciences of the United States of America, vol. 92, Jul. 1995, pp. 6522-6526.
Simmons et al., "Field Performance of a Genetically Engineered Strain of Pink Bollworm", PLoS ONE, vol. 6 (9), e24110, Sep. 2011, 11 pages.
Smith et al., "Testis-specific Expression of The Beta2 Tubulin Promoter of Aedes Aegypti and It's Armlication as a Genetic Sex-separation Marker", Insect Molecular Biology, vol. 16, No. 1, 2007, pp. 16-71.
Sondergaard et al., "Nutritional Response in a *Drosophila* Yolk Protein Gene Promoter", Molecular Genetics and Genomics, vol. 248, No. 1, 1995, pp. 25-32.
Spradling et al., "P Element-mediated Transformation", *Drosophila*: A Practical Approach, Chapter 8, 1986, pp. 175-197.
Spradling et al., "Transposition of Cloned P Elements Into *Drosophila* Germ Line Chromosomes", Science, vol. 218, No. 4570, 1982, pp. 341-347.
Stadtfeld et al., "Without A Trace? Piggybac-ing Toward Pluripotency", Nature Methods, vol. 6, No. 5, 2009, pp. 329-330.
Stebbins et al., "Adaptable Doxycycline-Regulated Gene Expression Systems for *Drosophila*", Gene, vol. 270, 2001, pp. 103-111.

(56) References Cited

OTHER PUBLICATIONS

Stebbins et al., "Tetracycline-Inducible Systems for *Drosophila*", Proceedings of the National Academy of Sciences of the United States of America, vol. 98, 2001, pp. 10775-10780.
Steiner et al., "Homologous Recombination as the Main Mechanism for DNA Integration and Cause of Rearrangements in the Filamentous Ascomycete Ashbya Gossypii", Genetics, vol. 140, 1995, pp. 973-987.
Tamura et al., "Germline Transformation of The Silkworm *Bombyx mori* L. using a Piggyback Transooson-derived Vector", Nature Biotechnology, vol. 18, No. 1, 2000, pp. 81-84.
Theodoraki et al., "cDna Cloning, Heat Shock Regulation and Developmental Expression of the Hsp83 Gene in the Mediterranean Fruit Fly *Ceratitis capitata*", Insect Molecular Biology, vol. 15, No. 6, 2006, pp. 839-852.
Thomas et al., "Insect Population Control using a Dominant, Repressible, Lethal Genetic System", Science, vol. 287, No. 5462, 2000, pp. 2474-2476.
Timoshevskiy et al., "An integrated linkage, chromosome, and Genome map for the Yellow Fever Mosquito *Aedes aegypti*", PLOS Neglected Tropical Diseases, vol. 7, No. 2:e2052, 2013.
Timoshevskiy et al., "Genomic composition and evolution of Aedes aegypti chromosomes revealed by the analysis of physically mapped supercontigs", BMC Biology vol. 12, No. 1:27, 2014.
Urnov et al., "Highly Efficient Endogenous Human Gene Correction using Designed Zinc-finger Nucleases", Nature, vol. 435, 2005, pp. 646-651.
Viktorinova et al., "Comparative Analysis of Binary Expression Systems for Directed Gene Expression in Transqenic Insects", Insect Biochemistry and Molecular Biology, vol. 37, 2007, pp. 246-254.
Vivinus et al., "", European Journal of Biochemistry, vol. 268, 2001, pp. 1908-1917.
Vreysen et al., "Engineering Insects for the Sterile Insect Technique", Dordrecht, The Netherlands, Springer, 2007, pp. 51-60.
Vulsteke et al., "Properties And Phosphorylation Sites Of Baculovirus-expressed Nuclear Inhibitor Of Protein Phosphatase-1 (Nipp-1 }", Journal of Biological Chemistry, vol. 272, No. 52, 1997, pp. 32972-32978.
Webster et al., "", Cell, vol. 52, 1988, pp. 169-178.
Weinmann et al., "A Chimeric Transactivator Allows Tetracycline-responsive Gene Expression In Whole Plants", The Plant Journal, vol. 5, No. 4, 1994, pp. 559-569.
Wera et al., "Inhibition Of Translation By Mrna Encoding Nipp-1, A Nuclear Inhibitor Of Protein Phosphatase-1", European Journal of Biochemistry, vol. 247, No. 1, 1997, pp. 411-415.
Wharton et al., "CNS Midline Enhancers Of The *Drosophila* Slit And Toll Genes", Mechanisms of Development, vol. 10, No. 3, 1993, pp. 141-154.
White-Cooper et al., "Transcription Of Meiotic Cell Cycle And Terminal Differentiation Genes Depends On A Conserved Chromatin Associated Protein, Whose Nuclear Localisation Is Requlated", Development, vol. 127, 2000, pp. 5463-5473.
Wilson et al., "Position Effects On Eukaryotic Gene Expression", Annual Review of Cell and Developmental Biology, vol. 6, 1990, pp. 679-714.
Wilson et al., "Sperm Plasma Membrane Breakdown During *Drosophila* Fertilization Requires Sneakv, An Acrosomal Membrane Protein", Development, vol. 133, No. 24, 2006, pp. 4871-4879.
Wimmer et al., "Eco-friendly Insect Management", Nature Biotechnology, vol. 23, No. 4, 2005, pp. 432-433.
Windbichler et al., "A Synthetic Homing Endonuclease-based Gene Drive System In The Human Malaria Mosquito", Nature, vol. 473, No. 7346, 2011, pp. 212-215.
Windbichler et al., "Homing Endonuclease Mediated Gene Targeting in Anopheles Gambiae Cells and Embryos", Nucleic Acids Research, vol. 35, 2007, pp. 5922-5933.
Alphey et al., (2002). "Re-engineering the sterile insect technique," Insect Biochem Mol Biol., 32:1243-1247. Abstract Only.
Alphey, "Engineering Insects for the Sterile Insect Technique," in: Area-wide Control of Insect Pests: from Research to Field Implementation, VREYSEN et al., (eds.), Dordrecht, The Netherlands, Springer (2007) pp. 51-60.
Diamantidis et al., (2008). "Life-history evolution of an invasive tephritid," J. Appl. Entomol., 132:695-705. Abstract Only.
Franz, "Genetic sexing strains in the Mediterranean Fruit Fly, an example for other species amenable to large-scale rearing for the sterile insect technique" in:Sterile Insect Technique, Principles and Practice in Area-Wide Integrated Pest Management, DYCK et al., (eds), The Netherlands, Springer (2005) pp. 427-451.
Gill et al., (1988). "Negative effect of the transcriptional activator GAL4," Nature, 334(6184):721-724.
Great Britain Application No. 1303932.6, filed Mar. 5, 2013, 42 pages.
Hadjieconomou et al., "Flybow: genetic multicolor cell labeling for neural circuit analysis in *Drosophila melanogaster*", Nature Methods, vol. 8, 2011, pp. 260-266.
Hagler et al., (1994). "Determining the frequency of heteropteran predation on sweetpotato whitefly and pink bollworm using multiple ELISAs," Entomol. Exp. Appl., 72:59-66.
Hansen et al., "Quantifying changes in the rates of forest clearing in Indonesia from 1990 to 2005 using remotely sensed data sets", Environmental Research Letters, vol. 4, 2009, 12 pages.
Hansen et al., (2009). "Genome-Wide Identification of Alternative Splice Forms Down-Regulated by Nonsense-Mediated mRNA Decay in *Drosophila*," PLOS Genetics, 5(6):e1000525, 14 pages.
Hendrichs et al., "Strategic Options in using Sterile Insects For Area-Wide Integrated Pest Management", Sterile Insect Technique, Springer, Netherlands, 2005, pp. 563-600.
Leftwich et al., (2014). "Genetic elimination of field-cage populations of Mediterranean fruit flies," Proc Biol Sci, 281 (1792):20141372.
Li et al., "piggyBac internal sequences are necessary for efficient transformation of target genomes", Insect Molecular Biology, vol. 14 (1), Jan. 2005, pp. 17-30.
Lukyanov et al., "Natural Animal Coloration Can Be Determined by a Nonfluorescent Green Fluorescent Protein Homolog", The Journal of Biological Chemistry, vol. 275 (34), 2000, pp. 25879-25882.
Nagaraju et al., "Lepidopteran Sex Determination: A Cascade of Surprises", Sexual Development, vol. 8, Available online at: <htlps://doi.org/10.1159/000357483>, 2014, pp. 104-112.
Pane et al., (2002). "The transformer gene in Ceratitis capitata provides a genetic basis for selecting and remembering the sexual fate," Development, 129:3715-3725.
Papathanos et al., "Sex separation strategies: past experience and new approaches," Malar J. (2009) 8 Suoo 2:S5.
Perezgasga et al., "Regulation of transcription of meiotic cell cycle and terminal differentiation genes by the testis-specific Zn-finger protein matotopetli," Development (2004) 131 (8):1691-1702.
Shukla et al., "Two female-specific DSX proteins are encoded by the sex-specific transcripts of dsx, and are required orfemale sexual differentiation in two wild silkmoth species, Antheraea assama and Antheraea mylitta {Lepidoptera, Saturniidae)", Insect Biochemistry and Molecular Biology, vol. 40 (9), Sep. 2010, pp. 672-682.
Suzuki et al., "Role of the male BmDSX protein in the sexual differentiation of Bombyx mori", Evolution & Development, vol. 7 (1), 2005, pp. 58-68.
Tan et al., "Transgene-based, female-specific lethality system for genetic sexing of the silkworm, Bombyx mori", PNAS, vol. 110 (17) Available online at: hllps://doi.org/10.1073/pnas.1221700110>, Apr. 23, 2013, pp. 6766-6770.
Thibault et al., "Precise excision and transposition of piggyBac in pink bollworm embryos", Insect Molecular Biology, vol. 8 (1), Feb. 1999, pp. 119-123.
Van Eynde et al., "Organization and alternate splice products of the gene encoding nuclear inhibitor of protein phosphatase-1 (IPP-1)," Eur J Biochem (1999) 261(1):291-300.
Wang et al., "Conserved RNA cis-elements regulate alternative splicing of Lepidopteran doublesex," Insect Biochemistry and Molecular Biology, vol. 44, Jan. 2014, 11 pages.

(56) References Cited

OTHER PUBLICATIONS

Wilson et al., "Hepatocyte-directed Gene Transfer in Vivo Leads to Transient Improvement of Hypercholesterolemia in Low Density Lipoprotein Receptor-deficient Rabbits," J Biol Chem, vol. 267, 1992, pp. 963-967.
Wing et al., "The RHG motifs of *Drosophila* Reaper and Grim are important for their distinct cell death-inducing abilities", Mechanisms of Development, vol. 102, 2001, pp. 193-203.
Wise De Valdez et al., "Genetic elimination of dengue vector mosquitoes," Proc Natl Acad Sci USA (2011} 108(12):4772-4775.
Wu et al., "Receptor-mediated Gene Delivery and Expression in Vivo," J Biological Chemistry, vol. 263, 1988, pp. 14621-14624.
Xu et al., "Sexually dimorphic traits in the silkworm, *Bombyx mori*, are regulated by doublesex", Insect Biochemistry and Molecular Biology vol. 80, Jan. 2017, pp. 42-51.
Advisory Action for U.S. Appl. No. 11/733,737, dated Jun. 3, 2013, 7 pages.
Advisory Action for U.S. Appl. No. 11/733,737, dated Aug. 5, 2009, 4 pages.
Amendment for U.S. Appl. No. 10/562,843, filed Feb. 24, 2009, 13 pages.
Amendment for U.S. Appl. No. 10/562,843, filed Nov. 30, 2010, 7 pages.
Amendment for U.S. Appl. No. 10/562,843, filed Oct. 5, 2009, 10 pages.
Amendment for U.S. Appl. No. 10/566,448, filed Oct. 27, 2010, 20 pages.
Amendment for U.S. Appl. No. 10/566,448, filed Jul. 7, 2009, 15 pages.
Amendment for U.S. Appl. No. 11/352,177, filed Dec. 10, 2009, 20 pages.
Amendment for U.S. Appl. No. 11/352,177, filed Oct. 14, 2010, 13 pages.
Appeal Brief for U.S. Appl. No. 11/733,737, filed Feb. 3, 2014, 40 pages.
Appeal Brief for U.S. Appl. No. 12/278,849, filed Oct. 16, 2014, 31 pages.
Communication pursuantto Article 94(3) EPC for EP 07712717.3, dated Jul. 11, 2014, 8 pages.
Communication pursuantto Article 94(3) EPC for EP 07712717.3, dated Nov. 6, 2015, 4 pages.
Communication pursuant to Article 96(2) EPC for EP 00979774.7, dated Aug. 2, 2005, 4 pages.
Communication pursuant to Article 96(2) EPC for EP 00979774.7, dated Nov. 28, 2003, 5 pages.
Communication pursuantto Article 96(2) EPC for EP 00979774.7, dated Oct. 4, 2004, 4 pages.
Communication pursuant to Article 96(2) EPC for EP 00979774.7, dated Mar. 8, 2006, 4 pages.
Communication under Rule 51 (4) EPC, directed to EP 00979774.7, dated May 9, 2007, 4 pages.
Communication under Rule 71 (3) EPC for EP 07712717.3, dated Jun. 20, 2016, 7 pages.
Decision on Further Processing for EP 00979774.7, dated Jan. 29, 2007, 1 page.
EP First Office Action, dated Feb. 16, 2012, in European Patent Application No. 04743590.4, a corresponding application, 8 pages.
Examination Report for EP 04743590.4, dated Nov. 14, 2008, 4 pages.
Examination Report for NZ 519175, dated Nov. 28, 2003, 1 page.
Examination Report for NZ 519175, dated Jul. 9, 2002, 2 pages.
Examiner's Answer to Appeal Brief for U.S. Appl. No. 11/733,737, dated Jul. 18, 2014, 12 pages.
Final Office Action for U.S. Appl. No. 10/148,041, dated Mar. 7, 2006, 9 pages.
Final Office Action for U.S. Appl. No. 10/562,843, filed Aug. 25, 2011, 5 pages.
Final Office Action for U.S. Appl. No. 10/562,843, dated Feb. 3, 2010, 5 pages.
Final Office Action for U.S. Appl. No. 10/566,448, dated Nov. 10, 2009, 18 pages.
Final Office Action for U.S. Appl. No. 10/566,448, dated Aug. 14, 2014, 24 pages.
Final Office Action for U.S. Appl. No. 10/566,448, dated Feb. 2, 2011, 13 pages.
Final Office Action for U.S. Appl. No. 11/352,177, dated Oct. 14, 2014, 6 pages.
Final Office Action for U.S. Appl. No. 11/352,177, dated Mar. 16, 2011, 18 pages.
Final Office Action for U.S. Appl. No. 11/733,737, dated Apr. 17, 2009, 16 pages.
Final Office Action for U.S. Appl. No. 11/733,737, dated Aug. 4, 2010, 18 pages.
Final Office Action for U.S. Appl. No. 11/733,737, dated Jan. 7, 2013, 26 pages.
Final Office Action for U.S. Appl. No. 12/278,849, dated Jun. 6, 2013, 24 pages.
Final Office Action for U.S. Appl. No. 12/278,849, dated Mar. 17, 2014, 24 pages.
Final Office Action for U.S. Appl. No. 12/278,849, dated Oct. 9, 2015, 7 pages.
Final Office Action for U.S. Appl. No. 13/942,601, dated Jul. 31, 2014, 23 pages.
Formal Report (translation) for BR PI0707579-0, dated Jun. 21, 2016, 2 pages.
Formal Report (translation) for BR PI0413024-3, dated Jun. 7, 2016, 10 pages.
Further International Search Report GB 9928181.8; dated Apr. 30, 2001, 2 pages.
International Search Report and Written Opinion received for PCT Patent Application No. PCT/GB2019/050897, dated Jun. 18, 2019, 10 pages.
Notice of Allowance for U.S. Appl. No. 10/566,448, dated Jul. 13, 2015, 10 pages.
Notice of Allowance for U.S. Appl. No. 10/566,448, dated Mar. 19, 2015, 10 pages.
Notice of Allowance for U.S. Appl. No. 11/352,177, dated Mar. 17, 2015, 10 pages.
Notice of Allowance for U.S. Appl. No. 11/352,177, dated Jul. 7, 2015, 9 pages.
Notice of Allowance for U.S. Appl. No. 13/942,601, dated Apr. 10, 2015, 11 pages.
Notice of Allowance for U.S. Appl. No. 13/942,601, dated Jul. 7, 2015, 9 pages.
Notice of Appeal for U.S. Appl. No. 10/566,448, filed Feb. 18, 2015, 4 pages.
Notice of Appeal for U.S. Appl. No. 11/733,737, filed Jul. 3, 2013, 1 page.
Notice of Appeal for U.S. Appl. No. 12/278,849, filed Jun. 17, 2014, 1 page.
Notice of Appeal for U.S. Appl. No. 13/942,601, filed Feb. 2, 2015, 1 page.
Noting of loss of rights (R. 69(1) EPC) for EP 00979774.7, mailed Jul. 17, 2004, 1 page.
Office Action for AU 17165/01, dated Jul. 13, 2004, 3 pages.
Office Action for CN 00818682.0, fax dated Feb. 4, 2005, 7 pages.
Office Action for IL 149885, dated Apr. 26, 2007, 4 pages.
Office Action for U.S. Appl. No. 10/148,041, dated Jul. 1, 2005, 14 pages.
Office Action for U.S. Appl. No. 10/148,041, dated Oct. 10, 2006, 8 pages.
Office Action for U.S. Appl. No. 10/556,804, dated Feb. 1, 2011, 4 pages.
Office Action for U.S. Appl. No. 10/556,804, dated May 12, 2010, 8 pages.
Office Action for U.S. Appl. No. 10/562,843, dated Nov. 12, 2008, 6 pages.
Office Action for U.S. Appl. No. 10/562,843, dated Feb. 16, 2011, 4 pages.
Office Action for U.S. Appl. No. 10/562,843, dated Jul. 30, 2010, 7 pages.

(56) References Cited

OTHER PUBLICATIONS

Office Action for U.S. Appl. No. 10/562,843, dated Jun. 9, 2009, 5 pages.
Office Action for U.S. Appl. No. 10/566,448, dated Nov. 22, 2013, 24 pages.
Office Action for U.S. Appl. No. 10/566,448, dated Apr. 27, 2010, 12 pages.
Office Action for U.S. Appl. No. 10/566,448, dated Jan. 7, 2009, 14 pages.
Office Action for U.S. Appl. No. 11/352,177, dated Jan. 30, 2014, 17 pages.
Office Action for U.S. Appl. No. 11/352,177, dated Jun. 10, 2009, 14 pages.
Office Action for U.S. Appl. No. 11/352,177, dated Apr. 14, 2010, 15 pages.
Office Action for U.S. Appl. No. 11/733,737, dated Oct. 1, 2009, 21 pages.
Office Action for U.S. Appl. No. 11/733,737, dated Apr. 10, 2008, 8 pages.
Office Action for U.S. Appl. No. 11/733,737, dated Mar. 27, 2012, 17 pages.
Office Action for U.S. Appl. No. 11/733,737, dated Jun. 28, 2011, 14 pages.
Office Action for U.S. Appl. No. 11/733,737, dated Feb. 8, 2011, 6 pages.
Office Action for U.S. Appl. No. 12/278,849, dated Aug. 9, 2013, 22 pages.
Office Action for U.S. Appl. No. 12/278,849, dated Oct. 10, 2012, 12 pages.
Office Action for U.S. Appl. No. 12/278,849, dated Mar. 10, 2015, 18 pages.
Office Action for U.S. Appl. No. 12/278,849, dated Dec. 5, 2014, 15 pages.
Office Action for U.S. Appl. No. 13/942,601, dated Nov. 4, 2013, 17 pages.
Prosecution history for related U.S. Appl. No. 10/148,041, 64 pages.
Prosecution history for related U.S. Appl. No. 10/556,804, 27 pages.
Prosecution history for related U.S. Appl. No. 10/562,843, 63 pages.
Prosecution history for related U.S. Appl. No. 10/566,448, 142 pages.
Prosecution history for related U.S. Appl. No. 11/352,177, 129 pages.
Prosecution history for related U.S. Appl. No. 11/733,737, 175 pages.
Prosecution history for related U.S. Appl. No. 12/278,849, 20 pages.
Rejection for CN 00818682.0, fax dated Jan. 26, 2006, 4 pages.
Reply Brief and Request for Oral Hearing for U.S. Appl. No. 11/733,737, filed Sep. 18, 2014, 16 pages.
Request for Continued Examination for U.S. Appl. No. 10/148,041, filed Sep. 11, 2006, 8 pages.
Request for Continued Examination for U.S. Appl. No. 10/566,448, filed Jun. 18, 2015, 3 pages.
Request for Continued Examination for U.S. Appl. No. 10/566,448, filed Aug. 2, 2011, 23 pages.
Request for Continued Examination for U.S. Appl. No. 10/566,448, filed Feb. 25, 2010, 18 pages.
Request for Continued Examination for U.S. Appl. No. 11/352,177, filed Sep. 16, 2011,3 pages.
Request for Continued Examination for U.S. Appl. No. 11/352,177, filed Jun. 17, 2015, 3 pages.
Request for Continued Examination for U.S. Appl. No. 11/733,737, filed Aug. 14, 2009, 1 page.
Request for Continued Examination for U.S. Appl. No. 13/942,601, filed Jun. 19, 2015, 3 pages.
Request for Further Processing for EP 00979774.7, filed Jan. 4, 2007, 4 pages.
Response for U.S. Appl. No. 10/562,843, filed Feb. 24, 2009, 13 pages.
Response for U.S. Appl. No. 10/562,843, filed Nov. 30, 2010, 8 pages.
Response for U.S. Appl. No. 10/562,843, filed Oct. 5, 2009, 10 pages.
Response for U.S. Appl. No. 11/352,177, filed Dec. 10, 2009, 20 pages.
Response for U.S. Appl. No. 11/352,177, filed Oct. 14, 2010, 13 pages.
Response to Communication for EP 00979774.7, filed Apr. 14, 2005, 7 pages.
Response to Communication for EP 00979774.7, filed Sep. 20, 2004, 8 pages.
Response to Communication pursuantto Article 94(3) EPC, for EP 07712717.3 filed Mar. 16, 2016, 5 pages.
Response to Communication pursuant to Article 96(2) EPC for EP 00979774.7, filed Feb. 13, 2006, 8 pages.
Response to Final Office Action for U.S. Appl. No. 10/562,843, filed Nov. 21, 2011, 6 pages.
Response to Final Office Action for U.S. Appl. No. 10/566,448, filed Dec. 15, 2014, 9 pages.
Response to Final Office Action for U.S. Appl. No. 11/352,177, filed Sep. 16, 2011, 15 pages.
Response to Final Office Action for U.S. Appl. No. 11/352,177, filed Dec. 3, 2014, 8 pages.
Response to Final Office Action for U.S. Appl. No. 11/733,737, filed Jul. 17, 2009, 26 pages.
Response to Final Office Action for U.S. Appl. No. 11/733,737, filed Dec. 6, 2010, 26 pages.
Response to Final Office Action for U.S. Appl. No. 11/733,737, filed Apr. 8, 2013, 25 pages.
Response to Office Action for U.S. Appl. No. 10/148,041, filed Dec. 5, 2005, 11 pages.
Response to Office Action for U.S. Appl. No. 10/556,804, filed Nov. 12, 2010, 12 pages.
Response to Office Action for U.S. Appl. No. 10/556,804, filed Mar. 25, 2011, 9 pages.
Response to Office Action for U.S. Appl. No. 10/562,843, filed Jun. 16, 2011, 9 pages.
Response to Office Action for U.S. Appl. No. 10/566,448, filed Apr. 22, 2014, 17 pages.
Response to Office Action for U.S. Appl. No. 10/566,448, filed Oct. 27, 2010, 20 pages.
Response to Office Action for U.S. Appl. No. 10/566,448, filed Aug. 28, 2009, 15 pages.
Response to Office Action for U.S. Appl. No. 10/566,448, filed Jul. 7, 2009, 15 pages.
Response to Office Action for U.S. Appl. No. 11/352,177, dated May 28, 2014, 14 pages.
Response to Office Action for U.S. Appl. No. 11/733,737, filed Oct. 10, 2008, 8 pages.
Response to Office Action for U.S. Appl. No. 11/733,737, filed Feb. 18, 2011, 11 pages.
Response to Office Action for U.S. Appl. No. 11/733,737, filed Oct. 28, 2011, 27 pages.
Response to Office Action for U.S. Appl. No. 11/733,737, filed Jan. 29, 2010, 23 pages.
Response to Office Action for U.S. Appl. No. 11/733,737, filed Aug. 9, 2012, 24 pages.
Response to Office Action for U.S. Appl. No. 12/278,849, dated Apr. 10, 2013, 19 pages.
Response to Office Action for U.S. Appl. No. 12/278,849, dated Jan. 9, 2014, 21 pages.
Response to Office Action for U.S. Appl. No. 12/278,849, filed Aug. 7, 2015, 24 pages.
Response to Office Action for U.S. Appl. No. 13/942,601, dated Feb. 4, 2014, 45 pages.
Response to Restriction Requirement for U.S. Appl. No. 10/148,041, filed Apr. 13, 2005, 10 pages.
Response to Restriction Requirement for U.S. Appl. No. 10/556,804, filed Jun. 29, 2009, 2 pages.
Response to Restriction Requirement for U.S. Appl. No. 10/562,843, filed Jun. 27, 2008, 2 pages.
Response to Restriction Requirement for U.S. Appl. No. 10/566,448, filed Dec. 1, 2008, 9 pages.

(56) References Cited

OTHER PUBLICATIONS

Response to Restriction Requirement for U.S. Appl. No. 10/566,448, filed Feb. 8, 2008, 9 pages.
Response to Restriction Requirement for U.S. Appl. No. 11/352,177, filed Mar. 13, 2009, 12 pages.
Response to Restriction Requirement for U.S. Appl. No. 11/352,177, filed Nov. 3, 2008, 8 pages.
Response to Restriction Requirement for U.S. Appl. No. 11/352,177, filed Jun. 9, 2008, 9 pages.
Response to Restriction Requirement for U.S. Appl. No. 11/733,737, filed Jan. 26, 2009, 8 pages.
Response to Restriction Requirement for U.S. Appl. No. 12/278,849, filed Sep. 28, 2010, 13 pages.
Restriction Requirement for U.S. Appl. No. 10/148,041, dated Mar. 10, 2005, 5 pages.
Restriction Requirement for U.S. Appl. No. 10/556,804, dated May 28, 2009, 5 pages.
Restriction Requirement for U.S. Appl. No. 10/562,843, dated Jun. 12, 2008, 6 pages.
Restriction Requirement for U.S. Appl. No. 10/566,448, dated Aug. 29, 2008, 7 pages.
Restriction Requirement for U.S. Appl. No. 10/566,448, dated Jan. 9, 2008, 5 pages.
Restriction Requirement for U.S. Appl. No. 11/352,177, dated Jan. 13, 2009, 10 pages.
Restriction Requirement for U.S. Appl. No. 11/352,177, dated Sep. 2, 2008, 5 pages.
Restriction Requirement for U.S. Appl. No. 11/352,177, dated Mar. 31, 2008, 8 pages.
Restriction Requirement for U.S. Appl. No. 11/733,737, dated Dec. 31, 2008, 9 pages.
Restriction Requirement for U.S. Appl. No. 12/278,849, dated May 28, 2010, 7 pages.
Search Report for GB 0317656.7, date of search Nov. 25, 2003, 1 page.
Search Report for GB 0621234.4, dated of search Feb. 21, 2007, 1 page.
Second Office Action for AU 17165/01, dated Mar. 21, 2006, 2 pages.
Second Office Action for CN 00818682.0, dated Jul. 28, 2006, 4 pages.
Summary of Office Action for MX PA/a/2002/005337, dated Jan. 3, 2007, 2 pages.
Supplemental Amendment for U.S. Appl. No. 11/352,177, filed Oct. 21, 2010, 15 pages.
Supplemental Response for U.S. Appl. No. 11/352,177, filed Dec. 6, 2010, 4 pages.
Bennett et al., "Ectopic Expression of Inhibitors of Protein Phosphatase Type 1 (PP1) Can Be Used to Analyze Roles of PP1 in *Drosophila* Development", Department of Zoology, Oxford University, Oxford OX1 3PS, United Kingdom, Genetics 164, May 2003, pp. 235-245.
Cande et al., "Apoptosis-Inducing Factor (AIF): Key to the Conserved Caspase-Independent Pathways of Cell Death?", Journal of Cell Science, vol. 115, No. 24, 2002, pp. 4727-4734.
Choi et al., "The Baculovirus Transactivator IE1 Binds to Viral Enhancer Elements in the Absence of Insect Cell Factors", Journal of Virology, vol. 69, No. 7, 1995, pp. 4548-4551.
Dafa'Alla et al., "Transposon-Free Insertions for Insect Genetic Engineering", Nature Biotechnology, vol. 24, No. 7, Jul. 2006, pp. 820-821.
FAO/IAEA/USDA, "Product Quality Control and Shipping Procedures for Sterile Mass-reared Tephritid Fruit Flies", AEA, Vienna, Version 5.0, May 2003, 2 pages.
Huang et al., "Evolutionary conservation of apoptosis mechanisms: Lepidopteran and baculoviral inhibitor of apoptosis proteins are inhibitors of mammalian caspase-9", PNAS, vol. 97, No. 4, Feb. 15, 2000, pp. 1427-1432.
Mumford, John D., "Science, Regulation, and Precedent for Genetically Modified Insects", PLoS, vol. 6, Issue 1, Jan. 2012, 4 pages.
Leftwich, Philip T., "Male reproductive success and population control in the Mediterranean Fruit Fly, *Ceratitis capitata*". School of Biological Sciences, Aug. 2012, 226 pages.
McInnis et al., "Mating and Remating of Medflies (*Diptera tephritidae*) in Guatemala: Individual Fly Marking in Field Cages", Florida Entomologist, vol. 85(1), Mar. 2002, pp. 126-137.
Olson et al., "A GH3-like Domain in Reaper Is Required for Mitochondrial Localization and Induction of IAP Degradation", The Journal of Biological Chemistry, vol. 278, No. 45, 2003, pp. 44758-44768.
Robinson et al., "Recent Findings on Medfly Sexual Behaviour: Implications for SIT", Florida Entomologist, 85(1), Mar. 2002, pp. 171-181.
Vernooy et al., "Cell Death Regulation in *Drosophila*: Conservation of Mechanism and Unique Insights", The Journal of Cell Biology, vol. 150, No. 2, Jul. 2000, pp. F69-F75.
White et al., "Cell Killing by the *Drosophila* Gene reaper", Science, vol. 271, Feb. 9, 1996, pp. 805-807.
Wing et al., "Distinct Cell Killing Properties of the *Drosophila* reaper, Head Involution Defective, and Grim Genes", Dell Death and Differentiation, 1998, pp. 930-939.
Gloor et al., "Targeted Gene Replacement in *Drosophila* Via P Element-Induced Gap Repair", Science, vol. 253, 1991, pp. 1110-1117.
Golovnin et al., "The su(Hw) insulator can disrupt enhancer-promoter interactions when located more than 20 kilobases away from the *Drosophila* achaete-scute complex", Mol Cell Biol, vol. 19, No. 5,1999, pp. 3443-3456.
Gonczy, "Bag-of-marbles and benign gonial cell neoplasm act in the germline to restrict proliferation during *Drosophila* spermatogenesis", Development, vol. 124, No. 21, 1997, pp. 4361-4371.
Gong et al., "A dominant lethal genetic system for autocidal control of the Mediterranean fruit fly", Nat Biotechnol, vol. 23, No. 4, 2005, pp. 453-456.
Gong et al., "Ends-out, or replacement, gene targeting in *Drosophila*", Proc Natl Acad Sci (USA), vol. 100, No. 5, 2003, pp. 2556-2561.
Gonzy-Treboul et al., "Enhancer-Trap Targeting at the Broad-Complex Locus of *Drosophila melanogaster*", Genes Dev. vol. 9, 1995, pp. 1137-1148.
Gossen et al., "Studying gene function in eukaryotes by conditional gene inactivation", Annu Rev Genet, vol. 36, 2002, pp. 153-173.
Gossen et al., "Tetracycline in Biology, Chemistry and Medicine", 2001, pp. 139-157.
Gossen et al., "Tight control of gene expression in mammalian cells by tetracycline-responsive promoters", Proc Natl Acad Sci (USA), vol. 89, No. 12, 1992, pp. 5547-5551.
Graham et al., "Larval diets containing dyes for tagging pink bollworm moth internally", J Econ Entomol, vol. 64, 1971, pp. 376-379.
Guo et al., "Species-specific signals for the splicing of a short *Drosophila* intron in vitro", Mol Cell Biol, vol. 13, No. 02, 1993, pp. 1104-1118.
Hagler, "An Alternative to Conventional Insect Marking Procedures; Detection of a Protein Mark on Pink Bollworm by ELISA", Entomologia Experimentalis et Applicata, vol. 103, No. 1, 2002, pp. 1-9.
Hagler et al., "Methods for marking insects: current techniques and future prospects", Annu. Rev. Entomol. vol. 46, 2001, pp. 511-543.
Han et al., "Enhancer-Driven Membrane Markers for Analysis of Nonautonomous Mechanisms Reveal Neuron-Glia Interactions in *Drosophila*", Proceedings of the National Academy of Sciences, vol. 108, No. 23, Jun. 7, 2011, pp. 9673-9678.
Handler et al., "A Current Prospective on Insect Gene Transformation", Insect Biochemistry and Molecular Biology, vol. 31, No. 2, 2002, pp. 111-128.
Handler et al., "Germline Transformation of Drosophila Melanogaster with the Piggybac Transooson Vector", Insect Molecular Biology, vol. 8, No. 4, 1999, pp. 449-457.
Handler et al., "Polyubiquitin-Regulated DsRed Marker for Transgenic Insects", Bio Techniques, vol. 31, 2001, pp. 820-828.
Handler et al., "Prospects for Using Genetic Transformation for Improved SIT and New Biocontrol Methods", Genetics, vol. 116, 2002, pp. 137-149.

(56) References Cited

OTHER PUBLICATIONS

Handler et al., "The Lepidopteran Transposon Vector, Piggybac, Mediates Germ-Line Transformation in The Mediterranean Fruit Fly", Proceedings of the National Academy of Sciences, vol. 95, 1998, pp. 7520-7525.
Handler et al., "Use of piggyback Transposon for Germ-Line Transformation of Insects", Insect Biochemistry and Molecular Biology, vol. 32, 2002, pp. 211-1220.
Harris et al., "Field performance of engineered male mosquitoes", Nature Biotechnology , vol. 29 (11), Nov. 2011, pp. 1034-1037.
Hartl et al., "Gene Linkage and Genetic Mapping", in Essential Genetics, Jones and Bartlett Publishers, Sudbury, Massachussetts, 1999, pp. 126-127.
He et al., "The Actin Gene Family in the Oriental Fruit Fly *Bactrocera dorsalis*, Muscle Specific Actins", Insect Biochemistry and Molecular Biology, vol. 24, No. 9, 1994, pp. 891-906.
Heinrich et al., "A Repressible Female-Specific Lethal Genetic System for Making Transgenic Insect Strains Suitable for a Sterile-Release Program", Proceedings of the National Academy of Sciences of the United States of America, vol. 97, Jul. 18, 2000, pp. 8229-8232.
Heslip et al., "Targeted Transposition at the Vestigial Locus of *Drosophila melanogaster*", Genetics, vol. 138, 1994, pp. 1127-1135.
Hiller,"Testis-Specific TAF Homologs Collaborate to Control a Tissue-Specific Transcription Program", Development, vol. 131, 2004, pp. 5297-5308.
Hockemeyer et al., "Genetic Engineering of Human Pluripotent Cells Using TALE Nucleases", Nature Biotechnology, Vo. 28, No. 8, 2011, pp. 731-734.
Hofmann et al., "Rapid Retroviral Delivery of Tetracycline-Inducible Genes in a Single Autoregulatory Cassette", Proceedings of the National Academy of Sciences of the United States of America, vol. 93, 1996, pp. 5185-5190.
Hollenhorst et al., "Expression profiles frame the promoter specificity dilemma of the ETS family of transcription factors", Nucleic Acids Res, vol. 32, No. 18, 2004, pp. 5693-5702.
Honored et al., "Use of Ubiquitin Fusions to Augment Protein Expression in Transgenic Plants", Plant Physiology, vol. 119, 1999, pp. 713-723.
Horn et al., "A Transgene-Based, Embryo-Specific Lethality System for Insect Pest Management", Nature Biotechnology, vol. 1, 2003, pp. 64-70.
Horn et al., "Fluorescent Transformation Markers for Insect Transgenesis", Insect Biochemistry and Molecular Biology, vol. 32, 2002, pp. 1221-1235.
Horn et al., "Highly Sensitive, Fluorescent Transformation Marker for *Drosophila* Transgenesis", Development Genes and Evolution, vol. 210, 2000, pp. 623-629.
Horn,"PiggyBac-Based Insertional Mutagenesis and Enhancer Detection as a Tool for Functional Insect Genomics", Genetics, Vo. 163, 2003, pp. 647-661.
Imai et al., "Control of insecticide resistance in a filed population of houseflies, *Musca domestica*, by releasing susceptible flies", Researches on Population Ecology, vol. 29, 1987, pp. 129-146.
Inoue,"Binding of the *Drosophila* Sex-Lethal Gene Product to the Alternative Splice Site of Transformer Primary Transcript", Nature, vol. 344, 1990, pp. 461-463.
Irvin et al., "Assessing Fitness Costs for Transgenic Aedes Aegypti Expressing the GFP Marker and Transposase Genes", Proceedings of the National Academy of Sciences of the United States of America, vol. 101, No. 3, Jan. 20, 2004, pp. 891-896.
Jagiello et al., "NIPP-1, A Nuclear Inhibitory Subunit of Protein Phosphatase-1, Has RNA-Binding Properties", Journal of Biological Chemistry, vol. 272, No. 35, 1997, pp. 22067-22071.
Jattani et al., "Deficiency Screen Identifies a Novel Role for Beta 2 Tubulin in Salivary Gland and Myoblast Migration in the *Drosophila* Embryo", Developmental Dynamics, vol. 238, No. 4, Apr. 2009, pp. 853-863.
Jiang et al., "Tombola, a Tesmin/TS01-Family Protein, Regulates Transcriptional Activation in the *Drosophila* Male Germline and Physically Interacts with Always Early", Development, vol. 134, No. 8, 2007, pp. 1549-1559.
Jiang et al., "Transcriptional Activation in *Drosophila* Spermatogenesis Involves the Mutually Dependent Function of Aly and a Novel Meiotic Arrest Gene Cookie Monster", Development, vol. 130, No. 3, 2003, pp. 563-573.
Jin et al., "Engineered Female-Specific Lethality for Control of Pest Lepidoptera", ACS Synthetic Biology, American Chemical Society, USA, vol. 2 (3), Jan. 8, 2013, pp. 160-166.
Jin et al., "Mapping of The RNA-Binding and Endoribonuclease Domains of NIPP1, A Nuclear Targeting Subunit of Protein Phosphatase 1", Biochemical Journal, vol. 342, 1999, pp. 13-19.
Johnson-Schlitz et al., "P-Element-Induced Interallelic Gene Conversion of Insertions and Deletions in *Drosophila melanogaster*", Molecular and Cellular Biology, vol. 13, No. 11, 1993, pp. 7006-7018.
Kawase et al., "Gbb/Bmp Signalling Is Essential for Maintaining Germline Stem Cells and for Repressing Barn Franscription in the *Drosophila* Testis", Development, vol. 131, No. 6, 2004, pp. 1365-1375.
Kelly et al., "*Drosophila* MEF2 is a Direct Regulator of Actin57B Transcription in Cardiac, Skeletal, and Visceral Muscle Lineages", Mechanisms of Development, vol. 110, No. 1-2, 2002, pp. 39-50.
Kim et al., "Hybrid Restriction Enzymes: Zinc Finger Fusions to Fok I Cleavage Domain", Proceedings of the National Academy of Sciences of the United States of America, vol. 93, 1996, pp. 1156-1160.
Klassen et al., "Sterile Insect Technique, in: Sterile Insect Technique", Principles and Practice in Area-Wide Integrated Pest Management, The Netherlands, Springer, CURITS et al., 2005, pp. 33-36.
Knipling et al., "Possibilities of Insect Control or Eradication Through the Use of Sexually Sterile Males", Journal of Economic Entomology, vol. 48, 1955, pp. 459-462.
Koukldou et al., "Germ Line Transformation of the Olive Fly Bactrocera Oleae Using a Versatile Transgenesis Marker", Insect Molecular Biology, vol. 15, No. 1, Feb. 2006 pp. 95-103.

C

SEQUENCE LISTING

```
<160> NUMBER OF SEQ ID NOS: 32

<210> SEQ ID NO 1
<211> LENGTH: 10165
<212> TYPE: DNA
<213> ORGANISM: Ceratitis capitata

<400> SEQUENCE: 1

ttaaaatgaa tgtaagcact ttattaacga aatctttggg actaggtcgc taaagggaac      60

aaaagctgga gctcccctgc aggataactt cgtatagcat acattatacg aagttatcct     120

agagcccggg cgaagttcct atactatttg aagaatagga acttcggaat aggaacttct     180

agggaagttc ctatactttc tagagaatag gaacttcgga ataggaactt cttcgaacgg     240

gagtagtgcc ccaactgggg taacctttga gttctctcag ttgggggcgt gaattgccta     300

ggtacggtcc gattgcgggc gccgtttttc ttgaaatatt gctctctctt tctaaatagc     360

gcgaatccgt cgctgtgcat ttaggacatc tcagtcgccg cttggagctc ccaaacgcgc     420

cagtggtagt acacagcact gtgggtgttc agtttgaaat cctcttgctt ctccattgtc     480

tcggttacct ttggtcaaat ccatgggttc tattgcctat atactcttgc gattaccagt     540

gattgcgcta ttagctatta gatggattgt tggccaaact tgtcgcttaa gtggctggga     600

attgtaaccg taggcccgag tgtaatgatc ccccataaaa agttttcgca atgcctttat     660

tttttgttgc aaatctctct ttattctgcg gtattcttca ttattgcggg gatggggaaa     720

gtgtttatat agaagcaact tacgattgaa cccaaatgca cctgacaagc aaggtcaaag     780

ggccagattt ttaaatatat tatttagtct taggactctc tatttgcaat taaattactt     840

tgctacctga gggttaaatc ttccccattg ataataataa ttccactata tgttcaattg     900

ggtttcaccg cgcttagtta catgacgagc cctaatgagc cgtcggtggt ctataaactg     960

tgccttacaa atacttgcaa ctcttctcgt tttgaagtca gcagagttat tgctaattgc    1020

taattgctaa ttgcttttaa ctgatttctt cgaaattggt gctatgttta tggcgctatt    1080

aacaagtatg aatgtcaggt ttaaccaggg gatgcttaat tgtgttctca acttcaaagg    1140

cagaaatgtt tactcttgac catgggttta ggtataatgt tatcaagctc ctcgagttaa    1200

cgttacgtta acgttaacgt tcgaggtcga ctctagacac cggtgttagc cgccgtactc    1260
```

```
atcgatgccc agggcgtcgg tgaacatctg ctcgaactcg aaatcggcca tatccagggc   1320
gccgtagggg gcgctatcgt gcggggtgaa tcccggtccc gggctatcgc catcgcccag   1380
catgtccagg tcgaagtcgt ccagggcatc ggcgtgggcc atcgccacat cctcgccatc   1440
caggtgcagc tcatcgccca ggctcacgtc ggtcggcggg gcggtcgaca ggcggcgggt   1500
gtgtccggcc ggcaggaagc tcaggcgcgg ggcggccagg cccgcctcct ccggggcatc   1560
atcatccggc agatccagca ggccctcgat ggtgctgccg tagttgttct tggtgcgggc   1620
gcggctgtag gcggggcccg agcccgactc gcatttcagt tgcttttcca atccgcagat   1680
aatcagctcc aagccgaaca ggaatgccgg ctcggctcct tgatgatcga acagctcgat   1740
tgcctgacgc agcagtgggg gcatcgaatc ggttgttggg gtctcgcgct cctcttttgc   1800
gacttgatgc tcttggtcct ccagcacgca gcccagggta aagtgaccga cggcgctcag   1860
agcgtagaga gcattttcca ggctgaagcc ttgctggcac aggaacgcga gctggttctc   1920
cagtgtctcg tattgctttt cggtcgggcg cgtgccgaga tggactttgg caccgtctcg   1980
gtgggacagc agagcgcagc ggaacgactt ggcgttattg cggaggaagt cctgccagga   2040
ctcgccttcc aacgggcaaa aatgcgtgtg gtggcggtcg agcatctcga tggccagggc   2100
atccagcagc gcccgcttat tcttcacgtg ccagtagagg gtgggctgct ccacgcccag   2160
cttctgcgcc aacttgcggg tcgtcagtcc ctcaatgcca acttcgttca acagctccaa   2220
cgcggagttg atgactttgg acttatccag gcggctgacc tatagatacc atagatgtat   2280
ggattagtat catatacata caaaggctat ttttgggaca tattaatatt aacaatttcc   2340
gtgatagttt tcaccatttt tgttgaatgt tacgttgaaa atttaaattt gttttaaatt   2400
aattttacca gtcatgtgtt cttaaaagtt tttatgattg aaacggcata aagtggttca   2460
aaaatttatc aagaaaggct ttcctttttt aaatcttatc tttttctctt aaaaatcact   2520
agtcaattca ttattaattt gttaacttga atttggaatg tctatttact ttcagataaa   2580
ttaaagcaag aaacttaata ttcgaaaaaa attgattcta aatggaattt cacttgatct   2640
tcatgtatgc atatcaattt ttatttacat tgtataataa gtttcgagtt gattgttgta   2700
atccacaggt gtcccagaga attaaattcc aaattaccca agtttattga atgttgattg   2760
tagtttcagt tgctttgttg ctgcaacaat ggcttgttga ttgtagatat tttccctttc   2820
cttggtttac ttattacata gactgaaaaa gaggtttact tttttgatac ttatgaaaaa   2880
tttctattag tgattactaa ccaatcgcta tatgtttact agaaaacaaa taaactcttt   2940
acattaacat tcaataatgt ttgctctgta accgacaatt gaaggcgtta cagcaacagt   3000
aatataacta gcttcttaac cctcatctat taaccccatc gtttaaaaca ctatgttaaa   3060
tggtctaaca aatctagata ctaatagatg tcttattact tagcagccac agctgcaaca   3120
tccaagacaa tttttgaaac ttcttattga gctcttggca gcagaaatgt tggtattttt   3180
cacagctttc tgaaagaccg gcaccttcct ccggttcccg tttctgaatt caagaggatt   3240
tccgaccccc aattaatccc gaaacaaata aggtatattc aaaatgatgg aaaagtcatg   3300
gctgctgacc ttatttttat tcctattgat agaatattat tccccttttta aatacactgt   3360
actaagaggt ccggctataa ttttactcac ttgtcgatta tcccatagaa tgttgattgt   3420
agttggttgc ttttccaggt gagagttgat caagtcacaa aagttagcgt gtgttgattg   3480
tagatttgaa ggtaaaataa tttttgcacc cattcatcgg gtaaaacgtt ctccatagaa   3540
tacatttcca tcgataattg ataacttatg aatttcaaag aaaaaaatat gcttttaaaa   3600
ttaccatggt ggctagcgca gattgtttag cttgttcagc tgcgcttgtt tatttgctta   3660
```

```
gctttcgctt agcgacgtgt tcactttgct tgtttgaatt gaattgtcgc tccgtagacg   3720
aagcgcctct atttatactc cggcgctcgt tttcgagttt accactccct atcagtgata   3780
gagaaaagtg aaagtcgagt ttaccactcc ctatcagtga tagagaaaag tgaaagtcga   3840
gtttaccact ccctatcagt gatagagaaa agtgaaagtc gagtttacca ctccctatca   3900
gtgatagaga aaagtgaaag tcgagtttac cactccctat cagtgataga gaaaagtgaa   3960
agtcgagttt accactccct atcagtgata gagaaaagtg aaagtcgagt ttaccactcc   4020
ctatcagtga tagagaaaag tgaaagtcga aacctgcgcg ccgtttaaac tcgcgttaag   4080
atacattgat gagtttggac aaaccacaac tagaatgcag tgaaaaaaat gctttatttg   4140
tgaaatttgt gatgctattg ctttatttgt aaccattata agctgcaata aacaagttaa   4200
caacaacaat tgcattcatt ttatgtttca ggttcagggg gaggtgtggg gaggtttttt   4260
aaagcaagta aaacctctac aaatgtggta tggctgatta tgatcgctct agacaccggt   4320
gctacccgcc atactcatcg atgcccagcg cgtcggtgaa catttgctcg aactcgaagt   4380
cggccatgtc cagggcgccg tacggggcgc tatcgtgggg cgtgaagccc ggtcccgggc   4440
tatctccatc gcccagcata tccaggtcga aatcgtccag ggcgtcggcg tgggccattg   4500
ccacatcctc tccatccagg tgcagctcgt cgcccaggct cacatcggtc ggcggggcgg   4560
tgctcaggcg gcgcgtgtgt ccggcgggca ggaagctcag gcgggggcgg gccaggccgg   4620
cttcctccgg ggcatcgtca tccggcaggt ccagcagtcc ctcgatggtg ctgccatagt   4680
tgttcttggt acgggcgcgg ctgtaggcgc tgccgctctc gcacttcagc tgcttttcca   4740
ggccgcagat gatcagctcc aggccgaaca ggaaggccgg ctcggcgccc tggtgatcga   4800
acagctcgat ggcctggcgc agcagcggcg gcatgctatc ggtggtcggg gtctcgcgct   4860
cctccttggc cacctggtgc tcctgatcct ccagcacaca gcccagggtg aagtggccca   4920
cggcgctcag ggcgtacagg gcgttctcca ggctgaagcc ctgctggcac aggaaggcca   4980
gctggttctc cagggtctcg tactgcttct cggtcgggcg ggtgcccagg tgcaccttgg   5040
cgccatcgcg gtgcgacagc agggcgcagc ggaagctctt ggcgttgttg cgcaggaaat   5100
cctgccagct ctcgccctcc agcgggcaga agtgggtgtg gtggcgatcc agcatttcga   5160
tggccagggc gtccagcagg gcgcgcttgt tcttcacgtg ccagtacagg gtcggctgtt   5220
ccacgcccag cttctgggcc agcttgcggg tggtcaggcc ctcgatgccc acttcgttca   5280
gcagctccag ggcgctgttg atcaccttgc tcttgtccag gcggctgacc tgtgaatacg   5340
gttaatgtca ctattagtga tttataaaaa taaatttgat ttatatatca acaatttttc   5400
atcgcagcct tcagcttttt gttgaataat tataatgata ttttttacga ttcaaatcat   5460
ttaattgtta ctcaacgaaa taagtttaat tcaaatttta aaacaagatt atatattaag   5520
attagaataa gaaagaactt tgttagatta tttaattaaa aagattaaaa tttaagtctc   5580
cagtcactat ttaaagatca tctttcaaac gttaaagtga attcaaacga gacgttcaaa   5640
tttcgattaa acagtaatta actctaaatt tctatcacga attaagttat tgaatatgaa   5700
ggtttatatt tatttacatc atctaatagg tttgagttga ttgttgtaat ccgcatgtgc   5760
cagaagatat caatttccaa attgtccgag ttcatggaat gttgattgtt gtttgtgttg   5820
ctttgtaatt gttgcaggga gtatttatgg tttgttgatt gtagtataag gctgtttcta   5880
aaggctagaa aataatttta tttatttgaa aataagtaaa tatacataat attactaaca   5940
ataggtcgtc ctatttttttg atattctgca caaattttta aaacacaaag attgcaatac   6000
```

```
ttttagacac taatactgca cactctgaaa aattattaaa ttatttttaa aaacttacct   6060
taatacttta gagaaaaata ttataccgca cctttctact ttatactcac tttattatac   6120
cagttgcatg ttgattgtag ttctttgaca agaaaatatt ccatattgct ccaaattatc   6180
ttggtaagtt gattggtgcg tcatttgagc aagctaacac cttgtctcat ttaagttcgc   6240
ctcaagatct catagcattt ttaaatatca ctatatttag taagtaatta gaattaccat   6300
ggtggtttgc tagccgttct atcagatgtg ctccgggaaa cagaaatgtt caactaagtt   6360
ctggcggacg acgcgacacc tttatatact ttgccaagcg cacaggtaga aaggacctat   6420
tttggggatt aaaaaacatc tgcctgtttt attgccatac ccgcgaaaat tcgcgaaatc   6480
cgctacttta cctactgggg ttcctggtaa atgggcgaag aacggcaaag aactggtact   6540
ttccgtcaat aattgtttag aagagagaga acatactccc tatcagtgat agagaagtcc   6600
ctatcagtga tagagatgtc cctatcagtg atagagagtt ccctatcagt gatagagacg   6660
tccctatcag tgatagagaa gtccctatca gtgatagaga gatccctatc agtgatagag   6720
atttccctat cagtgataga gaggtcccta tcagtgatag agacttccct atcagtgata   6780
gagaaatccc tatcagtgat agagacatcc ctatcagtga tagagaactc cctatcagtg   6840
atagagacct ccctatcagt gatagagatc gatgcggccg cgagcgccgg agtataaata   6900
gaggcgcttc gtctacggag cgacaattca attcaaacaa gcaaagtgaa cacgtcgcta   6960
agcgaaagct aagcaaataa acaagcgcag ctgaacaagc taaacaatct gcaggtaccc   7020
tggcggtaag ttgatcaaag gaaacgcaaa gttttcaaga aaaaacaaaa ctaatttgat   7080
ttataacacc tttagaaagc ggggctagcc accatgggca gcgcctacag ccgcgcccgt   7140
accaagaaca actatggcag caccatcgag ggactgctgg acctgccgga tgacgatgcc   7200
ccggaggaag ccggcctggc cgcccccgc ctgagcttcc tgcccgccgg acacacgcgc   7260
cgcctgagca ccgccccgcc gaccgatgtg agcctgggcg acgagctgca cctggatgga   7320
gaggatgtgg caatggccca cgccgacgcc ctggacgatt tcgacctgga tatgctgggc   7380
gatggagata gcccgggacc gggcttcacg ccccacgata gcgccccgta cggcgccctg   7440
gacatggccg acttcgagtt cgagcaaatg ttcaccgacg cgctgggcat cgatgagtat   7500
ggcgggtagg tttaaactcg cgttaagata cattgatgag tttggacaaa ccacaactag   7560
aatgcagtga aaaaaatgct ttatttgtga aatttgtgat gctattgctt tatttgtaac   7620
cattataagc tgcaataaac aagttaacaa caacaattgc attcatttta tgtttcaggt   7680
tcagggggag gtgtgggagg ttttttaaag caagtaaaac ctctacaaat gtggtatggc   7740
tgattatgat cagttatcta gatccggtgg atcttacggg tcctccacct tccgcttttt   7800
cttgggtcga gatctcagga acaggtggtg gcggccctcg gtgcgctcgt actgctccac   7860
gatggtgtag tcctcgttgt gggaggtgat gtccagcttg gcgtccacgt agtagtagcc   7920
gggcagctgc acgggcttct tggccatgta gatggacttg aactccacca ggtagtggcc   7980
gccgtccttc agcttcaggg ccttgtgggt ctcgcccttc agcacgccgt cgcgggggta   8040
caggcgctcg gtggaggcct cccagcccat ggtcttcttc tgcatcacgg ggccgtcgga   8100
ggggaagttc acgccgatga acttcacctt gtagatgaag cagccgtcct gcagggagga   8160
gtcctgggtc acggtcgcca cgccgccgtc ctcgaagttc atcacgcgct cccacttgaa   8220
gccctcgggg aaggacagct tcttgtagtc ggggatgtcg gcggggtgct tcacgtacac   8280
cttggagccg tactggaact ggggggacag gatgtcccag gcgaagggca gggggccgcc   8340
cttggtcacc ttcagcttca cggtgttgtg gccctcgtag ggcggccct cgccctcgcc    8400
```

```
ctcgatctcg aactcgtggc cgttcacggt gccctccatg cgcaccttga agcgcatgaa   8460

ctcggtgatg acgttctcgg aggaggccat ggtggcgacc ggtttgcgct tcttcttggg   8520

tggggtggga tctcccatgg tggcctgaat ctcaacttgc acctgaaggt agtgcagcaa   8580

ggatgagcaa aagggaagaa cccagaaaag aacgggaaaa cttaccccaa ttagaattgt   8640

cttgtcgccg ccagtgtcaa cttgcaactg aaacaatatc caacatgaac gtcaatttat   8700

actgccctaa tggcgaacac gataacaata tttcttttat tatgccctct aaaaccaacg   8760

cggttatcgt ttatttattc aaattagata tagaacatcc gccgacatac aatgttaatg   8820

caaaaacgcg tttggtgagc ggatacgaaa acagtcggcc gataaacatt aatctgaggt   8880

cggtaacacc gtccttgaac ggaacacgag gagcgtacgt gatcagctgc attcgcgcgc   8940

cgcgccttta tcgagattta tttgcataca acaagtacac tgcgccgttg ggatttgtgg   9000

taacgcgcac acatgcagag ctgcaagtgt ggcacatttt gtctgtgcgc aaaacctttg   9060

aagccaaaag tacgaggtcc gttacgggca tgctactagc gcacacggac aatggacccg   9120

acaaattcta cgccaaggat ttaatgataa tgtcgggcaa cgtatccgtt cattttatca   9180

ataacctaca aaaatgtcgc gcgcatcaca aagacatcga tatatttaaa catttatgtc   9240

ccgaactgca aatcgataat agtgttgtgc aacctcgagc gtccgtttga tttaacgtat   9300

agcttgcaaa tgaattattt aattatcaat catgttttac gcgtagaatt ctacccgtaa   9360

agcgagttta gttatgagcc atgtgcaaaa catgacatca gcttttattt ttataacaaa   9420

tgacatcatt tcttgattgt gttttacacg tagaattcta ctcgtaaagc gagttcagtt   9480

ttgaaaaaca aatgacatca tctttttgat tgtgctttac aagtagaatt ctacccgtaa   9540

atcaagttcg gttttgaaaa acaaatgagt catattgtat gatatcatat tgcaaaacaa   9600

atgactcatc aatcgatcgt gcgttacacg tagaattcta ctcgtaaagc gagtttatga   9660

gccgtgtgca aaacatgaca tcatctcgat ttgaaaaaca aatgacatca tccactgatc   9720

gtgcgttaca agtagaattc tactcgtaaa gccagttcgg ttatgagccg tgtgcaaaac   9780

atgacatcag cttatgactc atacttgatt gtgttttacg cgtagaattc tactcgtaaa   9840

gccagttcaa ttttaaaaac aaatgacatc atccaaatta ataaatgaca agcaatgggt   9900

accatgcggc ctggcctcgc gctcgcgcga ctgacggtcg taagcacccg cgtacgtgtc   9960

caccccggtc acaacccctt gtgtcatgtc ggcgacccta cgcccccaac tgagagaact  10020

caaaggttac cccagttggg gcactactcc cgaaaaccgc ttctgacctg ggaaacgtga  10080

agccccgggg catccgctga gggttgccgc cggggcttcg gtgtgtccgt cagtacttaa  10140

tccgcggttg tcctagtcga cttaa                                        10165
```

<210> SEQ ID NO 2
<211> LENGTH: 11301
<212> TYPE: DNA
<213> ORGANISM: Ceratitis capitata

<400> SEQUENCE: 2

```
tgataccaaa agaaaacaat attgacgtaa aaaacgcagc tgcagcgagc tgcaacgagt     60

gacagcaatg atattcctta cataaattca tagaattatt aagataaagt ctttatttca    120

atattaaaga gtccgttata atcgcgactc ttttgaagta caaagacgtt aaataaaaaa    180

ttaatgttcg aatcataatg ttattaatgt ctaaatgcag ttgtacctcg ccgagttttg    240

ttgaatattt aaaaggtctg ctgctactgc aaggtgagaa gcatccattc caggcaatct    300
```

```
gctccattaa ctaaattttc ccttataata tgaggtgctc ttaaaatgaa tgtaagcact    360
ttattaacga aatctttggg actaggtcgc taaagggaac aaaagctgga gctcccctgc    420
aggataactt cgtatagcat acattatacg aagttatcct agagcccggg cgaagttcct    480
atactatttg aagaatagga acttcggaat aggaacttct agggaagttc ctatactttc    540
tagagaatag gaacttcgga ataggaactt cttcgaacgg gagtagtgcc ccaactgggg    600
taacctttga gttctctcag ttgggggcgt gaattgccta ggtacggtcc gattgcgggc    660
gccgtttttc ttgaaatatt gctctctctt tctaaatagc gcgaatccgt cgctgtgcat    720
ttaggacatc tcagtcgccg cttggagctc ccaaacgcgc cagtggtagt acacagcact    780
gtgggtgttc agtttgaaat cctcttgctt ctccattgtc tcggttacct ttggtcaaat    840
ccatgggttc tattgcctat atactcttgc gattaccagt gattgcgcta ttagctatta    900
gatggattgt tggccaaact tgtcgcttaa gtggctggga attgtaaccg taggcccgag    960
tgtaatgatc cccataaaa agttttcgca atgcctttat tttttgttgc aaatctctct   1020
ttattctgcg gtattcttca ttattgcggg gatggggaaa gtgtttatat agaagcaact   1080
tacgattgaa cccaaatgca cctgacaagc aaggtcaaag ggccagattt ttaaatatat   1140
tatttagtct taggactctc tatttgcaat taaattactt tgctacctga gggttaaatc   1200
ttccccattg ataataataa ttccactata tgttcaattg ggtttcaccg cgcttagtta   1260
catgacgagc cctaatgagc cgtcggtggt ctataaactg tgccttacaa atacttgcaa   1320
ctcttctcgt tttgaagtca gcagagttat tgctaattgc taattgctaa ttgcttttaa   1380
ctgatttctt cgaaattggt gctatgttta tggcgctatt aacaagtatg aatgtcaggt   1440
ttaaccaggg gatgcttaat tgtgttctca acttcaaagg cagaaatgtt tactcttgac   1500
catgggttta ggtataatgt tatcaagctc ctcgagttaa cgttacgtta acgttaacgt   1560
tcgaggtcga ctctagacac cggtgttagc cgccgtactc atcgatgccc agggcgtcgg   1620
tgaacatctg ctcgaactcg aaatcggcca tatccagggc gccgtagggg gcgctatcgt   1680
gcggggtgaa tcccggtccc gggctatcgc catcgcccag catgtccagg tcgaagtcgt   1740
ccagggcatc ggcgtgggcc atcgccacat cctcgccatc caggtgcagc tcatcgccca   1800
ggctcacgtc ggtcggcggg gcggtcgaca ggcggcgggt gtgtccggcc ggcaggaagc   1860
tcaggcgcgg ggcggccagg cccgcctcct ccggggcatc atcatccggc agatccagca   1920
ggccctcgat ggtgctgccg tagttgttct tggtgcgggc gcggctgtag gcggggcccg   1980
agcccgactc gcatttcagt tgcttttcca atccgcagat aatcagctcc aagccgaaca   2040
ggaatgccgg ctcggctcct tgatgatcga acagctcgat tgcctgacgc agcagtgggg   2100
gcatcgaatc ggttgttggg gtctcgcgct cctcttttgc gacttgatgc tcttggtcct   2160
ccagcacgca gcccagggta aagtgaccga cggcgctcag agcgtagaga gcattttcca   2220
ggctgaagcc ttgctggcac aggaacgcga gctggttctc cagtgtctcg tattgctttt   2280
cggtcgggcg cgtgccgaga tggactttgg caccgtctcg gtgggacagc agagcgcagc   2340
ggaacgactt ggcgttattg cggaggaagt cctgccagga ctcgccttcc aacgggcaaa   2400
aatgcgtgtg gtggcggtcg agcatctcga tggccagggc atccagcagc gcccgcttat   2460
tcttcacgtg ccagtagagg gtgggctgct ccacgcccag cttctgcgcc aacttgcggg   2520
tcgtcagtcc ctcaatgcca acttcgttca acagctccaa cgcggagttg atgactttgg   2580
acttatccag gcggctgacc tatagatacc atagatgtat ggattagtat catatacata   2640
caaaggctat ttttgggaca tattaatatt aacaatttcc gtgatagttt tcaccatttt   2700
```

```
tgttgaatgt tacgttgaaa atttaaattt gttttaaatt aattttacca gtcatgtgtt   2760
cttaaaagtt tttatgattg aaacggcata aagtggttca aaaatttatc aagaaaggct   2820
ttcctttttt aaatcttatc tttttctctt aaaaatcact agtcaattca ttattaattt   2880
gttaacttga atttggaatg tctatttact ttcagataaa ttaaagcaag aaacttaata   2940
ttcgaaaaaa attgattcta aatggaattt cacttgatct tcatgtatgc atatcaattt   3000
ttatttacat tgtataataa gtttcgagtt gattgttgta atccacaggt gtcccagaga   3060
attaaattcc aaattaccca agtttattga atgttgattg tagtttcagt tgctttgttg   3120
ctgcaacaat ggcttgttga ttgtagatat tttccctttc cttggtttac ttattacata   3180
gactgaaaaa gaggtttact tttttgatac ttatgaaaaa tttctattag tgattactaa   3240
ccaatcgcta tatgtttact agaaaacaaa taaactcttt acattaacat tcaataatgt   3300
ttgctctgta accgacaatt gaaggcgtta cagcaacagt aatataacta gcttcttaac   3360
cctcatctat taaccccatc gtttaaaaca ctatgttaaa tggtctaaca aatctagata   3420
ctaatagatg tcttattact tagcagccac agctgcaaca tccaagacaa tttttgaaac   3480
ttcttattga gctcttggca gcagaaatgt tggtattttt cacagctttc tgaaagaccg   3540
gcaccttcct ccggttcccg tttctgaatt caagaggatt tccgaccccc aattaatccc   3600
gaaacaaata aggtatattc aaaatgatgg aaaagtcatg gctgctgacc ttatttttat   3660
tcctattgat agaatattat tcccctttta aatacactgt actaagaggt ccggctataa   3720
ttttactcac ttgtcgatta tcccatagaa tgttgattgt agttggttgc ttttccaggt   3780
gagagttgat caagtcacaa aagttagcgt gtgttgattg tagatttgaa ggtaaaataa   3840
tttttgcacc cattcatcgg gtaaaacgtt ctccatagaa tacatttcca tcgataattg   3900
ataacttatg aatttcaaag aaaaaaatat gcttttaaaa ttaccatggt ggctagcgca   3960
gattgtttag cttgttcagc tgcgcttgtt tatttgctta gctttcgctt agcgacgtgt   4020
tcactttgct tgtttgaatt gaattgtcgc tccgtagacg aagcgcctct atttatactc   4080
cggcgctcgt tttcgagttt accactccct atcagtgata gagaaaagtg aaagtcgagt   4140
ttaccactcc ctatcagtga tagagaaaag tgaaagtcga gtttaccact ccctatcagt   4200
gatagagaaa agtgaaagtc gagtttacca ctccctatca gtgatagaga aaagtgaaag   4260
tcgagtttac cactccctat cagtgataga gaaaagtgaa agtcgagttt accactccct   4320
atcagtgata gagaaaagtg aaagtcgagt ttaccactcc ctatcagtga tagagaaaag   4380
tgaaagtcga aacctgcgcg ccgtttaaac tcgcgttaag atacattgat gagtttggac   4440
aaaccacaac tagaatgcag tgaaaaaaat gctttatttg tgaaatttgt gatgctattg   4500
ctttatttgt aaccattata agctgcaata aacaagttaa caacaacaat tgcattcatt   4560
ttatgtttca ggttcagggg gaggtgtggg gaggtttttt aaagcaagta aaacctctac   4620
aaatgtggta tggctgatta tgatcgctct agacaccggt gctacccgcc atactcatcg   4680
atgcccagcg cgtcggtgaa catttgctcg aactcgaagt cggccatgtc cagggcgccg   4740
tacggggcgc tatcgtgggg cgtgaagccc ggtcccgggc tatctccatc gcccagcata   4800
tccaggtcga aatcgtccag ggcgtcggcg tgggccattg ccacatcctc tccatccagg   4860
tgcagctcgt cgcccaggct cacatcggtc ggcggggcgg tgctcaggcg gcgcgtgtgt   4920
ccggcgggca ggaagctcag gcggggggcg gccaggccgg cttcctccgg ggcatcgtca   4980
tccggcaggt ccagcagtcc ctcgatggtg ctgccatagt tgttcttggt acgggcgcgg   5040
```

```
ctgtaggcgc tgccgctctc gcacttcagc tgcttttcca ggccgcagat gatcagctcc   5100
aggccgaaca ggaaggccgg ctcggcgccc tggtgatcga acagctcgat ggcctggcgc   5160
agcagcggcg gcatgctatc ggtggtcggg gtctcgcgct cctccttggc cacctggtgc   5220
tcctgatcct ccagcacaca gcccagggtg aagtggccca cggcgctcag ggcgtacagg   5280
gcgttctcca ggctgaagcc ctgctggcac aggaaggcca gctggttctc cagggtctcg   5340
tactgcttct cggtcgggcg ggtgcccagg tgcaccttgg cgccatcgcg gtgcgacagc   5400
agggcgcagc ggaagctctt ggcgttgttg cgcaggaaat cctgccagct ctcgccctcc   5460
agcgggcaga agtgggtgtg gtggcgatcc agcatttcga tggccagggc gtccagcagg   5520
gcgcgcttgt tcttcacgtg ccagtacagg gtcggctgtt ccacgcccag cttctgggcc   5580
agcttgcggg tggtcaggcc ctcgatgccc acttcgttca gcagctccag ggcgctgttg   5640
atcaccttgc tcttgtccag gcggctgacc tgtgaatacg gttaatgtca ctattagtga   5700
tttataaaaa taaatttgat ttatatatca acaatttttc atcgcagcct tcagcttttt   5760
gttgaataat tataatgata ttttttacga ttcaaatcat ttaattgtta ctcaacgaaa   5820
taagtttaat tcaaatttta aaacaagatt atatattaag attagaataa gaaagaactt   5880
tgttagatta tttaattaaa aagattaaaa tttaagtctc cagtcactat ttaaagatca   5940
tctttcaaac gttaaagtga attcaaacga gacgttcaaa tttcgattaa acagtaatta   6000
actctaaatt tctatcacga attaagttat tgaatatgaa ggtttatatt tatttacatc   6060
atctaatagg tttgagttga ttgttgtaat ccgcatgtgc cagaagatat caatttccaa   6120
attgtccgag ttcatggaat gttgattgtt gtttgtgttg ctttgtaatt gttgcaggga   6180
gtatttatgg tttgttgatt gtagtataag gctgtttcta aaggctagaa aataatttta   6240
tttatttgaa aataagtaaa tatacataat attactaaca ataggtcgtc ctattttttg   6300
atattctgca caaattttta aaacacaaag attgcaatac ttttagacac taatactgca   6360
cactctgaaa aattattaaa ttatttttaa aaacttacct taatacttta gagaaaaata   6420
ttataccgca cctttctact ttatactcac tttattatac cagttgcatg ttgattgtag   6480
ttctttgaca agaaaatatt ccatattgct ccaaattatc ttggtaagtt gattggtgcg   6540
tcatttgagc aagctaacac cttgtctcat ttaagttcgc ctcaagatct catagcattt   6600
ttaaatatca ctatatttag taagtaatta gaattaccat ggtggtttgc tagccgttct   6660
atcagatgtg ctccgggaaa cagaaatgtt caactaagtt ctggcggacg acgcgacacc   6720
tttatatact ttgccaagcg cacaggtaga aaggacctat tttggggatt aaaaaacatc   6780
tgcctgtttt attgccatac ccgcgaaaat tcgcgaaatc cgctacttta cctactgggg   6840
ttcctggtaa atgggcgaag aacggcaaag aactggtact ttccgtcaat aattgtttag   6900
aagagagaga acatactccc tatcagtgat agagaagtcc ctatcagtga tagagatgtc   6960
cctatcagtg atagagagtt ccctatcagt gatagagacg tccctatcag tgatagagaa   7020
gtccctatca gtgatagaga gatccctatc agtgatagag atttccctat cagtgataga   7080
gaggtcccta tcagtgatag agacttccct atcagtgata gagaaatccc tatcagtgat   7140
agagacatcc ctatcagtga tagagaactc cctatcagtg atagagacct ccctatcagt   7200
gatagagatc gatgcggccg cgagcgccgg agtataaata gaggcgcttc gtctacggag   7260
cgacaattca attcaaacaa gcaaagtgaa cacgtcgcta agcgaaagct aagcaaataa   7320
acaagcgcag ctgaacaagc taaacaatct gcaggtaccc tggcggtaag ttgatcaaag   7380
gaaacgcaaa gttttcaaga aaaaacaaaa ctaatttgat ttataacacc tttagaaagc   7440
```

-continued

```
gggggctagcc accatgggca gcgcctacag ccgcgcccgt accaagaaca actatggcag   7500
caccatcgag ggactgctgg acctgccgga tgacgatgcc ccggaggaag ccggcctggc   7560
cgccccccgc ctgagcttcc tgcccgccgg acacacgcgc cgcctgagca ccgccccgcc   7620
gaccgatgtg agcctgggcg acgagctgca cctggatgga gaggatgtgg caatggccca   7680
cgccgacgcc ctggacgatt tcgacctgga tatgctgggc gatggagata gcccgggacc   7740
gggcttcacg ccccacgata gcgccccgta cggcgccctg gacatggccg acttcgagtt   7800
cgagcaaatg ttcaccgacg cgctgggcat cgatgagtat ggcgggtagg tttaaactcg   7860
cgttaagata cattgatgag tttggacaaa ccacaactag aatgcagtga aaaaaatgct   7920
ttatttgtga aatttgtgat gctattgctt tatttgtaac cattataagc tgcaataaac   7980
aagttaacaa caacaattgc attcatttta tgtttcaggt tcaggggggag gtgtgggagg   8040
tttttttaaag caagtaaaac ctctacaaat gtggtatggc tgattatgat cagttatcta   8100
gatccggtgg atcttacggg tcctccacct tccgcttttt cttgggtcga gatctcagga   8160
acaggtggtg gcggccctcg gtgcgctcgt actgctccac gatggtgtag tcctcgttgt   8220
gggaggtgat gtccagcttg gcgtccacgt agtagtagcc gggcagctgc acgggcttct   8280
tggccatgta gatggacttg aactccacca ggtagtggcc gccgtccttc agcttcaggg   8340
ccttgtgggt ctcgcccttc agcacgccgt cgcgggggta caggcgctcg gtggaggcct   8400
cccagcccat ggtcttcttc tgcatcacgg ggccgtcgga ggggaagttc acgccgatga   8460
acttcacctt gtagatgaag cagccgtcct gcagggagga gtcctgggtc acggtcgcca   8520
cgccgccgtc ctcgaagttc atcacgcgct cccacttgaa gccctcgggg aaggacagct   8580
tcttgtagtc ggggatgtcg gcggggtgct tcacgtacac cttggagccg tactggaact   8640
gggggggacag gatgtcccag gcgaagggca gggggccgcc cttggtcacc ttcagcttca   8700
cggtgttgtg gccctcgtag ggcggccct cgccctcgcc ctcgatctcg aactcgtggc   8760
cgttcacggt gccctccatg cgcaccttga agcgcatgaa ctcggtgatg acgttctcgg   8820
aggaggccat ggtggcgacc ggtttgcgct tcttcttggg tggggtggga tctcccatgg   8880
tggcctgaat ctcaacttgc acctgaaggt agtgcagcaa ggatgagcaa aagggaagaa   8940
cccagaaaag aacgggaaaa cttaccccaa ttagaattgt cttgtcgccg ccagtgtcaa   9000
cttgcaactg aaacaatatc caacatgaac gtcaatttat actgccctaa tggcgaacac   9060
gataacaata tttcttttat tatgccctct aaaaccaacg cggttatcgt ttatttattc   9120
aaattagata tagaacatcc gccgacatac aatgttaatg caaaaacgcg tttggtgagc   9180
ggatacgaaa acagtcggcc gataaacatt aatctgaggt cggtaacacc gtccttgaac   9240
ggaacacgag gagcgtacgt gatcagctgc attcgcgcgc cgcgccttta tcgagattta   9300
tttgcataca acaagtacac tgcgccgttg ggatttgtgg taacgcgcac acatgcagag   9360
ctgcaagtgt ggcacatttt gtctgtgcgc aaaacctttg aagccaaaag tacgaggtcc   9420
gttacgggca tgctactagc gcacacggac aatggacccg acaaattcta cgccaaggat   9480
ttaatgataa tgtcgggcaa cgtatccgtt cattttatca ataacctaca aaaatgtcgc   9540
gcgcatcaca aagacatcga tatatttaaa catttatgtc ccgaactgca aatcgataat   9600
agtgttgtgc aacctcgagc gtccgtttga tttaacgtat agcttgcaaa tgaattattt   9660
aattatcaat catgttttac gcgtagaatt ctacccgtaa agcgagttta gttatgagcc   9720
atgtgcaaaa catgacatca gcttttattt ttataacaaa tgacatcatt tcttgattgt   9780
```

gttttacacg tagaattcta ctcgtaaagc gagttcagtt ttgaaaaaca aatgacatca 9840
tctttttgat tgtgctttac aagtagaatt ctacccgtaa atcaagttcg gttttgaaaa 9900
acaaatgagt catattgtat gatatcatat tgcaaaacaa atgactcatc aatcgatcgt 9960
gcgttacacg tagaattcta ctcgtaaagc gagtttatga gccgtgtgca aaacatgaca 10020
tcatctcgat ttgaaaaaca aatgacatca tccactgatc gtgcgttaca agtagaattc 10080
tactcgtaaa gccagttcgg ttatgagccg tgtgcaaaac atgacatcag cttatgactc 10140
atacttgatt gtgttttacg cgtagaattc tactcgtaaa gccagttcaa ttttaaaaac 10200
aaatgacatc atccaaatta ataaatgaca agcaatgggt accatgcggc ctggcctcgc 10260
gctcgcgcga ctgacggtcg taagcacccg cgtacgtgtc caccccggtc acaacccctt 10320
gtgtcatgtc ggcgacccta cgcccccaac tgagagaact caaaggttac cccagttggg 10380
gcactactcc cgaaaaccgc ttctgacctg ggaaacgtga agccccgggg catccgctga 10440
gggttgccgc cggggcttcg gtgtgtccgt cagtacttaa tccgcggttg tcctagtcga 10500
cttaaataaa aataatgtaa agacagcttg tatgggaaca ttatttatat tttccatttt 10560
tttacgttct ctgttatctg ctacggagaa accgatataa aatggcgttc tactcgaaaa 10620
taagaacata aataaaacgg ataagccgtt caactgcatt cttcttcaat ttgtatgtac 10680
cctgaagaga aagatatgca aaaaaaaaag gttgattatg ctagttctta cattttggaa 10740
ctcgtgcaaa taagttgctt ttcggtgaaa tggctaaaat ataattcaga tcaaaaaaat 10800
aagtaatata atgtgtgaaa acaatactta gcgcaaaaaa ctagccgtcc gtcgtcggcc 10860
gttgttgcta agaatttatg atgaaataaa tcatcacaaa ccttagcaat gggcagcttg 10920
catttgtttg cgcatccata aatttgccga tgcattttgg aacatgattc atcgttaaag 10980
tttgcacagt tgcatttagg aaagtgtgac aactgtataa atggttactt tgcaactgac 11040
gttttggaac tcacccttta gtattgtatg ttttacacta tgattcaata attaaaggtt 11100
ggataatggg aagtagagga tacaggctcc gcttgaatgg taagttaacc attgaccaaa 11160
tattcaccat gcggcaaatt ttggtaaaga cacatgaaaa ggtcgcattc gacgccacga 11220
ataggagata actttacgcc gctatgaatt tggtatccca gcaaaactta tacgactatg 11280
taaactgacg ttaagcaaca c 11301

<210> SEQ ID NO 3
<211> LENGTH: 11211
<212> TYPE: DNA
<213> ORGANISM: Ceratitis capitata

<400> SEQUENCE: 3
tgctgagctg caggttatgc ggtaaagtat ttaatttcag ctcaggcttg agccatcact 60
acaaagtggc acataactta aaaaaatcac tttcgaaagt gaaatcagaa gagtccgttc 120
taatgcctga ggagcttaaa acagaaataa tcgatatgaa aacggaaaaa gtagagaatg 180
acgaagaatt ttgtaatata attaaaagta atgaggaaat tagccaaaag gaagaggagg 240
ccaagcgagt aattgtggaa ctgatacaaa atgcaacata tacatcattc tttccggaaa 300
actttaatag ctctatagat tctggtccgc caatagcacg cgaagaaaca atatcagcag 360
taaacagcat tgttagtgag gaaacctcct gaattttaat ctatattcta tttaagtgtg 420
ttatgtactc ggtattaatg taataataat tgtagaatta taattaacaa aatgtgaaat 480
attatttata taatatgata tttatataga tactgaatgc atctatgtat atatgtacat 540
acatttaagt cgactaggac aaccgcggat taagtactga cggacacacc gaagccccgg 600

```
cggcaaccct cagcggatgc cccggggctt cacgttttcc caggtcagaa gcggttttcg    660
ggagtagtgc cccaactggg gtaacctttg agttctctca gttgggggcg tagggtcgcc    720
gacatgacac aaggggttgt gaccggggtg gacacgtacg cgggtgctta cgaccgtcag    780
tcgcgcgagc gcgataactc gcgttaagat acattgatga gtttggacaa accacaacta    840
gaatgcagtg aaaaaaatgc tttatttgtg aaatttgtga tgctattgct ttatttgtaa    900
ccattataag ctgcaataaa caagttaaca acaacaattg cattcatttt atgtttcagg    960
ttcaggggga ggtgtgggag gtttttttaaa gcaagtaaaa cctctacaaa tgtggtatgg   1020
ctgattatga tcagttatct agatccggtg gatcttacgg gtcctccacc ttccgctttt   1080
tcttgggtcg agatctcagg aacaggtggt ggcggccctc ggtgcgctcg tactgctcca   1140
cgatggtgta gtcctcgttg tgggaggtga tgtccagctt ggcgtccacg tagtagtagc   1200
cgggcagctg cacgggcttc ttggccatgt agatggactt gaactccacc aggtagtggc   1260
cgccgtcctt cagcttcagg gccttgtggg tctcgccctt cagcacgccg tcgcgggggt   1320
acaggcgctc ggtggaggcc tcccagccca tggtcttctt ctgcatcacg gggccgtcgg   1380
aggggaagtt cacgccgatg aacttcacct tgtagatgaa gcagccgtcc tgcagggagg   1440
agtcctgggt cacggtcgcc acgccgccgt cctcgaagtt catcacgcgc tcccacttga   1500
agccctcggg gaaggacagc ttcttgtagt cggggatgtc ggcggggtgc ttcacgtaca   1560
ccttggagcc gtactggaac tgggggggaca ggatgtccca ggcgaagggc agggggccgc   1620
ccttggtcac cttcagcttc acggtgttgt ggccctcgta ggggcggccc tcgccctcgc   1680
cctcgatctc gaactcgtgg ccgttcacgg tgccctccat gcgcaccttg aagcgcatga   1740
actcggtgat gacgttctcg gaggaggcca tggtggcgac cggtttgcgc ttcttcttgg   1800
gtggggtggg atccccgatc tgcattttgg attattctgc gggtcaaaat agagatgtgg   1860
aaaattagta cgaaatcaaa tgagtttcgt tgaaattaca aaactattga aactaacttc   1920
ctggctgggg aataaaaatg ggaaacttat ttatcgacgc caactttgtt gagaaacccc   1980
tattaaccct ctacgaatat tggaacaaag gaaagcgaag aaacaggaac aaaggtagtt   2040
gagaaacctg ttccgttgct cgtcatcgtt ttcataatgc gagtgtgtgc atgtatatat   2100
acacagctga aacgcatgca tacacattat tttgtgtgta tatggtgacg tcacaactac   2160
taagcaataa gaaattttcc agacgtggct ttcgtttcaa gcaacctact ctatttcagc   2220
taaaaataag tggatttcgt tggtaaaata cttcaattaa gcaaagaact aactaactaa   2280
taacatgcac acaaatgctc gagtgcgttc gtgatttctc gaattttcaa atgcgtcact   2340
gcgaatttca caatttgcca ataaatcttg gcgaaaatca acacgcaagt tttatttata   2400
gatttgtttg cgttttgatg ccaattgatt gggaaaacaa gatgcgtggc tgccaatttc   2460
ttattttgta attacgtaga gcgttgaata aaaaaaaaat ggccgaacaa agaccttgaa   2520
atgcagtttt tcttgaaatt actcaacgtc ttgttgctct tattactaat tggtaacagc   2580
gagttaaaaa cttacgtttc ttgtgacttt cgagaatgtt cttttaattg tactttaatc   2640
accaacaatt aagtataaat ttttcgctga ttgcgcttta ctttctgctt gtacttgctg   2700
ctgcaaatgt caattggttt tgaaggcgac cgttcgcgaa cgctgtttat ataccttcgg   2760
tgtccgttga aaatcactaa aaaataccgt agtgttcgta acactttagt acagagaaaa   2820
aaaattgtgc cgaaatgttt ttgatacgta cgaatacctt gtattaaaat tttttatgat   2880
ttctgtgtat cacttttttt ttgtgttttt cgtttaaact caccacagta caaaacaata   2940
```

```
aaatattttt aagacaattt caaattgaga cctttctcgt actgacttga ccggctgaat   3000
gaggatttct acctagacga cctacttctt accatgacat tgaatgcaat gccacctttg   3060
atctaaactt acaaaagtcc aaggcttgtt aggattggtg tttatttagt ttgcttttga   3120
aatagcactg tcttctctac cggctataat tttgaaactc gcagcttgac tggaaattta   3180
aaaagtaatt ctgtgtaggt aaagggtgtt ttaaaagtgt gatgtgttga gcgttgcggc   3240
aacgactgct atttatgtat atattttcaa aacttattgt ttttgaagtg ttttaaatgg   3300
agctatctgg caacgctgcg cataatctta cacaagcttt tcttaatcca tttttaagtg   3360
aaatttgttt ttactctttc ggcaaataat tgttaaatcg ctttaagtgg gcttacatct   3420
ggataagtaa tgaaaacctg catattataa tattaaaaca tataatccac tgtgctttcc   3480
ccgtgtgtgg ccatatacct aaaaaagttt attttcgcag agccccgcac ggtcacacta   3540
cggttcggcg attttcgatt ttggacagta ctgattgcaa gcgcaccgaa agcaaaatgg   3600
agctggagat tttgaacgcg aagaacagca agccgtacgg caaggtgaag gtgccctccg   3660
gcgccacgcc catcggcgat ctgcgcgccc taattcacaa gaccctgaag cagaccccac   3720
acgcgaatcg ccagtcgctt cgtctggaac tgaagggcaa aagcctgaaa gatacggaca   3780
cattggaatc tctgtcgctg cgttccggcg acaagatcgg ggtaccatgc ggccgcatcg   3840
atctctatca ctgataggga ggtctctatc actgataggg agttctctat cactgatagg   3900
gatgtctcta tcactgatag ggatttctct atcactgata gggaagtctc tatcactgat   3960
agggacctct ctatcactga tagggaaatc tctatcactg atagggatct ctctatcact   4020
gatagggact tctctatcac tgatagggac gtctctatca ctgataggga actctctatc   4080
actgataggg acatctctat cactgatagg gacttctcta tcactgatag ggagtatgtt   4140
ctctctcttc taaacaatta ttgacggaaa gtaccagttc tttgccgttc ttcgcccatt   4200
ttccaggaac cccagtaggt aaagtagcgg atttcgcgaa ttttcgcggg tatggcaata   4260
aaacaggcag atgtttttta atccccaaaa taggtccttt ctacctgtgc gcttggcaaa   4320
gtatataaag gtgttgcgtc gtccgccaga acttagttga acatttctgt ttcccggagc   4380
acatctgata gaacggctag caaaccacca tggtaattct aattacttac taaatatagt   4440
gatatttaaa aatgctatga gatcttgagg cgaacttaaa tgagacaagg tgttagcttg   4500
ctcaaatgac gcaccaatca acttaccaag ataatttgga gcaatatgga atattttctt   4560
gtcaaagaac tacaatcaac atgcaactgg tataataaag tgagtataaa gtagaaaggt   4620
gcggtataat atttttctct aaagtattaa ggtaagtttt taaaaataat ttaataattt   4680
ttcagagtgt gcagtattag tgtctaaaag tattgcaatc tttgtgtttt aaaaatttgt   4740
gcagaatatc aaaaaatagg acgacctatt gttagtaata ttatgtatat ttacttattt   4800
tcaaataaat aaaattattt tctagccttt agaaacagcc ttatactaca atcaacaaac   4860
cataaatact ccctgcaaca attacaaagc aacacaaaca acaatcaaca ttccatgaac   4920
tcggacaatt tggaaattga tatcttctgg cacatgcgga ttacaacaat caactcaaac   4980
ctattagatg atgtaaataa atataaacct tcatattcaa taacttaatt cgtgatagaa   5040
atttagagtt aattactgtt taatcgaaat ttgaacgtct cgtttgaatt cactttaacg   5100
tttgaaagat gatctttaaa tagtgactgg agacttaaat tttaatcttt ttaattaaat   5160
aatctaacaa agttctttct tattctaatc ttaatatata atcttgtttt aaaatttgaa   5220
ttaaacttat ttcgttgagt aacaattaaa tgatttgaat cgtaaaaaat atcattataa   5280
ttattcaaca aaaagctgaa ggctgcgatg aaaaattgtt gatatataaa tcaaatttat   5340
```

```
ttttataaat cactaatagt gacattaacc gtattcacag gtcagccgcc tggacaagag   5400
caaggtgatc aacagcgccc tggagctgct gaacgaagtt ggtatcgagg gcctgaccac   5460
ccgcaagctg gcccagaagc tgggcgtgga acagccgacc ctgtactggc acgtgaagaa   5520
caagcgcgcc ctgctggacg ccctggccat cgaaatgctg gatcgccacc acacccactt   5580
ctgcccgctg gagggcgaga gctggcagga tttcctgcgc aacaacgcca agagcttccg   5640
ctgcgccctg ctgtcgcacc gcgatggcgc caaggtgcac ctgggcaccc gcccgaccga   5700
gaagcagtac gagaccctgg agaaccagct ggccttcctg tgccagcagg gcttcagcct   5760
ggagaacgcc ctgtacgccc tgagcgccgt gggccacttc accctgggct gtgtgctgga   5820
ggatcaggag caccaggtgg ccaaggagga gcgcgagacc ccgaccaccg atagcatgcc   5880
gccgctgctg cgccaggcca tcgagctgtt cgatcaccag ggcgccgagc cggccttcct   5940
gttcggcctg gagctgatca tctgcggcct ggaaaagcag ctgaagtgcg agagcggcag   6000
cgcctacagc cgcgcccgta ccaagaacaa ctatggcagc accatcgagg gactgctgga   6060
cctgccggat gacgatgccc cggaggaagc cggcctggcc gccccccgcc tgagcttcct   6120
gcccgccgga cacacgcgcc gcctgagcac cgccccgccg accgatgtga gcctgggcga   6180
cgagctgcac ctggatggag aggatgtggc aatggcccac gccgacgccc tggacgattt   6240
cgacctggat atgctgggcg atggagatag cccgggaccg ggcttcacgc cccacgatag   6300
cgccccgtac ggcgccctgg acatggccga cttcgagttc gagcaaatgt tcaccgacgc   6360
gctgggcatc gatgagtatg gcgggtagca ccggtgtcta gagcgatcat aatcagccat   6420
accacatttg tagaggtttt acttgcttta aaaaacctcc cacacctccc cctgaacctg   6480
aaacataaaa tgaatgcaat tgttgttgtt aacttgttta ttgcagctta taatggttac   6540
aaataaagca atagcatcac aaatttcaca aataaagcat ttttttcact gcattctagt   6600
tgtggtttgt ccaaactcat caatgtatct taacgcgagt ttaaacggcg cgcaggtttc   6660
gactttcact tttctctatc actgataggg agtggtaaac tcgactttca cttttctcta   6720
tcactgatag ggagtggtaa actcgacttt cacttttctc tatcactgat agggagtggt   6780
aaactcgact ttcacttttc tctatcactg atagggagtg gtaaactcga ctttcacttt   6840
tctctatcac tgatagggag tggtaaactc gactttcact tttctctatc actgataggg   6900
agtggtaaac tcgactttca cttttctcta tcactgatag ggagtggtaa actcgaaaac   6960
gagcgccgga gtataaatag aggcgcttcg tctacggagc gacaattcaa ttcaaacaag   7020
caaagtgaac acgtcgctaa gcgaaagcta agcaaataaa caagcgcagc tgaacaagct   7080
aaacaatctg cgctagccac catggtaatt ttaaaagcat atttttttct ttgaaattca   7140
taagttatca attatcgatg gaaatgtatt ctatggagaa cgttttaccc gatgaatggg   7200
tgcaaaaatt attttacctt caaatctaca atcaacacac gctaactttt gtgacttgat   7260
caactctcac ctggaaaagc aaccaactac aatcaacatt ctatgggata atcgacaagt   7320
gagtaaaatt atagccggac ctcttagtac agtgtattta aaaggggaat aatattctat   7380
caataggaat aaaaataagg tcagcagcca tgacttttcc atcattttga atataccta    7440
tttgtttcgg gattaattgg gggtcggaaa tcctcttgaa ttcagaaacg ggaaccggag   7500
gaaggtgccg gtctttcaga aagctgtgaa aaataccaac atttctgctg ccaagagctc   7560
aataagaagt ttcaaaaatt gtcttggatg ttgcagctgt ggctgctaag taataagaca   7620
tctattagta tctagatttg ttagaccatt taacatagtg ttttaaacga tggggttaat   7680
```

```
agatgagggt taagaagcta gttatattac tgttgctgta acgccttcaa ttgtcggtta   7740
cagagcaaac attattgaat gttaatgtaa agagtttatt tgttttctag taaacatata   7800
gcgattggtt agtaatcact aatagaaatt tttcataagt atcaaaaaag taaacctctt   7860
tttcagtcta tgtaataagt aaaccaagga aagggaaaat atctacaatc aacaagccat   7920
tgttgcagca acaaagcaac tgaaactaca atcaacattc aataaacttg ggtaatttgg   7980
aatttaattc tctgggacac ctgtggatta caacaatcaa ctcgaaactt attatacaat   8040
gtaaataaaa attgatatgc atacatgaag atcaagtgaa attccattta gaatcaattt   8100
ttttcgaata ttaagtttct tgctttaatt tatctgaaag taaatagaca ttccaaattc   8160
aagttaacaa attaataatg aattgactag tgatttttaa gagaaaaaga taagatttaa   8220
aaaaggaaag cctttcttga taaatttttg aaccacttta tgccgtttca atcataaaaa   8280
cttttaagaa cacatgactg gtaaaattaa tttaaaacaa atttaaattt tcaacgtaac   8340
attcaacaaa aatggtgaaa actatcacgg aaattgttaa tattaatatg tcccaaaaat   8400
agcctttgta tgtatatgat actaatccat acatctatgg tatctatagg tcagccgcct   8460
ggataagtcc aaagtcatca actccgcgtt ggagctgttg aacgaagttg gcattgaggg   8520
actgacgacc cgcaagttgg cgcagaagct gggcgtggag cagcccaccc tctactggca   8580
cgtgaagaat aagcgggcgc tgctggatgc cctggccatc gagatgctcg accgccacca   8640
cacgcatttt tgcccgttgg aaggcgagtc ctggcaggac ttcctccgca ataacgccaa   8700
gtcgttccgc tgcgctctgc tgtcccaccg agacggtgcc aaagtccatc tcggcacgcg   8760
cccgaccgaa aagcaatacg agacactgga gaaccagctc gcgttcctgt gccagcaagg   8820
cttcagcctg gaaaatgctc tctacgctct gagcgccgtc ggtcacttta ccctgggctg   8880
cgtgctggag gaccaagagc atcaagtcgc aaaagaggag cgcgagaccc caacaaccga   8940
ttcgatgccc ccactgctgc gtcaggcaat cgagctgttc gatcatcaag gagccgagcc   9000
ggcattcctg ttcggcttgg agctgattat ctgcggattg gaaaagcaac tgaaatgcga   9060
gtcgggctcg ggccccgcct acagccgcgc ccgcaccaag aacaactacg gcagcaccat   9120
cgagggcctg ctggatctgc cggatgatga tgccccggag gaggcgggcc tggccgcccc   9180
gcgcctgagc ttcctgccgg ccggacacac ccgccgcctg tcgaccgccc cgccgaccga   9240
cgtgagcctg ggcgatgagc tgcacctgga tggcgaggat gtggcgatgg cccacgccga   9300
tgccctggac gacttcgacc tggacatgct gggcgatggc gatagcccgg gaccgggatt   9360
caccccgcac gatagcgccc cctacggcgc cctggatatg gccgatttcg agttcgagca   9420
gatgttcacc gacgccctgg gcatcgatga gtacggcggc taacaccggt gtctagagtc   9480
gacctcgaac gttaacgtta acgtaacgtt aactcgagga gcttgataac attataccta   9540
aacccatggt caagagtaaa catttctgcc tttgaagttg agaacacaat taagcatccc   9600
ctggttaaac ctgacattca tacttgttaa tagcgccata aacatagcac caatttcgaa   9660
gaaatcagtt aaaagcaatt agcaattagc aattagcaat aactctgctg acttcaaaac   9720
gagaagagtt gcaagtattt gtaaggcaca gtttatagac caccgacggc tcattagggc   9780
tcgtcatgta actaagcgcg gtgaaaccca attgaacata tagtggaatt attattatca   9840
atggggaaga tttaaccctc aggtagcaaa gtaatttaat tgcaaataga gagtcctaag   9900
actaaataat atatttaaaa atctggccct ttgaccttgc ttgtcaggtg catttgggtt   9960
caatcgtaag ttgcttctat ataaacactt tccccatccc cgcaataatg aagaataccg  10020
cagaataaag agagatttgc aacaaaaaat aaaggcattg cgaaaacttt ttatggggga  10080
```

```
tcattacact cgggcctacg gttacaattc ccagccactt aagcgacaag tttggccaac  10140

aatccatcta atagctaata gcgcaatcac tggtaatcgc aagagtatat aggcaataga  10200

acccatggat ttgaccaaag gtaaccgaga caatggagaa gcaagaggat ttcaaactga  10260

acacccacag tactgtgtac taccactggc gcgtttggga gctccaagcg gcgactgaga  10320

tgtcctaaat gcacagcgac ggattcgcgc tatttagaaa gagagagcaa tatttcaaga  10380

aaaacggccg cccgcaatcg gaccgtacct aggcaattca cgcccccaac tgagagaact  10440

caaaggttac cccagttggg gcactactcc cgttcgaaga agttcctatt ccgaagttcc  10500

tattctctag aaagtatagg aacttcccta gaagttccta ttccgaagtt cctattcttc  10560

aaatagtata ggaacttcgc ccgggctcta ggataacttc gtataatgta tgctatacga  10620

agttatcctg caggggagct ccagcttttg ttccctttag cgacctagtc ccaaagattt  10680

cgttaataaa gtgcttacat tcattttaat catttctgtt attagaaaaa gaattatgct  10740

gattcgtaat tttttatttg cctttatagc aaatttcttg tgaaaaaatc ggttgaagtt  10800

ttaattatga aaaagtacca agttctttaa aaatttgtta atatgtatta aatctataat  10860

ccaaattttt tcatttataa tttaggatag ttaattttag aatattaaaa ataatttaca  10920

ttgttagaaa aattctgtct gccacattca tgttatttat tggcaactct aaaaatttat  10980

tgtcaaaatt gtcaatctac catctcgaat tcgttggcat cggcaaataa cacgctgcaa  11040

ctaaatattt attcagtttt atttaatccg caaaaatgca tcccgatctt actgagcgca  11100

tattgcaaca tttagaagga gttgacaagg tgaacactat tgatttagcc acactatttg  11160

gtgttggtca ccaaaaaatt gtgggagcat taaaaagtat tgaagcccat g          11211
```

<210> SEQ ID NO 4
<211> LENGTH: 23
<212> TYPE: DNA
<213> ORGANISM: Ceratitis capitata

<400> SEQUENCE: 4

```
gctgcccatt gctaaggttt gtg                                           23
```

<210> SEQ ID NO 5
<211> LENGTH: 21
<212> TYPE: DNA
<213> ORGANISM: Ceratitis capitata

<400> SEQUENCE: 5

```
gtcatgtcgg cgaccctacg c                                             21
```

<210> SEQ ID NO 6
<211> LENGTH: 29
<212> TYPE: DNA
<213> ORGANISM: Ceratitis capitata

<400> SEQUENCE: 6

```
caacgagtga cagcaatgat attccttac                                     29
```

<210> SEQ ID NO 7
<211> LENGTH: 39
<212> TYPE: DNA
<213> ORGANISM: Ceratitis capitata

<400> SEQUENCE: 7

```
ggtgtggcta gctcgaagaa gttcctattc cgaagttcc                          39
```

<210> SEQ ID NO 8
<211> LENGTH: 22
<212> TYPE: DNA
<213> ORGANISM: Ceratitis capitata

<400> SEQUENCE: 8
gaaagctgtt cgggcttcag gc 22

<210> SEQ ID NO 9
<211> LENGTH: 25
<212> TYPE: DNA
<213> ORGANISM: Ceratitis capitata

<400> SEQUENCE: 9
cttggaggtg atgtcgaatt tggtg 25

<210> SEQ ID NO 10
<211> LENGTH: 21
<212> TYPE: DNA
<213> ORGANISM: Ceratitis capitata

<400> SEQUENCE: 10
caggcaatct gctccattaa c 21

<210> SEQ ID NO 11
<211> LENGTH: 21
<212> TYPE: DNA
<213> ORGANISM: Ceratitis capitata

<400> SEQUENCE: 11
gacctagtcc caaagatttc g 21

<210> SEQ ID NO 12
<211> LENGTH: 31
<212> TYPE: DNA
<213> ORGANISM: Ceratitis capitata

<400> SEQUENCE: 12
agtgcttaca ttcattttaa gagcacctca t 31

<210> SEQ ID NO 13
<211> LENGTH: 26
<212> TYPE: DNA
<213> ORGANISM: Ceratitis capitata

<400> SEQUENCE: 13
ctctggacgt catcttcact tacgtg 26

<210> SEQ ID NO 14
<211> LENGTH: 29
<212> TYPE: DNA
<213> ORGANISM: Ceratitis capitata

<400> SEQUENCE: 14
ctcgatatac agaccgataa aacacatgc 29

<210> SEQ ID NO 15
<211> LENGTH: 21
<212> TYPE: DNA
<213> ORGANISM: Ceratitis capitata

<400> SEQUENCE: 15
gccaccgagt atgaccggta g 21

<210> SEQ ID NO 16
<211> LENGTH: 27
<212> TYPE: DNA
<213> ORGANISM: Ceratitis capitata

<400> SEQUENCE: 16
ctgattttga actataacga ccgcgtg 27

<210> SEQ ID NO 17
<211> LENGTH: 19
<212> TYPE: DNA
<213> ORGANISM: Ceratitis capitata

<400> SEQUENCE: 17
tcacctacga ggacggcgg 19

<210> SEQ ID NO 18
<211> LENGTH: 24
<212> TYPE: DNA
<213> ORGANISM: Ceratitis capitata

<400> SEQUENCE: 18
gtgccaaagt tgtttctgac tgac 24

<210> SEQ ID NO 19
<211> LENGTH: 25
<212> TYPE: DNA
<213> ORGANISM: Ceratitis capitata

<400> SEQUENCE: 19
cacttaagcg acaagtttgg ccaac 25

<210> SEQ ID NO 20
<211> LENGTH: 27
<212> TYPE: DNA
<213> ORGANISM: Ceratitis capitata

<400> SEQUENCE: 20
ccctagaaag ataatcatat tgtgacg 27

<210> SEQ ID NO 21
<211> LENGTH: 26
<212> TYPE: DNA
<213> ORGANISM: Ceratitis capitata

<400> SEQUENCE: 21
catacttgat tgtgttttac gcgtag 26

<210> SEQ ID NO 22
<211> LENGTH: 25
<212> TYPE: DNA
<213> ORGANISM: Ceratitis capitata

<400> SEQUENCE: 22
caactcttct cgttttgaag tcagc 25

<210> SEQ ID NO 23
<211> LENGTH: 21
<212> TYPE: DNA
<213> ORGANISM: Ceratitis capitata

<400> SEQUENCE: 23

```
cgtcaggcaa tcgagctgtt c                                              21


<210> SEQ ID NO 24
<211> LENGTH: 22
<212> TYPE: DNA
<213> ORGANISM: Ceratitis capitata

<400> SEQUENCE: 24

ggataccgaa ttcatagcgg cg                                             22


<210> SEQ ID NO 25
<211> LENGTH: 23
<212> TYPE: DNA
<213> ORGANISM: Ceratitis capitata

<400> SEQUENCE: 25

ggtgagaagc atccattcca ggc                                            23


<210> SEQ ID NO 26
<211> LENGTH: 1014
<212> TYPE: DNA
<213> ORGANISM: Ceratitis capitata

<400> SEQUENCE: 26

atgggcagcc gcctggataa gtccaaagtc atcaactccg cgttggagct gttgaacgaa     60

gttggcattg agggactgac gacccgcaag ttggcgcaga agctgggcgt ggagcagccc    120

accctctact ggcacgtgaa gaataagcgg gcgctgctgg atgccctggc catcgagatg    180

ctcgaccgcc accacacgca tttttgcccg ttggaaggcg agtcctggca ggacttcctc    240

cgcaataacg ccaagtcgtt ccgctgcgct ctgctgtccc accgagacgg tgccaaagtc    300

catctcggca cgcgcccgac cgaaaagcaa tacgagacac tggagaacca gctcgcgttc    360

ctgtgccagc aaggcttcag cctggaaaat gctctctacg ctctgagcgc cgtcggtcac    420

tttaccctgg gctgcgtgct ggaggaccaa gagcatcaag tcgcaaaaga ggagcgcgag    480

accccaacaa ccgattcgat gcccccactg ctgcgtcagg caatcgagct gttcgatcat    540

caaggagccg agccggcatt cctgttcggc ttggagctga ttatctgcgg attggaaaag    600

caactgaaat gcgagtcggg ctcgggcccc gcgtacagcc gcgcgcgtac gaaaaacaat    660

tacgggtcta ccatcgaggg cctgctcgat ctcccggacg acgacgcccc cgaagaggcg    720

gggctggcgg ctccgcgcct gtcctttctc cccgcgggac acacgcgcag actgtcgacg    780

gcccccccga ccgatgtcag cctgggggac gagctccact tagacggcga ggacgtggcg    840

atggcgcatg ccgacgcgct agacgatttc gatctggaca tgttgggggga cggggattcc    900

ccgggtccgg gatttacccc ccacgactcc gccccctacg gcgctctgga tatggccgac    960

ttcgagtttg agcagatgtt taccgatgcc cttggaattg acgagtacgg tggg         1014


<210> SEQ ID NO 27
<211> LENGTH: 1014
<212> TYPE: DNA
<213> ORGANISM: Ceratitis capitata

<400> SEQUENCE: 27

atggtcagcc gcctggataa gtccaaagtc atcaactccg cgttggagct gttgaacgaa     60

gttggcattg agggactgac gacccgcaag ttggcgcaga agctgggcgt ggagcagccc    120

accctctact ggcacgtgaa gaataagcgg gcgctgctgg atgccctggc catcgagatg    180

ctcgaccgcc accacacgca tttttgcccg ttggaaggcg agtcctggca ggacttcctc    240
```

```
cgcaataacg ccaagtcgtt ccgctgcgct ctgctgtccc accgagacgg tgccaaagtc    300

catctcggca cgcgcccgac cgaaaagcaa tacgagacac tggagaacca gctcgcgttc    360

ctgtgccagc aaggcttcag cctggaaaat gctctctacg ctctgagcgc cgtcggtcac    420

tttaccctgg gctgcgtgct ggaggaccaa gagcatcaag tcgcaaaaga ggagcgcgag    480

accccaacaa ccgattcgat gcccccactg ctgcgtcagg caatcgagct gttcgatcat    540

caaggagccg agccggcatt cctgttcggc ttggagctga ttatctgcgg attggaaaag    600

caactgaaat gcgagtcggg ctcgggcccc gcctacagcc gcgcccgcac caagaacaac    660

tacggcagca ccatcgaggg cctgctggat ctgccggatg atgatgcccc ggaggaggcg    720

ggcctggccg ccccgcgcct gagcttcctg ccggccggac acacccgccg cctgtcgacc    780

gccccgccga ccgacgtgag cctgggcgat gagctgcacc tggatggcga ggatgtggcg    840

atggcccacg ccgatgccct ggacgacttc gacctggaca tgctgggcga tggcgatagc    900

ccgggaccgg gattcacccc gcacgatagc gccccctacg gcgccctgga tatggccgat    960

ttcgagttcg agcagatgtt caccgacgcc ctgggcatcg atgagtacgg cggc         1014
```

<210> SEQ ID NO 28
<211> LENGTH: 1008
<212> TYPE: DNA
<213> ORGANISM: Ceratitis capitata

<400> SEQUENCE: 28

```
atggtcagcc gcctggacaa gagcaaggtg atcaacagcg ccctggagct gctgaacgaa     60

gtgggcatcg agggcctgac cacccgcaag ctggcccaga agctgggcgt ggaacagccg    120

accctgtact ggcacgtgaa gaacaagcgc gccctgctgg acgccctggc catcgaaatg    180

ctggatcgcc accacaccca cttctgcccg ctggagggcg agagctggca ggatttcctg    240

cgcaacaacg ccaagagctt ccgctgcgcc ctgctgtcgc accgcgatgg cgccaaggtg    300

cacctgggca cccgcccgac cgagaagcag tacgagaccc tggagaacca gctggccttc    360

ctgtgccagc agggcttcag cctggagaac gccctgtacg ccctgagcgc cgtgggccac    420

ttcaccctgg gctgtgtgct ggaggatcag gagcaccagg tggccaagga ggagcgcgag    480

accccgacca ccgatagcat gccgccgctg ctgcgccagg ccatcgagct gttcgatcac    540

cagggcgccg agccggcctt cctgttcggc ctggagctga tcatctgcgg cctggaaaag    600

cagctgaagt gcgagagcgg cagcgcctac agccgcgccc gtaccaagaa caactatggc    660

agcaccatcg agggactgct ggacctgccg gatgacgatg ccccggagga agccggcctg    720

gccgcccccc gcctgagctt cctgcccgcc ggacacacgc gccgcctgag caccgccccg    780

ccgaccgatg tgagcctggg cgacgagctg cacctggatg gagaggatgt ggcaatggcc    840

cacgccgacg ccctggacga tttcgacctg gatatgctgg gcgatggaga tagcccggga    900

ccgggcttca cgccccacga tagcgccccg tacggcgccc tggacatggc cgacttcgag    960

ttcgagcaaa tgttcaccga cgcgctgggc atcgatgagt atggcggg               1008
```

<210> SEQ ID NO 29
<211> LENGTH: 337
<212> TYPE: PRT
<213> ORGANISM: Ceratitis capitata

<400> SEQUENCE: 29

```
Gly Ser Arg Leu Asp Lys Ser Lys Val Ile Asn Ser Ala Leu Glu Leu
1               5                   10                  15
```

```
Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Gly
        195                 200                 205

Pro Ala Tyr Ser Arg Ala Arg Thr Lys Asn Asn Tyr Gly Ser Thr Ile
    210                 215                 220

Glu Gly Leu Leu Asp Leu Pro Asp Asp Asp Ala Pro Glu Glu Ala Gly
225                 230                 235                 240

Leu Ala Ala Pro Arg Leu Ser Phe Leu Pro Ala Gly His Thr Arg Arg
                245                 250                 255

Leu Ser Thr Ala Pro Pro Thr Asp Val Ser Leu Gly Asp Glu Leu His
            260                 265                 270

Leu Asp Gly Glu Asp Val Ala Met Ala His Ala Asp Ala Leu Asp Asp
        275                 280                 285

Phe Asp Leu Asp Met Leu Gly Asp Gly Asp Ser Pro Gly Pro Gly Phe
    290                 295                 300

Thr Pro His Asp Ser Ala Pro Tyr Gly Ala Leu Asp Met Ala Asp Phe
305                 310                 315                 320

Glu Phe Glu Gln Met Phe Thr Asp Ala Leu Gly Ile Asp Glu Tyr Gly
                325                 330                 335

Gly
```

<210> SEQ ID NO 30
<211> LENGTH: 313
<212> TYPE: DNA
<213> ORGANISM: Ceratitis capitata

<400> SEQUENCE: 30

```
ttaaccctag aaagatagtc tgcgtaaaat tgacgcatgc attcttgaaa tattgctctc     60

tctttctaaa tagcgcgaat ccgtcgctgt gcatttagga catctcagtc gccgcttgga    120

gctcccgtga ggcgtgcttg tcaatgcggt aagtgtcact gattttgaac tataacgacc    180

gcgtgagtca aaatgacgca tgattatctt ttacgtgact tttaagattt aactcatacg    240
```

-continued

```
ataattatat tgttatttca tgttctactt acgtgataac ttattatata tatattttct    300

tgttatagat atc                                                        313


<210> SEQ ID NO 31
<211> LENGTH: 868
<212> TYPE: DNA
<213> ORGANISM: Ceratitis capitata

<400> SEQUENCE: 31

taagaggcgc ggtaaaccgc aaatggttat gtattataat caaactaaag gcggagtgga     60

cacgctagac caaatgtgtt ctgtgatgac ctgcagtagg aagacgaata ggtggcctat    120

ggcattattg tacggaatga taaacattgc ctgcataaat tcttttatta tatacagcca    180

taatgtcagt agcaagggag aaaaggtcca aagtcgcaaa aaatttatga gaaaccttta    240

catgagcctg acgtcatcgt ttatgcgtaa gcgtttagaa gctcctactt tgaagagata    300

tttgcgcgat aatatctcta atattttgcc aaatgaagtg cctggtacat cagatgacag    360

tactgaagag ccagtaatga aaaaacgtac ttactgtact tactgcccct ctaaaataag    420

gcgaaaggca aatgcatcgt gcaaaaaatg caaaaaagtt atttgtcgag agcataatat    480

tgatatgtgc caaagttgtt tctgactgac taataagtat aatttgtttc tattatgtat    540

aagttaagct aattacttat tttataatac aacatgactg tttttaaagt acaaaataag    600

tttatttttg taaaagagag aatgtttaaa agttttgtta ctttatagaa gaaattttga    660

gtttttgttt ttttttaata aataaataaa cataaataaa ttgtttgttg aatttattat    720

tagtatgtaa gtgtaaatat aataaaactt aatatctatt caaattaata aataaacctc    780

gatatacaga ccgataaaac acatgcgtca attttacgca tgattatctt taacgtacgt    840

cacaatatga ttatctttct agggttaa                                        868


<210> SEQ ID NO 32
<211> LENGTH: 446
<212> TYPE: DNA
<213> ORGANISM: Ceratitis capitata

<400> SEQUENCE: 32

gaaaggcaaa tgcatcgtgc aaaaaatgca aaaaagttat ttgtcgagag cataatattg     60

atatgtgcca aagttgtttc tgactgacta ataagtataa tttgtttcta ttatgtataa    120

gttaagctaa ttacttattt tataatacaa catgactgtt tttaaagtac aaaataagtt    180

tatttttgta aaagagagaa tgtttaaaag ttttgttact ttatagaaga aattttgagt    240

ttttgttttt ttttaataaa taaataaaca taaataaatt gtttgttgaa tttattatta    300

gtatgtaagt gtaaatataa taaaacttaa tatctattca aattaataaa taaacctcga    360

tatacagacc gataaaacac atgcgtcaat tttacgcatg attatcttta acgtacgtca    420

caatatgatt atctttctag ggttaa                                          446
```

GENE EXPRESSION SYSTEM

CROSS REFERENCE TO RELATED APPLICATIONS

This is a Continuation of U.S. application Ser. No. 15/313,922, filed Nov. 23, 2016, which is a U.S. National Stage Application of PCT/GB2015/051633, filed Jun. 4, 2015, which claims priority to Great Britain Application No. GB1410023.4, filed Jun. 5, 2014, the disclosures of each is herein incorporated by reference in its entirety.

The present invention relates to conditional lethal expression systems for insects, their use, and methods of population control using insects transformed therewith.

A significant method of control of insect populations in the wild involves irradiated Sterile Insect Technique (SIT), which serves as an environmentally friendly method of insect control, involves mass rearing the flies and rendering the males infertile by irradiation. However, SIT is not effective or economically viable in all areas when compared to other control methods, and the success of the radiation SIT programme is dependent on the irradiated fly having similar behaviour patterns to the wild populations of males. A further limitation of this method of SIT is that of separation of the males and females at the pupal stage. It is desirable to release only male insects, as the release of female insects may result in greater crop damage at the release area. In particular, the separation involves labour-intensive and time-consuming manual sorting of the insects.

An alternative method has been the introduction of the temperature-sensitive-lethal (TSL) sexing strain, whereby a chromosomal translocation of a spontaneous mutation in the Medfly has allowed a temperature sensitive separation (Caceres 2002); this transformed line is 99% effective at removing females (Mumford 2012). However, TSL strain has demonstrated a high degree of instability and, thus, requires laborious and expensive filter colony set-up in mass rearing facilities (Caceres 2002).

A further method of control is the use of a repressible, dominant, lethal genetic system introduced into the genome of an insect. A further refinement of this method has been to use a female-specific repressible, dominant, lethal genetic system. These systems provide for the female-specific expression of a lethal gene product in the absence of a repressor. Two-component systems were developed, wherein a transactivator gene product acts as a transactivator for a lethal gene, by activating a promoter for the lethal gene. The system is repressible by providing a repressor which would prevent the action of transactivator gene product on the promoter for the lethal gene.

In later developments of this female-specific, repressible, dominant, lethal, genetic system, a single gene to be expressed is provided, with the gene product being both a transactivator for the gene and being the lethal product, thereby creating a positive feedback loop leading to the death of the transgenic insect.

Gong et al. disclose strains of Medfly harbouring tetracycline transactivator (tTA) that causes lethality in early developmental stages of the heterozygous progeny but has little effect on survival of the parental transgenic insects. In this system, tTA is both the transactivator and the lethal, as high levels of tTA are thought to be deleterious to cells. In fact, tTA was modified to be optimised for expression in insects, and this variant is referred to as tTAV. However, this document discloses that some insects escaped the lethal effect of tTAV, and that the possibility of biochemical resistance to the lethal effector molecule may be a drawback to this system. It is also disclosed that lethality earlier in development is preferred.

Fu et al. disclose a female-specific autocidal genetic system in *C. capitata*, using tTA and Cctra. Cctra inserted into tTA results in disruption of the tTA transcript in male splice variants but not in female splice variants (FIG. 1). Previously, there has been a lack of characterised gene expression systems capable of conferring female-specific expression at early developmental stages. The system of Fu et al. provides such female-specific expression at early developmental stages. The Cctra female-specific intron was inserted into the tTAV-coding region in a positive feedback loop of Gong et al., and this provided female-specific lethality.

However, the data obtained in Fu et al. indicates that lethality occurs in the late larval/early pupal stages of development and that most of the insect lines were not 100% penetrant. Fu et al. also discloses that a potential difficulty of this system is saturation of the response capacity. The factors regulating alternative splicing are thought to be in relatively short supply, so that the alternative splicing pathway may be saturated if too much pre-mRNA is produced. In order for the female-specific positive-feedback system to be lethal, large amounts of tTAV must be produced, so high levels of F1-type (female-type) splicing are required. Another problem is inefficiency, as a substantial proportion of the pre-mRNA in females is processed in the male forms (M1 and M2); these do not produce a functional protein, so tend to attenuate the lethality relative to non-sex-specific constructs.

It is therefore desirable to provide an improved female-specific, repressible, dominant, lethal genetic system, with earlier onset of the lethal effect in development than previously seen, preferably with improved penetrance, and preferably with a reduced risk of biochemical resistance. An additional desirable improvement is the increased stability of the system once inserted into the host genome.

Surprisingly, it has now been found that the penetrance of such a transgenic system is improved by providing a transgene having two female-specific, repressible, dominant, lethal expression systems. The provision of two such expression systems surprisingly also has the further advantage of inducing earlier onset of lethality, in addition to reducing the risk of developing biochemical resistance to the lethal product.

Thus, in a first aspect, there is provided a polynucleotide sequence comprising a first and a second gene expression system, wherein:

i) the first gene expression system comprises the components; a first dominant lethal gene operably linked to a first promoter, a gene encoding a first activating transcription factor, and a first splice control sequence, ii) the second gene expression system comprises the components; a second dominant lethal gene operably linked to a second promoter, a gene encoding a second activating transcription factor, and a second splice control sequence, wherein

- each of said activating transcription factors is capable of activating at least one of said promoters, provided that both of said promoters are activated when both of said transcription factors are expressed,
- each of the first and second splice control sequences mediates female-specific expression of the first and second dominant lethal genes, respectively, by alternative splicing,
- the transactivation activity of each of the first and second activating transcription factors is repressible by a first and a second exogenous control factor, respectively, wherein said first exogenous control factor is the same as or different from said second exogenous control factor, and each of said components of said first gene expression system are the same as or different from said components of said second gene expression system.

The expression systems of the invention are capable of being expressed in insects, preferably at least in dipterans, coleopterans and/or lepidopterans.

The expression systems of the invention preferably each comprise a promoter selected for expression in insects, preferably at least in dipterans, coleopterans and/or lepidopterans. The promoter may be an insect promoter, or a promoter that is operational in at least one tissue of a target insect.

Two or more conditional, dominant, lethal gene expression systems have been shown to provide high levels of penetrance in insects. Lethality is generally induced at an earlier stage of development and the risk of biochemical resistance is reduced, as compared to a single insect conditional, dominant, lethal gene expression system. The invention is useful for the control of insect populations.

Each of the two systems comprises a dominant lethal gene to be expressed and an activating transcription factor to activate expression of the lethal gene. The effect of the activating transcription factor can be repressed, and the product of the dominant lethal gene has a lethal effect on the insect when expressed in sufficient quantity. Each expression system also comprises a splice control sequence which provides for female-specificity of the lethal effect. The presence of two female-specific, repressible, dominant, lethal expression systems improves the penetrance of the system by increasing the amount of lethal product expressed, thereby increasing the probability of effective lethality. The presence of two expression systems also induces earlier onset of lethality during development due to an accumulation of lethal product, and the risk of resistance mechanisms is reduced because the probability of developing resistance to both expression systems is low.

The term "penetrance", as used herein, refers to the proportion of individuals carrying a particular variant of a gene that also express the phenotypic trait associated with that variant. Thus, "penetrance", in relation to the present invention, refers to the proportion of transformed organisms which express the lethal phenotype.

The term "construct", as used herein, refers to an artificially constructed segment of DNA for insertion into a host organism, for genetically modifying the host organism. At least a portion of the construct is inserted into the host organism's genome and alters the phenotype of the host organism. The construct may form part of a vector or be the vector.

The term "transgene", as used herein, refers to the polynucleotide sequence comprising a first and a second gene expression system to be inserted into a host organism's genome, to alter the host organism's phenotype.

The term "gene expression system", as used herein, refers to a gene to be expressed together with any genes and DNA sequences which are required for expression of said gene to be expressed.

The term "splice control sequence", as used herein, refers to a DNA sequence associated with a gene, wherein the DNA sequence, together with a spliceosome, mediates alternative splicing of a RNA product of said gene. Preferably, the splice control sequence, together with the spliceosome, mediates splicing of a RNA transcript of the associated gene to produce a mRNA coding for a functional protein and mediates alternative splicing of said RNA transcript to produce at least one alternative mRNA coding for a non-functional protein.

The term "transactivation activity", as used herein, refers to the activity of an activating transcription factor, which results in an increased rate of expression of a gene. The activating transcription factor may bind a promoter operably linked to said gene, thereby activating the promoter and, consequently, enhancing the expression of said gene. Alternatively, the activating transcription factor may bind an enhancer associated with said promoter, thereby promoting the activity of said promoter via said enhancer.

The term "lethal gene", as used herein, refers to a gene whose expression product has a lethal effect, in sufficient quantity, on the organism within which the lethal gene is expressed.

The term "lethal effect", as used herein, refers to a deleterious or sterilising effect, such as an effect capable of killing the organism per se or its offspring, or capable of reducing or destroying the function of certain tissues thereof, of which the reproductive tissues are particularly preferred, so that the organism or its offspring are sterile. Therefore, some lethal effects, such as poisons, will kill the organism or tissue in a short time-frame relative to their life-span, whilst others may simply reduce the organism's ability to function, for instance reproductively.

The term "tTAV gene variant", as used herein, refers to a polynucleotides encoding the functional tTA protein but which differ in the sequence of nucleotides.

The term "promoter", as used herein, refers to a DNA sequence, generally directly upstream to the coding sequence, required for basal and/or regulated transcription of a gene. In particular, a promoter has sufficient information to allow initiation of transcription, generally having a transcription initiation start site and a binding site for the polymerase complex.

The term "minimal promoter", as used herein, refers to a promoter as defined above, generally having a transcription initiation start site and a binding site for the polymerase complex, and further generally having sufficient additional sequence to permit these two to be effective. Other sequence information, such as that which determines tissue specificity, for example, is usually lacking.

The term "exogenous control factor", as used herein, refers to a substance which is not found naturally in the host organism and which is not found in a host organism's natural habitat, or an environmental condition not found in a host organism's natural habitat. Thus, the presence of the exogenous control factor is controlled by the manipulator of a transformed host organism in order to control expression of the gene expression system.

The term "tetO element", as used herein, refers to one or more tetO operator units positioned in series.

The term, for example, "tetOx7", as used herein, refers to a tetO element consisting of the indicated number of tetO operator units. Thus, references to "tetOx7" indicates a tetO element consisting of seven tetO operator units. Similarly, references to "tetOx14" refers to a tetO element consisting of 14 tetO operator units, and so on.

The term "tra intron", as used herein, refers to a splice control sequence wherein alternative splicing of the RNA transcript is regulated by the TRA protein, for instance binding thereof, alone or in combination (i.e. when complexed) with TRA2.

The term "minimal repeat", as used herein, refers to the highly conserved repeat sequences observed to be required for the activity of a given transposase.

Where reference to a particular nucleotide or protein sequence is made, it will be understood that this includes reference to any mutant or variant thereof, having substantially equivalent biological activity thereto. Preferably, the mutant or variant has at least 85%, preferably at least 90%, preferably at least 95%, preferably at least 99%, preferably at least 99.9%, and most preferably at least 99.99% sequence identity with the reference sequences.

BRIEF DESCRIPTION OF THE SEQUENCE LISTINGS

Figure 1:
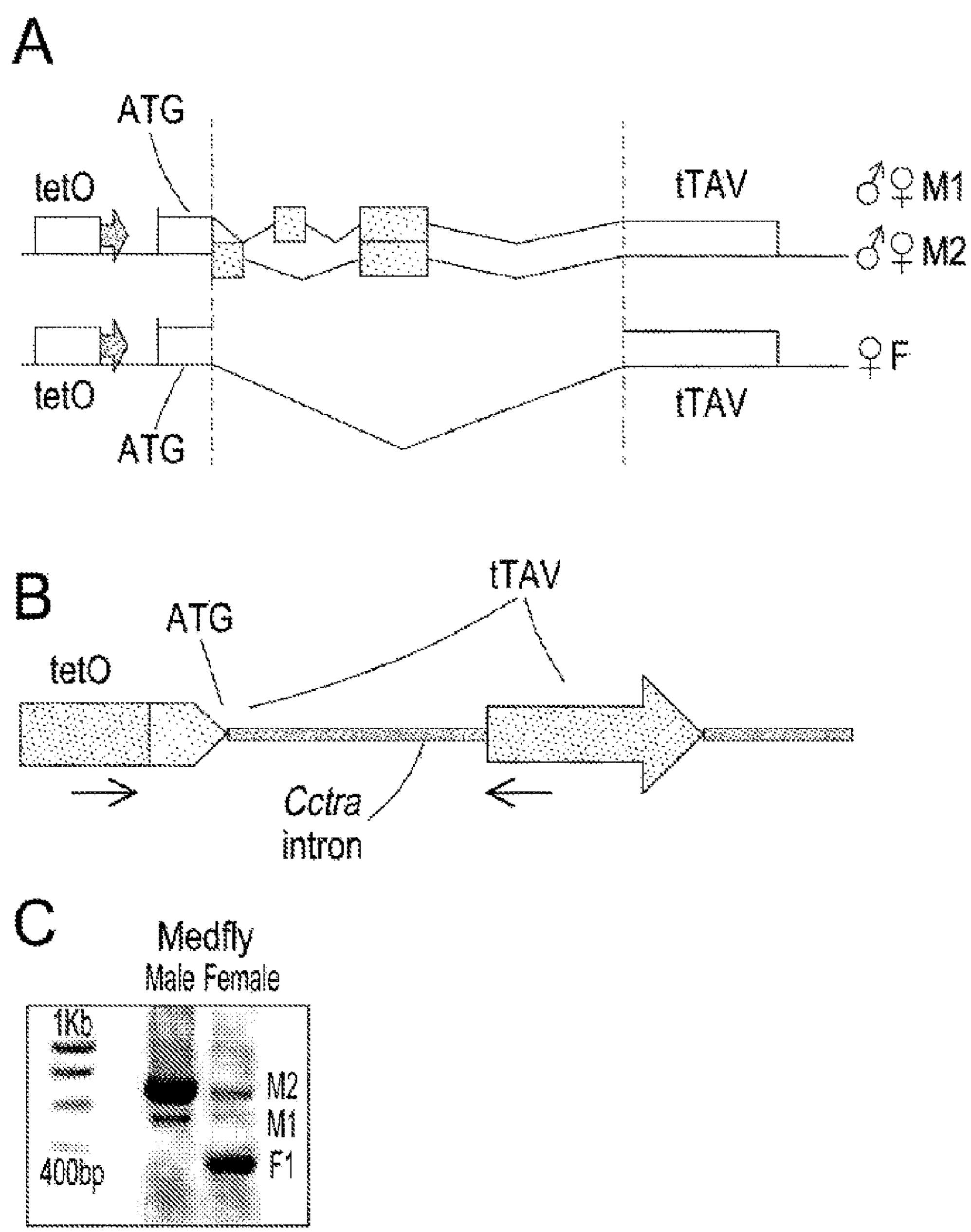
FIG. 1 shows schematic representations of the female-specific lethality trait and a photograph of a gel. Insertion of the Cctra female-specific intron in the tTA component of a tetracycline-repressible gene system such that only females produce mRNA encoding functional tTA. Panel A: Boxes indicate exons containing stop codons present in the male transcripts leading to a truncated TRA. Panel B: Arrows below the representation indicate the location of primer annealing for the RT-PCR analysis. Panel C: is a photograph of a gel showing the results of PCR analysis of Tra splicing for sex specific expression. Cctra intron splices correctly to produce the F1 transcript of tTAV in females only.

SEQ ID NO: 1 shows a nucleotide sequence of the insect gene expression system.

SEQ ID NO: 2 shows a nucleotide sequence of the gene expression system flanked by *C. capitata* genomic DNA.

SEQ ID NO: 3 shows a nucleotide sequence of the gene expression system flanked by *C. capitata* genomic DNA.

SEQ ID NO: 4 shows a nucleotide sequence of primer TG1-3864AttpflR.

SEQ ID NO: 5 shows a nucleotide sequence of primer TG1-AttPF2.

SEQ ID NO: 6 shows a nucleotide sequence of primer TG2-3864FRTFIF.

SEQ ID NO: 7 shows a nucleotide sequence of primer TG2-FRTNheF.

SEQ ID NO: 8 shows a nucleotide sequence of primer CcAdh2RTF.

SEQ ID NO: 9 shows a nucleotide sequence of primer CcAdh2RTR.

SEQ ID NO: 10 shows a nucleotide sequence of primer Cc3864FRTtaqF.

SEQ ID NO: 11 shows a nucleotide sequence of primer Cc3864FRTtaqR.

SEQ ID NO: 12 shows a nucleotide sequence of Cc3864FRTprobe.

SEQ ID NO: 13 shows a nucleotide sequence of primer PB5out.

SEQ ID NO: 14 shows a nucleotide sequence of primer PB3out.

SEQ ID NO: 15 shows a nucleotide sequence of primer Diag-5PBmin.

SEQ ID NO: 16 shows a nucleotide sequence of primer Diag-Pb5.

SEQ ID NO: 17 shows a nucleotide sequence of primer AmCydiagF.

SEQ ID NO: 18 shows a nucleotide sequence of primer Dlag6-pb3.

SEQ ID NO: 19 shows a nucleotide sequence of primer Dlag-K10-1.

SEQ ID NO: 20 shows a nucleotide sequence of primer Diag7-pb3.

SEQ ID NO: 21 shows a nucleotide sequence of primer Diag2-hr5.

SEQ ID NO: 22 shows a nucleotide sequence of primer Diag3K10.

SEQ ID NO: 23 shows a nucleotide sequence of primer ttaVdiagF.

SEQ ID NO: 24 shows a nucleotide sequence of primer Med3864altF.

SEQ ID NO: 25 shows a nucleotide sequence of primer Med3864fldiagR2.

SEQ ID NO: 26 shows a nucleotide sequence of the tTAV gene.

SEQ ID NO: 27 shows a nucleotide sequence of the tTAV2 gene.

SEQ ID NO: 28 shows a nucleotide sequence of the tTAV3 gene.

SEQ ID NO: 29 shows a polypeptide sequence of the tTAV protein.

SEQ ID NO: 30 shows a nucleotide sequence of a 5' piggyBac end including 5'ITR.

SEQ ID NO: 31 shows a nucleotide sequence of a 3' piggyBac end including 3'ITR.

SEQ ID NO: 32 shows a nucleotide sequence of a 3' piggyBac end including 3'ITR.

DETAILED DESCRIPTION OF THE INVENTION

The present invention allows for selective control of the expression of the first and/or second dominant lethal genes, thereby providing selective control of the expression of a lethal phenotype. It will therefore be appreciated that each of the lethal genes encodes a functional protein. It is preferred that each gene expression system is as described in WO2005/012534.

Each of the lethal genes has a lethal effect which is conditional. An example of suitable conditions includes temperature, so that the lethal is expressed at one temperature but not, or to a lesser degree, at another temperature. Another example of a suitable condition is the presence or absence of a substance, whereby the lethal is expressed in either the presence or absence of the substance, but not both. It is preferred that the effect of the lethal gene is conditional and is not expressed under permissive conditions requiring the presence of a substance which is absent from the natural environment of the organism, such that the lethal effect of the lethal system occurs in the natural environment of the organism.

Each lethal genetic system may act on specific cells or tissues or impose its effect on the whole organism. Systems that are not strictly lethal but impose a substantial fitness cost are also envisioned, for example leading to blindness, flightlessness (for organisms that could normally fly), or sterility. Systems that interfere with sex determination are also envisioned, for example transforming or tending to transform all or part of an organism from one sexual type to another. However, it is preferred that the product of each lethal gene results in sterilisation, as this allows the organism to compete in the natural environment ("in the wild") with wild-type organisms, but the sterile organism cannot then produce viable offspring. In this way, the present invention achieve a similar result to techniques such as the Sterile Insect Technique (SIT) in insects, without the problems associated with SIT, such as the cost, danger to the user, and reduced competitiveness of the irradiated organism.

In some embodiments, the product of at least one of the lethal genes is preferably an apoptosis-inducing factor, such as the AIF protein described for instance in Cande et al (*Journal of Cell Science* 115, 4727-4734 (2002)) or homologues thereof. AIF homologues are found in mammals and even in invertebrates, including insects, nematodes, fungi, and plants, meaning that the AIF gene has been conserved throughout the eukaryotic kingdom. In other embodiments, the product of at least one of the lethal genes is Hid, the protein product of the head involution defective gene of *Drosophila melanogaster*, or Reaper (Rpr), the product of the reaper gene of *Drosophila*, or mutants thereof. Use of Hid was described by Heinrich and Scott (*Proc. Natl Acad. Sci USA* 97, 8229-8232 (2000)). Use of a mutant derivative, HidAla5 was described by Horn and Wimmer (Nature Biotechnology 21, 64-70 (2003)). Use of a mutant derivative of Rpr, RprKR, is described herein (see also White et al 1996, Wing et al., 2001, and Olson et al., 2003). Both Rpr and Hid are pro-apoptotic proteins, thought to bind to IAP1. IAP1 is a well-conserved anti-apoptotic protein. Hid and Rpr are therefore expected to work across a wide phylogenetic range (Huang et al., 2002, Vernooy et al., 2000) even though their own sequence is not well conserved.

In other embodiments, at least one of the lethal genes is Nipp1Dm, the *Drosophila* homologue of mammalian Nipp1 (Parker et al *Biochemical Journal* 368, 789-797 (2002); Bennett et al., Genetics 164, 235-245 (2003)). Nipp1Dm is another example of a protein with lethal effect if expressed at a suitable level, as would be understood by the skilled person. Indeed, many other examples of proteins with a lethal effect will be known to the person skilled in the art.

Preferably, at least one of the lethal genes is tTA or a tTAV gene variant. tTAV is an analogue of tTA, wherein the sequence of tTA has been modified to enhance the compatibility with the desired insect species. Variants of tTAV are possible, encoding the tTA protein, such that the tTAV variant gene products have the same functionality as the tTA gene product. Thus, the variants of the tTAV gene comprise modified nucleotide sequences as compared to the tTA nucleotide sequence and to each other, but encode proteins with the same function. Thus, tTAV gene variants can be used in the place of tTA. Indeed, it is preferred to use tTAV gene variants in the transgene of the invention.

Any combination of lethal genes may be used, and, in some embodiments, the lethal genes are the same while, in other embodiments, the lethal genes are different. The improved penetrance of the lethal effect and the earlier onset of lethality is achieved by an accumulation of lethal product.

In preferred embodiments, each of the first and second lethal genes is independently tTA or a tTAV gene variant. In some embodiments, each of the first and second lethal gene is independently one of tTAV (SEQ ID NO: 26), tTAV2 (SEQ ID NO: 27) and tTAV3 (SEQ ID NO: 28). In other embodiments, the first and second lethal genes are the same. In further embodiments, one of the first and second lethal genes is tTAV (SEQ ID NO: 26) and the other gene is tTAV3 (SEQ ID NO: 28). However, any combination of tTAV variants may be used; thus, in some embodiments, one of the first and second genes is tTAV (SEQ ID NO: 26) and the other is tTAV2 (SEQ ID NO: 27), while, in a further embodiment, one of the first and second genes is tTAV2 (SEQ ID NO: 27) and the other gene is tTAV3 (SEQ ID NO: 28). In other embodiments, the first lethal gene is tTAV (SEQ ID NO: 26) and the second lethal gene is tTAV3 (SEQ ID NO: 28).

Each lethal gene is operably linked to a promoter, wherein said promoter is capable of being activated by an activating transcription factor encoded by a gene also included in at least one of the gene expression systems.

The promoter may be a large or complex promoter, but these often suffer the disadvantage of being poorly or patchily utilised when introduced into non-host insects. Accordingly, in some embodiments, it is preferred to employ minimal promoters. It will be appreciated that minimal promoters may be obtained directly from known sources of promoters, or derived from larger naturally occurring, or otherwise known, promoters. Suitable minimal promoters and how to obtain them will be readily apparent to those skilled in the art. For example, suitable minimal promoters include a minimal promoter derived from Hsp70, a P minimal promoter, a CMV minimal promoter, an Act5C-based minimal promoter, a BmA3 promoter fragment, and an Adh core promoter (Bieschke, E., Wheeler, J., and Tower, J. (1998). "Doxycycline-induced transgene expression during *Drosophila* development and aging". Mol Gen Genet, 258, 571-579). Not all minimal promoters will necessarily work in all species of insect, but it is readily apparent to those skilled in the art as to how to ensure that the promoter is active.

It is preferred that at least one of the operably-linked promoters present in the invention is active during early development of the host organism, and particularly preferably during embryonic stages, in order to ensure that the lethal gene is expressed during early development of the organism.

In some embodiments, at least one of the promoters is the minimal promoter is a heat shock promoter, such as Hsp70. In other embodiments, at least one of the promoters is the srya embryo-specific promoter (Horn & Wimmer (2003)) from *Drosophila melanogaster*, or its homologues, or promoters from other embryo-specific or embryo-active genes, such as that of the *Drosophila* gene slow as molasses (slam), or its homologues from other species.

In some embodiments, at least one of the promoters is a minimal promoter. In some embodiments, each of the promoters is independently Hsp70, Hsp73 or srya. In preferred embodiments, one of the first and second promoters is Hsp70 and the other is srya. In one embodiment, the first promoter is Hsp70 and the second promoter is srya.

Each gene expression system further comprises a gene encoding an activating transcription factor, wherein each activating transcription factor activates the expression of a lethal gene of the transgene. Thus, each gene encoding an activating transcription factor is able to be expressed by the host organism, to produce a functional protein. In particular, each activating transcription factor is capable of activating at least one promoter, wherein the promoter is operably linked to a lethal gene. Consequently, when an activating transcription factor activates a promoter, the expression of the lethal gene operably linked to the promoter is up-regulated. Each activating transcription factor may act on either the first or the second promoter, or each activating transcription factor may act on both the first and the second promoter. It is preferred that, when more than one activating transcription factor is expressed, more than one promoter is activated. Thus, when both the first and the second activating transcription factors are expressed, both the first and the second promoters are activated.

The gene products serving as activating transcription factors may act in any suitable manner. For example, the activating transcription factors may bind to an enhancer located in proximity to the at least one promoter, thereby serving to enhance polymerase binding at the promoter. Other mechanisms may be employed, such as repressor countering mechanisms, such as the blocking of an inhibitor of transcription or translation. Transcription inhibitors may be blocked, for example, by the use of hairpin RNA's or ribozymes to block translation of the mRNA encoding the inhibitor, or the product may bind the inhibitor directly, thereby preventing inhibition of transcription or translation.

In preferred embodiments, the effect of the activating transcription factor on the expression of the lethal gene can be controlled by the skilled person, preferably through the use of an exogenous control factor. It is particularly preferred that the transactivation activity of the activating transcription factor can be repressed by the exogenous control factor. Thus, it is possible to control the expression of the lethal gene by controlling the transactivating activity of the activating transcription factor. The presence of the exogenous control factor, applied by the skilled person, reduces the activity of the activating transcription factor on the relevant promoter. Consequently, activation of the promoter is repressed, such that expression of the operably linked lethal gene is reduced.

Any activating transcription factor, the transactivating activity of which can be controlled, may be used in each or either gene expression system. For example, the activating transcription factor may be the tetracycline-repressible transcription activator (tTA) protein which, when expressed, binds to the tetO operator sequence and drives expression from a nearby minimal promoter. Other examples of controllable activating transcription factors include GAL4.

The genes encoding the activating transcription factors may be the same or different. In preferred embodiments, each gene encoding an activating transcription factor is, independently, tTA or a tTAV gene variant. In particularly preferred embodiments, each of the genes encoding an activating transcription factor is independently a tTAV gene variant, and may be the same or different tTAV gene variant. Any combination of tTA and tTAV gene variant may be used. In some embodiments, each of the genes encoding an activating transcription factor is independently tTAV (SEQ ID NO: 26), tTAV2 (SEQ ID NO: 27) and tTAV3 (SEQ ID NO: 28), and the genes may be the same or different. In some embodiments each gene encoding an activating transcription factor is independently one of tTAV (SEQ ID NO: 26), tTAV2 (SEQ ID NO: 27) and tTAV3 (SEQ ID NO: 28). In further embodiments, one of the first and second genes encoding an activating transcription factor is tTAV (SEQ ID NO: 26) and the other gene is tTAV3 (SEQ ID NO: 28). Any combination of tTAV variants may be used; thus, in some embodiments, one of the first and second genes encoding an activating transcription factor is tTAV (SEQ ID NO: 26) and the other is tTAV2 (SEQ ID NO: 27), while, in a further embodiment, one of the first and second genes encoding an activating transcription factor is tTAV2 (SEQ ID NO: 27) and the other gene is tTAV3 (SEQ ID NO: 28). In other embodiments, the gene encoding the first activating transcription factor is tTAV (SEQ ID NO: 26) and the gene encoding the second activating transcription factor is tTAV3 (SEQ ID NO: 28).

As mentioned above, the activating control factors are controllable, preferably repressible, by an exogenous control factor. Control of the activating transcription factors may be by any suitable means, and may be effective at any level. For example, the control may be effective either to block transcription of the gene encoding the activating transcription factor or to block translation of the RNA product thereof, or to prevent or inhibit action of the translation product of the gene.

It will be appreciated that the exogenous control factor used will depend upon the activating transcription factor encoded in the transgene. For example, in embodiments wherein at least one of the genes encoding an activating transcription factor encodes GAL4, the control factor may be temperature (as GAL4 is somewhat cold-sensitive) and/or GAL80 or mutants thereof. In embodiments wherein at least one of the genes encoding an activating transcription factor is tTA or a tTAV gene variant, the exogenous control factor is tetracycline. Tetracycline binds the tTA or tTAV gene variant product (i.e. tTA), thereby preventing tTA from having a transactivation activity. The presence or absence, or modulation of the concentration, of tetracycline is used to control the system when tTA or an analogue thereof, such as tTAV, is used.

Expression of the dominant lethal genes of the transgene may be sex-specific, or be a combination of sex-specific and stage-specific, germline-specific or tissue-specific, due to the presence of at least one splice control sequence in each gene expression system. In preferred embodiments, the sex-specific expression is female-specific. The splice control sequence in each gene expression sequence allows an additional level of control of protein expression, in addition to the promoter. For instance, tissue or sex-specific expression in embryos only would be extremely difficult by conventional methods.

The first and second lethal genes comprise a coding sequence for a protein or polypeptide, i.e. at least one exon, and preferably two or more exons, capable of encoding a polypeptide, such as a protein or fragment thereof. Preferably, the different exons are differentially spliced together to provide alternative mRNAs. Preferably, said alternative spliced mRNAs have different coding potential, i.e. encode different proteins or polypeptide sequences. Thus, the expression of the coding sequence is regulated by alternative splicing.

Each splice control sequence in the system comprises at least one splice acceptor site and at least one splice donor site. The number of donor and acceptor sites may vary, depending on the number of segments of sequence that are to be spliced together.

In some embodiments, one or both splice control sequences regulate the alternative splicing by means of both intronic and exonic nucleotides. In other embodiments, one or both splice control sequences is an intronic splice control sequence. In other words, it is preferred that said splice control sequence(s) is substantially derived from polynucleotides that form part of an intron and are thus excised from the primary transcript by splicing, such that these nucleotides are not retained in the mature mRNA sequence.

It will be understood that in alternative splicing, sequences may be intronic under some circumstances (i.e. in some alternative splicing variants), but exonic under other circumstances (i.e. in other variants). Thus, the at least one splice control sequence of the present invention is preferably substantially derived from polynucleotides that form part of an intron in at least one alternative splicing variant, i.e. in either the first spliced mRNA product or the at least one alternatively spliced mRNA product. Thus, introns or intronic sequences can be viewed as spliced out in at least one transcript or transcript type.

In “normal” (non-alternative) splicing and in alternative splicing, introns are generally removed from the pre-RNA to form a spliced mRNA, which may then be translated into a polypeptide, such as a protein or protein fragment, having an amino acid sequence. Thus, it will be readily apparent to the skilled person how to determine those sequences of the present system that are to be considered intronic, rather than exonic.

As mentioned above, exonic sequences may be involved in the mediation of the control of alternative splicing, but it is preferred that at least some intronic control sequences are involved in the mediation of the alternative splicing. In other words, each gene expression system may also include splice control sequences present in exons, as long as there is some intronic involvement of control. In some embodiments, one or both splice control sequences is derived from or contains elements of the dsx gene, where, without being bound by theory, it is thought that exonic sequences assist in the mechanism of alternative splicing.

Thus, in some embodiments, the at least one splice control sequence does comprise exonic sequences and it will be understood that this is envisaged by definitions used to describe the present invention. Thus, as will be apparent, it is possible for some nucleotides to be encompassed within the definition of the at least one splice control sequence and also within the definition of a polynucleotide sequence encoding a functional protein. In other words, the definition of these elements can overlap, such that certain nucleotides can be covered by the definition of more than one element. However, the skilled person will recognise that this is not unusual in molecular biology, as nucleotides can often perform more than one role. In other embodiments, at least one of the splice control sequences is solely intronic, i.e. with no exonic influence.

It is preferred that at least one splice control sequence is capable of being removed from the pre-RNA, by splicing. Preferably, said at least one splice control sequence does not result in a frameshift in at least one splice variant produced. Preferably this is a splice variant encoding a full-length functional protein. In other words, at least the one splice control sequence preferably does not mediate the removal of nucleotides that form part, or were intended to form part of, the polynucleotide sequence encoding a functional protein, defined between a start codon and a stop codon, to be expressed in an organism. By this it is meant that nucleotides that are excised by splicing, in at least one splice variant, are not nucleotides that encode amino acids in the wild type form of the protein or gene. One or more splice variants may have said nucleotides excised, but at least one variant must retain these nucleotides, so that a frameshift is not induced in the at least one variant. These removed nucleotides are those that are removed in addition to the sequences that are normally spliced out such as the intron.

Interaction of the at least one splice control sequence with cellular splicing machinery, e.g. the spliceosome, leads to or mediates the removal of a series of, preferably, at least 50 consecutive nucleotides from the primary transcript and ligation (splicing) together of nucleotide sequences that were not consecutive in the primary transcript (because they, or their complement if the antisense sequence is considered, were not consecutive in the original template sequence from which the primary transcript was transcribed). Said series of at least 50 consecutive nucleotides comprises an intron. This mediation acts preferably in a sex-specific, more preferably, female-specific, manner such that equivalent primary transcripts in different sexes, and optionally also in different stages, tissue types, etc, tend to remove introns of different size or sequence, or in some cases may remove an intron in one case but not another. This phenomenon, the removal of introns of different size or sequence in different circumstances, or the differential removal of introns of a given size or sequence, in different circumstances, is known as alternative splicing. Alternative splicing is a well-known phenomenon in nature, and many instances are known, see above.

Where mediation of alternative splicing is sex-specific, it is preferred that the splice variant encoding a functional protein to be expressed in an organism is the F1 splice variant, i.e. a splice variant found only or predominantly in females, and preferably is the most abundant variant found in females, although this is not essential.

As mentioned above, in some embodiments the manner or mechanism of alternative splicing is sex-specific, preferably female-specific, and any suitable splice control sequence may be used. In preferred embodiments, at least one splice control sequence is derived from a tra intron. The *Ceratitis capitata* tra intron from the transformer gene was initially characterised by Pane et al (2002), supra. In insects, for instance, the TRA protein is differentially expressed in different sexes. In particular, the TRA protein is known to be present largely in females and, therefore, mediates alternative splicing in such a way that a coding sequence is expressed in a sex-specific manner, i.e. that in some cases a protein is expressed only in females or at a much higher level in females than in males or, alternatively, in other cases a protein is expressed only in males, or at a much higher level in males than in females. The mechanism for achieving this sex-specific alternative splicing mediated by the TRA protein or the TRA/TRA-2 complex is known and is discussed, for instance, in Pane et al (Development 129, 3715-3725 (2002)).

It will be appreciated that homologues of the *Ceratitis capitata* tra intron from the transformer gene exist in other species, and these can be easily identified in said species and also in their various genera. Thus, when reference is made to tra it will be appreciated that this also relates to tra homologues in other species. Thus, in some embodiments each of the alternative splicing mechanisms is independently derived from the *Ceratitis capitata* tra intron (Cctra), or from another ortholog or homolog. In some embodiments, the ortholog or homologue is from an arthropod, preferably a tephritid. In other embodiments, the ortholog or homologue is from the genus *Ceratitis, Bactrocera, Anastrepha* or *Rhagoletis*. In other embodiments, the ortholog or homolog is from *C. rosa*, or *B. zonata*. In further embodiments, the ortholog or homolog is from *B. zonata*, and this ortholog or homolog is referred to herein as Bztra (GenBank accession number BzTra KJ397268).

The splice control sequences of the gene expression systems may be the same or different. In some embodiments, it is preferred that the splice control sequences are derived from different species in order to reduce the risk of recombination. Thus, in preferred embodiments, one of the first and second splice control sequences is Cctra and the other is derived from a different species. In particularly preferred embodiments, one of the first and second splice control sequences is Cctra and the other is Bztra (GenBank accession number BzTra KJ397268). In another embodiment, the first splice control sequence is Cctra and the second splice control sequence is Bztra (GenBank accession number BzTra KJ397268).

The exact length of the splice control sequence derived from the tra intron is not essential, provided that it is capable of mediating alternative splicing. In this regard, it is thought that around 55 to 60 nucleotides is the minimum length for a modified tra intron, although the wild type tra intron (F1 splice variant) from *C. capitata* is in the region of 1345 nucleotides long.

In other embodiments, at least one of the splice control sequences is derived from the alternative splicing mechanism of the Actin-4 gene derived from an arthropod, preferably a tephritid. In embodiments wherein more than one splice sequence is derived from Actin-4, they may be derived from the same or from different tephritid species. In some embodiments, each Actin-4 gene is independently derived from a species of the *Ceratitis*, the *Bactrocera*, the *Anastrepha* or the *Rhagoletis* genera. In other embodiments, the first and second Actin-4 genes are independently derived from *Ceratitis capitata, Trocera oleae, Ceratitis rosa* or *Bactrocera zonata*. In some embodiments, at least one of the first and second Actin-4 genes is derived from *Ceratitis capitata*. In embodiments wherein more than one splice control sequence is derived from Actin-4, the splice control sequences may be derived from the same species. However, it is preferred that the splice control sequences are derived from different species in order to reduce the risk of recombination.

In some embodiments, at least one of the splice control sequences comprises at least a fragment of the doublesex (dsx) gene derived from an arthropod, preferably a tephritid. In some embodiments, more than one splice control sequence (e.g. both the first and second splice control sequences) is derived from dsx, and the dsx genes are derived from the same or different tephritid species. In some embodiments, each dsx gene is independently derived from a species of the *Ceratitis*, the *Bactrocera*, the *Anastrepha* or the *Rhagoletis* genera. In some embodiments, the dsx genes are independently derived from *Ceratitis capitata, Trocera oleae, Ceratitis rosa* or *Bactrocera zonata*. In some embodiments, at least one of the first and second dsx genes is derived from *Ceratitis capitata*. In embodiments wherein more than one splice control sequence is derived from dsx, the splice control sequences may be derived from the same species. However, it is preferred that the splice control sequences are derived from different species in order to reduce the risk of recombination.

While in some embodiments it is envisaged that the splice control sequences are derived from the same gene or intron of origin, in other embodiments the splice control sequences are derived from different genes or introns of origin. For example, in some embodiments, one of the splice control sequences is derived from the tra intron and the other splice control sequence is derived from the Actin-4 gene or the dsx gene.

In some embodiments, at least one of the first and second gene expression systems further comprises an enhancer which is associated with the promoter of the said gene expression system. At least one of the activating transcription factors, encoded in the first and/or second gene expression system, binds the enhancer, such that binding of the activating transcription factor(s) serves to enhance the activity of said associated promoter, for example, by promoting polymerase binding at the promoter.

In embodiments wherein a promoter of a gene expression system is associated with an enhancer, the promoter is substantially inactive in the absence of an active enhancer. Such promoters are preferably minimal promoters, such as those described above.

It is appreciated that those skilled in the art will recognise which enhancers are suitable for use in the present invention. In particular, the enhancer must be suitable to be bound by an activating transcription factor as described above (i.e. which is controllable by an exogenous control factor).

Thus, in embodiments wherein one or more of the dominant, lethal genes is tTA or a tTAV gene variant, an enhancer is a tetO element, comprising one or more tetO operator units. Upstream of a promoter, in either orientation, tetO is capable of enhancing levels of transcription from a promoter in close proximity thereto, when bound by the product of the tTA gene or a tTAV gene variant. In some embodiments, each enhancer is independently one of tetOx1, tetOx2, tetOx3, tetOx4, tetOx5, tetOx6, tetOx7, tetOx8, tetOx9, tetOx10, tetOx11, tetOx12, tetOx13, tetOx14, tetOx15, tetOx16, tetOx17, tetOx18, tetOx19, tetOx20 and tetOx21. In some embodiments, each enhancer is independently one of tetOx7, tetOx14 and tetOx21. In embodiments comprising more than one enhancer, the first enhancer is the same as or different from the second enhancer.

In preferred embodiments, both the first and the second gene expression system further comprise an enhancer, i.e. first and second enhancers, respectively. In some embodiments, one of the first and second enhancers is tetOx7 and the other enhancer is tetOx14. In other embodiments, the first enhancer is tetOx7 and the second enhancer is tetOx14.

In some embodiments, in a given gene expression system, it is preferred to link the dominant, lethal gene of said gene expression system with the gene encoding the activating transcription factor, of the same gene expression system. This may be achieved either by placing the two genes in tandem, including the possibility of providing the two as a fusion product, or, for example, by providing each gene with its own promoter in opposite orientations but in juxtaposition to the enhancer site.

In some embodiments, at least one of the gene expression systems forms a linear expression system. Thus, when the gene encoding the activating transcription factor is expressed, said activating transcription factor activates the promoter operably linked to the lethal gene, thereby up-regulating expression of the lethal gene. In some embodiments, the activating transcription factor activates only the promoter of the gene expression system that said activating transcription factor is expressed by. In other embodiments, the activating transcription factor may also activate the promoter of the other gene expression system.

In more preferred embodiments the dominant, lethal gene of a particular gene expression system is one and the same as the gene encoding the activating transcription factor also part of said gene expression system. Thus, the lethal product acts as the activating transcription factor for at least that gene expression system. Consequently, the lethal gene product activates the promoter of said gene expression system, thereby up-regulating expression of said lethal gene, resulting in a positive feedback loop. In other words, said dominant, lethal gene is also the gene encoding the activating transcription factor of said gene expression system. Thus, enhancement of the promoter serves not only to increase transcription of the activating transcription factor, but also leads to an accumulation of the lethal product of that gene expression system, resulting in a lethal effect on the host organism. In this regards, in one embodiment, it is particularly preferred that the positive feedback loop of the first and/or second gene expression systems is as disclosed in WO2005/012534.

Preferably, the first and/or second lethal gene is tTA or a tTAV gene variant as described above. In such embodiments, the relevant gene expression system further comprises a tetO element, as described above, as an enhancer. The gene encoding the activating transcription factor is one and the same as said lethal gene. The exogenous control factor is tetracycline. Thus, control is exerted on the positive feedback mechanism by the presence or absence of tetracycline, with the presence of tetracycline repressing the transactivation activity of the tTA or tTAV gene variant product on the promoter.

While, where at least one of the gene expression systems is a positive feedback loop, the activating transcription factor of said positive feedback loop activates the promoter of said gene expression system, in some embodiments the activating transcription factor also activates the promoter of the other gene expression system.

In some embodiments, one of the gene expression systems is a linear gene expression system as described above, and the other is a positive feedback loop, as described above.

In some embodiments, both the first and the second gene expression systems act as positive feedback loops. Each of the first and second gene expression systems expresses a different lethal gene product, such that the lethal gene product of the first gene expression system acts as the activating transcription factor for only the first gene expression system, and vice versa.

In preferred embodiments, both the first and the second gene expression systems act as positive feedback loops and express the same or similar lethal products. Thus, the lethal gene product expressed by the first gene expression system acts as an activating transcription factor for both the first and the second gene expression system, and vice versa. Accordingly, in some embodiments, both the first and the second gene expression systems comprise tTA or a tTAV gene variant as both the lethal gene and the gene encoding the activating transcription factor. Accordingly, both gene expression systems comprise an enhancer which is a tetO element as described above, which drives expression from the associated promoter. The first activating transcription factor (i.e. the first lethal gene product) can bind both the first and the second enhancers, and the second activating transcription factor can bind both the first and the second enhancers.

In some embodiments, one of the gene expression systems further comprises a third dominant, lethal gene operably linked to a third promoter. The activating transcription factor which is capable of activating the promoter of the relevant gene expression system is also capable of activating the third promoter, thereby enhancing expression of the third lethal gene. Thus, the expression of the third lethal gene may also be controlled, preferably repressed, by the exogenous control factor acting on said activating transcription factor.

In some embodiments, the relevant gene expression system further comprises an enhancer as described above, as well as optionally a third lethal gene and third promoter. In some such embodiments, the promoter of said gene expression system and the third promoter are both associated with said enhancer. Preferably, the promoter of said gene expression system is associated with one end of the enhancer and the third promoter is associated with the other end of the enhancer. In particular, as described above, some enhancers are capable of enhancing levels of transcription in either orientation.

The third lethal gene expresses a lethal product and, therefore, adds to the lethal effect of the transgene due to the accumulation of total lethal product. However, the improvements, described above, provided by the transgene are observed even without the presence of the third lethal gene in the transgene.

The third lethal gene may be any known to those skilled in the art. In some embodiments, the third lethal gene is any of those mentioned above in relation to the first and second lethal genes. In some embodiments, the third lethal gene is tTA, a tTAV gene variant or VP16. In preferred embodiments, the third lethal gene is VP16.

The third promoter may be any of those previously described in relation to the first and second promoters of the transgene. In some embodiments, the third promoter is a minimal promoter. In preferred embodiments, the third promoter is expressed in early development of the organism, preferably at least during embryonic stages. Preferably, the third promoter is Hsp70 or srya. In further embodiments, the third promoter is Hsp70.

In some embodiments, the transgene further comprises a genetic marker. In some embodiments, this marker is a fluorescent marker, being a gene encoding a fluorescent protein. Suitable genetic markers will be apparent to those skilled in the art. In preferred embodiments the fluorescent marker is DsRed2, which encodes the DsRed2 fluorescent protein. In other embodiments, the genetic marker is green fluorescent protein, or variants thereon. These genetic markers are useful in the selection of successfully transformed organisms. In addition, such markers are useful for distinguishing, for example, transgenic flies from wild type flies in the field, or those caught in the field.

It will be appreciated by those skilled in the art that, in embodiments comprising such genetic markers, the components required to express the marker will also be included in said embodiment. For example, it is envisaged that the fluorescent markers will be operably linked to a promoter therefore. Any suitable promoter may be used, for example Hr5/IE1.

In a preferred embodiment, tTAV (SEQ ID NO: 26) is the first dominant lethal gene, Hsp70 is the first promoter and Cctra is the first splice control sequence. This first gene expression system is a positive feedback loop as described above, such that the first lethal gene is also the gene encoding the first activating transcription factor. The first gene expression system further comprises a first enhancer, wherein the first enhancer is tetOx7. The second gene expression system comprises tTAV3 (SEQ ID NO: 28) as the second dominant, lethal gene, srya a as the second promoter and Bztra (GenBank accession number BzTra KJ397268) as the second splice control sequence. The second gene expression system also forms a positive feedback loop, such that the second lethal gene is the gene encoding the second activating transcription factor. The second gene expression system further comprises a second enhancer, wherein the second enhancer is tetOx14. The second gene expression system also further comprises a third lethal gene operably linked to a third promoter, wherein the third lethal gene is VP16 and the third promoter is Hsp70. The third promoter is associated with the second enhancer, with the second promoter being associated with one end of the enhancer and the third promoter being associated with the other end of the second enhancer. The transgene further comprises a genetic marker and a promoter therefor, wherein the genetic marker is DsRed2 and the promoter therefore is Hr5/IE1. In another embodiment, the transgene is a polynucleotide sequence having the sequence represented by SEQ ID NO:1.

The first and second gene expression systems are arranged in tandem, forming a transgene, and the transgene may or may not comprise linker sequences of nucleotides between each gene expression system. In embodiments not comprising a linker sequence between the gene expression systems, the first and second gene expression systems are contiguous. In embodiments which do comprise a linker sequence between the first and second gene expression systems, the linker sequence is from 1 bp to 10 kbp in length.

It will also be appreciated that, in embodiments wherein the transgene further comprises a genetic marker and its associated promoter, there may or may not be a linker sequence of nucleotides between the genetic marker (or its promoter) and the adjacent gene expression system. As above, in embodiments wherein no linker sequence is present, the genetic marker or its promoter is contiguous to one of the gene expression systems of the transgene. In embodiments wherein the transgene does comprise a linker sequence between the genetic marker and the relevant gene expression system, the linker sequence is from 1 bp to 10 kbp in length.

However, it will also be appreciated by those skilled in the art that it is preferred that there are no linker sequences present in the transgene, such that the elements of the transgene are contiguous. This is in order to reduce the risk of random mutations being introduced into the transgene and to reduce the risk of recombination.

The polynucleotide sequence, i.e. transgene, comprising the gene expression systems may form part of a genetic construct. Thus, in another aspect of the invention, there is provided a genetic construct comprising a first and a second gene expression system as described above. The genetic construct may comprise further components not forming part of the transgene. Such components may or may not be present in an organism transformed therewith.

In some embodiments, the genetic construct further comprises at least four inverted repeats, forming at least two pairs of opposing inverted repeats. The transgene is positioned between two pairs of inverted repeats. This means that excision of the pairs of inverted repeats, in situ, is effective to leave the gene expression systems inserted in the host genome, without flanking transposon-derived repeats being present in the host genome. The at least four inverted repeats are as described in WO2005/003364 and provide for elimination of transposable ends as described in Dafa'alla et al (2006).

In some embodiments, the genetic construct comprises four inverted repeats forming at least two pairs of opposing inverted repeats. In some such embodiments, it is preferred that the four inverted repeats are piggyBac inverted terminal repeats (ITRs). Two of the inverted repeats are distal to the transgene, i.e. they are external inverted repeats, and the remaining inverted repeats are internal inverted repeats. In particular, this means that one internal inverted repeat is between one external inverted repeat and the transgene. The four inverted repeats therefore form four different transposable elements, with two of the transposable elements not containing the transgene. The transposable elements which do not include the gene expression systems are much shorter than the other two transposable elements. In general, transposases will be more effective at cutting out shorter sequences so that, where a transposon has one 5' repeat and two 3' repeats, for example, the most common transposon that will be observed transferring to another locus will be the shorter, formed by the 5' repeat together with the more proximal of the two 3' repeats. Thus, as the transposons which do not contain the transgene are shorter than those which do, excision of the transposons which do not include the transgene occurs with greater frequency than excision of the transposons which do contain the transgene.

In some embodiments, the two internal piggyBac ITRs are modified to include about 160 base pairs of additional subterminal piggybac sequence. This additional sequence may be added in order to ensure that the shorter transposons (i.e. those not containing the transgene) are excised during subsequent rounds of exposure to transposase.

In preferred embodiments, the construct comprises four piggyBac inverted repeats forming at least two pairs of opposing inverted repeats. The four piggyBac inverted repeats consist of the nucleotide sequences represented by SEQ ID NOs: 30-32, with the sequence represented by SEQ ID NO: 30 being used for two of the piggyBac inverted repeats. In particular, one external inverted repeat consists of the nucleotide sequence represented by SEQ ID NO: 30 and the other external inverted repeat consists of the nucleotide sequence represented by SEQ ID NO: 31. One of the internal piggyBac repeats consists of the nucleotide sequence represented by SEQ ID NO: 30 and the other internal piggyBac inverted repeat consists of the nucleotide sequence represented by SEQ ID NO: 32. More specifically, the 5' external piggyBac repeat consists of the nucleotide sequence represented by SEQ ID NO: 30, and a 3' internal piggyBac inverted repeat consisting of the nucleotide sequence represented by SEQ ID NO: 32 is between the 5' external piggyBac inverted repeat and the transgene. The 3' external piggyBac inverted repeat consists of the nucleotide sequence represented by SEQ ID NO: 31, and a 5' internal piggyBac inverted repeat consisting of the nucleotide sequence represented by SEQ ID NO: 30 is between the 3' external piggyBac inverted repeat and the transgene.

Accordingly, the four transposons possible in such embodiment are between:

i) the 5' external and 3' external piggyBac inverted repeats, ii) the 5' external and 3' internal piggyBac inverted repeats, iii) the 3' external and 5' internal piggyBac inverted repeats, and iv) the 5' internal and the 3' internal piggyBac inverted repeats.

As described above, transposons ii) and iii) do not contain the transgene, and are shorter than transposons i) and iv).

In some embodiments having four inverted repeats, the construct further comprises at least one genetic marker associated with at least one possible transposon in order to allow the user to follow the progress of the various steps of transposition and excision and to determine in which individuals have been said steps have successful. In some embodiments, at least one genetic marker is associated with an identifiable step in the transposition/excision process, and more preferably, the marker is associated with the transgene. Such markers associated with the transgene may be as described above.

Preferably, at least one genetic marker is associated with each possible transposon. Accordingly, at least one genetic marker is positioned between each pair of inverted repeats. It will be appreciated that any suitable genetic marker may be used, and examples of such markers include DsRed2, AmCyan and ZsGreen. In some embodiments, the construct comprises three genetic markers, wherein one marker is positioned between each pair of inverted repeats. It will be appreciated that, in order to distinguish between the transposons, each of the markers must be different.

It will be understood by those skilled in the art that embodiments comprising at least one genetic marker will also comprise a promoter to drive the expression of the genetic marker. In some embodiments, the promoter is Hr5/IE1 (Choi & Guarino, 1995), while in other embodiments the promoter is Polyubiquitin (Handler & Harrel, 2001). However, promoters for use with the genetic marker are not limited to these two examples, and others may be used. Those skilled in the art will recognise which promoters are suitable.

Figure 2:
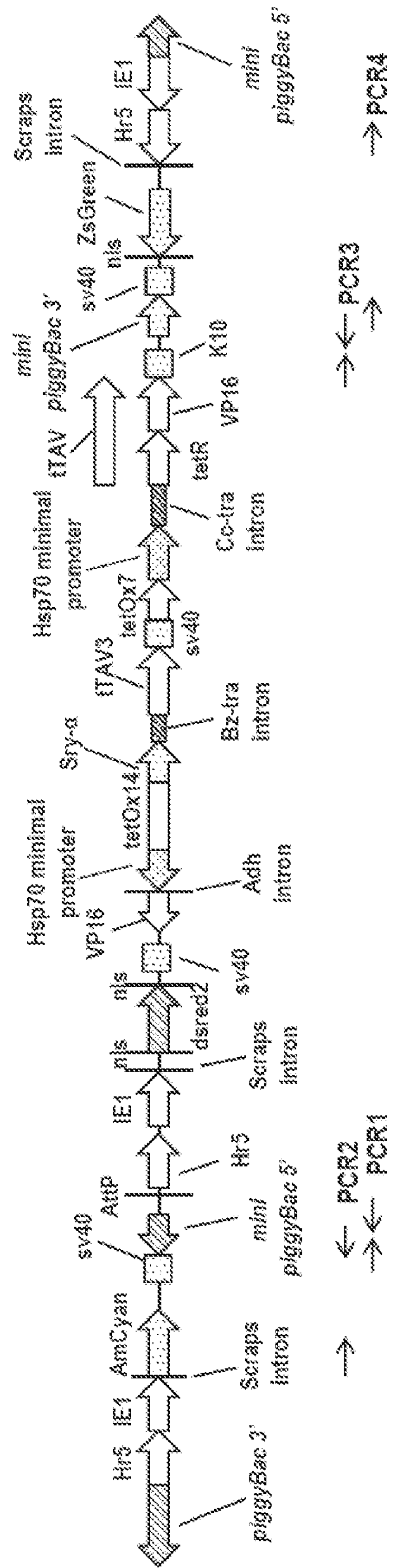
FIG. 2 is a schematic representation of one embodiment of the genetic construct of the invention.

In preferred embodiments, the construct comprises the transgene represented by SEQ ID NO:1 and further comprises four piggyBac inverted repeats as described above. The construct further comprises a genetic marker between the 5' external piggyBac repeat and the 3' internal piggyBac repeat, and a genetic marker between the 3' external piggyBac repeat and the 5' internal piggyBac repeat, wherein one of these genetic markers is AmCyan and the other is ZsGreen. In particularly preferred embodiments, the construct is as shown in FIG. 2, wherein the marker between the 5' external piggyBac repeat and the 3' internal piggyBac repeat is ZsGreen, and the marker between the 3' external piggyBac repeat and the 5' internal piggyBac repeat is AmCyan.

As mentioned above, the transgene and genetic construct of the invention are useful in the control of organism populations in the wild. Specifically, arthropods transformed with the transgene show sex-specific lethality, with improved transgene penetrance and earlier onset of lethality as compared to previously disclosed transgenic insects. The transformation of arthropods with any of the transgene or constructs above also provides a safety mechanism in the event of biochemical resistance. Constructs further comprising at least four inverted repeats, as described above, provide the further advantage that post-integration elimination of all transposon sequences is possible, leading to stability in both mass-rearing and field conditions.

Thus, in another aspect of the present invention, there are provided organisms transformed with a transgene or a construct as described above. In some embodiments, the organism is an arthropod. In some embodiments, the organism is an insect. In some embodiments, the organism is of the order Lepidoptera, Siphonaptera, Diptera, Hymenoptera, Coleoptera, Thysanoptera, Hemiptera, Orthoptera or Mesostigmata. In other embodiments, the organism is of the family Tephritidae, Drosophilidae, Lonchaeidae, Pallopteridae, Platystomatidae, Pyrogotidae, Richardiidae or Ulidiidae. In preferred embodiments, the organism is of the family Tephritidae or Drosophilidae. In preferred embodiments, the organism is of the genus *Ceratitis, Drosophila, Bactrocera, Anastrepha* or *Rhagoletis*. More preferably, the organism is of the genus *Ceratitis*. In particularly preferred embodiments, the organism is *Ceratitis capitata*.

It will be appreciated that the transgene or construct may be administered by any means known to those skilled in the art, but generally tested after integrating into the genome. Administration can be by known methods in the art, such as parenterally, intra-venous intra-muscularly, orally, transdermally, delivered across a mucous membrane, and so forth. Injection into embryos is particularly preferred. In some embodiments, the transgene or construct is administered as a plasmid.

In preferred embodiments, the transformed organism is *Ceratitis capitata*, and the transformed insect comprises the sequence represented by SEQ ID NO: 2 or 3. In particularly preferred embodiments, the transformed *Ceratitis capitata* comprises the sequence represented by SEQ ID NO: 2, and *Ceratitis capitata* comprising this sequence is herein referred to as OX3864A. In other embodiments, the transformed *Ceratitis capitata* comprises the sequence represented by SEQ ID NO: 3, and transformed *Ceratitis capitata* comprising this sequence is herein referred to as OX3647Q.

In some embodiments, a transformed *Ceratitis capitata* comprising the sequence represented by SEQ ID NO: 2 (i.e. OX3864A) is particularly preferred for the following reasons:

i) The transgene penetrance is a 100% with one copy; i.e. as seen in the Examples, even at a heterozygous state all females died in the absence of tetracycline from the larval medium;

ii) The male:female ratio in the presence of tetracycline incorporated in the larval diet is 50:50 indicating good repressibility of the transgene expression in females (this is of importance for a cost-effective propagation of the strain in a rearing facility);

iii) OX3864A showed complete pre-pupal female lethality in the absence of tetracycline;

v) Expression of the red marker (DsRed2) is robust and sustainable. The marker is apparent at all developmental stages allowing for thorough Quality Control (QC) protocols in the mass-rearing facility and reliable monitoring in the field;

vi) Life history parameters are comparable to those of the wild type strain used for transformation, as shown in the Examples, indicating that 03864A has near wild-type fitness when reared on tetracycline;

vii) The inserted construct has been stabilised post-insertion by the removal of the vector piggyBac ends, such the transgene is fixed and heritable in the insect's genome.

It is also useful to identify organisms which have been successfully transformed with a transgene or construct as described above. Thus, in another aspect of the invention, there is provided methods for detecting an organism transformed with a transgene or construct as described above, and primers for use in said method. The method comprises a PCR-based assay for detecting a transformed organism, by amplifying a DNA sequence which overlaps the organism's genomic DNA flanking the inserted transgene and the transgene itself. The method comprises contacting a sample of DNA obtained from an organism with a primer pair specific for a transgene as described above inserted into the insect genome, wherein one primer in the pair is specific for a nucleotide sequence of the transgene and the other primer in the pair is specific for a genomic nucleotide sequence flanking the inserted transgene, and amplifying the sample of DNA. Thus, one primer in a primer pair anneals the flanking genomic DNA and the other primer in the primer pair anneals the transgene. The amplification product may then be visualised, and may generally be detected using standard techniques known to those skilled in the art.

Amplification of the DNA sample is carried out using PCR techniques known to those skilled in the art. As mentioned above, the primers in the primer pair are specific to the transformed organism, such that only when the transgene is integrated in the relevant genomic position will a band of appropriate size amplify.

Those skilled in the art will appreciate that a variety of primers may be used in the method of the invention, and that such primers can be prepared using techniques known to those skilled in the art. The primers used will define the size of the PCR amplification product to be visualised or more generally detected.

In some embodiments, the method is for detecting an organism transformed with the transgene or genetic construct. In some embodiments, the organism is an arthropod. In some embodiments, the organism is an insect. In some embodiments, the organism is of the order Lepidoptera, Siphonaptera, Diptera, Hymenoptera, Coleoptera, Thysanoptera, Hemiptera, Orthoptera or Mesostigmata. In further embodiments, the organism is of the family Tephritidae, Drosophilidae, Lonchaeidae, Pallopteridae, Platystomatidae, Pyrogotidae, Richardiidae or Ulidiidae. In preferred embodiments, the organism is of the family Tephritidae or Drosophilidae. In other embodiments, the organism is of the genus *Ceratitis, Drosophila, Bactrocera, Anastrepha* or *Rhagoletis*. In preferred embodiments, the organism is of the genus *Ceratitis*. In particularly preferred embodiments, the organism is *Ceratitis capitata*.

In preferred embodiments, the method uses primers specific to a transformed *Ceratitis capitata*. In some embodiments, the primers specific to *Ceratitis capitata* comprising the nucleotide sequence represented by SEQ ID NO: 2. In this embodiment, a first primer pair (TG1), a second primer pair (TG2) or a third primer pair is provided. TG1 consists of the primers TG1-3864AttpflR (SEQ ID NO: 4) and TG1-AttPF2, (SEQ ID NO: 5). In this pair, TG1-3864AttpflR is specific for the genomic DNA flanking the transgene and TG1-AttPF2 is specific for the transgene itself. TG2 consists of the primers represented by SEQ ID NOs: 6 and 7. TG2 consists of primers TG2-3864FRTFIF (SEQ ID NO: 6) and TG2-FRTNheF (SEQ ID NOs: 7). In TG2, TG2-3864FRTFIF is specific for the genomic DNA flanking the inserted transgene, and TG2-FRTNheF is specific for the transgene itself. The third primer pair consists of Cc3864FRTtaqF (SEQ ID NO: 10) and Cc3864FRTtaqR (SEQ ID NO: 11). In the third primer pair, Cc3864FRTtaqF is specific to the transgene and Cc3864FRTtaqR is specific to the flanking genomic DNA.

In other embodiments, any one of the primers specific to the transgene disclosed above may be paired with any one of the primers specific to the flanking genomic DNA, and a person skilled in the art will appreciate that the size of the PCR amplification product will depend upon the primer pairs used.

In other embodiments, the method for detecting an organism transformed with a transgene or construct as described above further comprises the use of a dual-labelled probe during the amplification steps.

The sequence at the junction of the integrated transgene and the organism genomic DNA presents a unique fingerprint. Thus, it is possible to detect a unique junction using three specific oligonucleotides. Two of the oligonucleotides used in the method are primers to allow for the amplification of a predetermined fragment of inserted transgene and flanking genomic DNA, to which a third, dual-labelled, oligonucleotide, i.e. the probe, anneals. In some embodiments, the probe comprises a quencher molecule and a 5' reporter molecule.

In some embodiments, the method comprises the steps of contacting a sample of DNA obtained from an organism with a primer pair specific for a transgene as described above inserted into the organism genome, wherein one primer in the pair is specific for the transgene and the other primer in the pair is specific for a genomic nucleotide sequence flanking the inserted transgene, and amplifying the sample of DNA. This step of the method is largely as described above. The probe is added to the PCR amplification mixture with the primers. The probe specifically bridges the junction of the transgene and flanking DNA in the amplified PCR product, requiring this boundary for a positive output. At each step of PCR-amplification, the 5'-3' exonuclease activity of Taq polymerase releases a 5' reporter molecule (FAM) from the annealed probe, resulting in an accumulative emission that is detectable in a real time PCR machine in samples bearing the integrated transgene. Thus, the method further comprises the steps of contacting the DNA sample with a probe during PCR amplification of the DNA sample.

In some embodiments, the organism is an arthropod, and preferred arthropods have been discussed above. In preferred embodiments, the organism is an insect, preferably a tephritid, more preferably of the genus *Ceratitis*. In particularly preferred embodiments, the insect is of the species *Ceratitis capitata*. Thus, in such embodiments, the primers are specific to a transformed *Ceratitis capitata*. Preferably, the primers are specific to *Ceratitis capitata* comprising the sequence represented by SEQ ID NO: 2 (i.e. OX3864A). In this embodiment, the primers allowing for the amplification of a predetermined fragment are Cc3864FRTtaqF and Cc3864FRTtaqR, represented by SEQ ID NOs: 10 and 11 respectively. Cc3864FRTtaqF is specific for the flanking genomic DNA and Cc3864FRTtaqR is specific for the transgene. In such embodiments, the probe is Cc3864FRTprobe, as represented by SEQ ID NO: 12.

In a further aspect of the present invention, there is provided a method for the population control of an organism. In preferred embodiments, the method comprises the step of transforming an organism or organisms with a transgene or construct as described above. In some embodiments, the method further comprises releasing said transformed organism(s) into the population to be controlled. In further embodiments, the method may also comprise the step of monitoring the population to be controlled. The released organisms breed with the population to be controlled, and the female-specific lethality conferred by the gene expression systems means that the female progeny produced by such cross-breeding will die during early stages of development. The male progeny inheriting the gene expression systems survive to pass on the lethal phenotype to subsequent generations.

In some embodiments, the population to be controlled is an arthropod population. In some embodiments, the population is an insect population. In some embodiments, the population is of the order Lepidoptera, Siphonaptera, Diptera, Hymenoptera, Coleoptera, Thysanoptera, Hemiptera, Orthoptera or Mesostigmata. In other embodiments, the population is of the family Tephritidae, Drosophilidae, Lonchaeidae, Pallopteridae, Platystomatidae, Pyrogotidae, Richardiidae or Ulidiidae. In preferred embodiments, the population is of the family Tephritidae or Drosophilidae. In further embodiments, the population is of the genus *Ceratitis, Drosophila, Bactrocera, Anastrepha* or *Rhagoletis*. In preferred embodiments, the population is of the genus *Ceratitis*. In some embodiments, the population is a population of *Ceratitis capitata.*

The release of organisms may be by any method known to those skilled in the art, for example, by a method such as cage release or paperbag release, such as those described in Simmons et al. (2011) or Harris et al. (2011).

The step of monitoring the population of organisms may be by any method known to those skilled in the art. In some embodiments, the transgene inserted into the transformed organism(s) includes a genetic marker, such as DsRed2. Thus, monitoring of the population to be controlled may be by trapping insects from the population, after release of the transformed organism(s) and visualisation, or, more generally, detection, for the genetic marker in the trapped individuals.

The invention will now be illustrated with reference to the following, non-limiting Examples.

EXAMPLES

Example 1: Selection of the Lead Product *C. capitata* Strain

Transformed strains were generated through piggyBac-mediated transformation using the construct shown in FIG. 2 of the Toliman (Origin: Guatemala) colonised *C. capitata* strain. Backcrossing to wild-type flies yielded multiple transgenic lines (Table 1). 49 G0 adults were obtained for OX3864 (a survival rate of 21%), and 950 for OX3647 (35% survival).

The sex ratio under these two diet conditions was used to assess functionality of the construct in two crucial parameters: 1) total suppression of female lethality when fed tetracycline, and 2) full female lethality in the absence of tetracycline. Lines were selected for further testing based on their ability to meet these parameters and on the strength of fluorescence.

Figure 4:
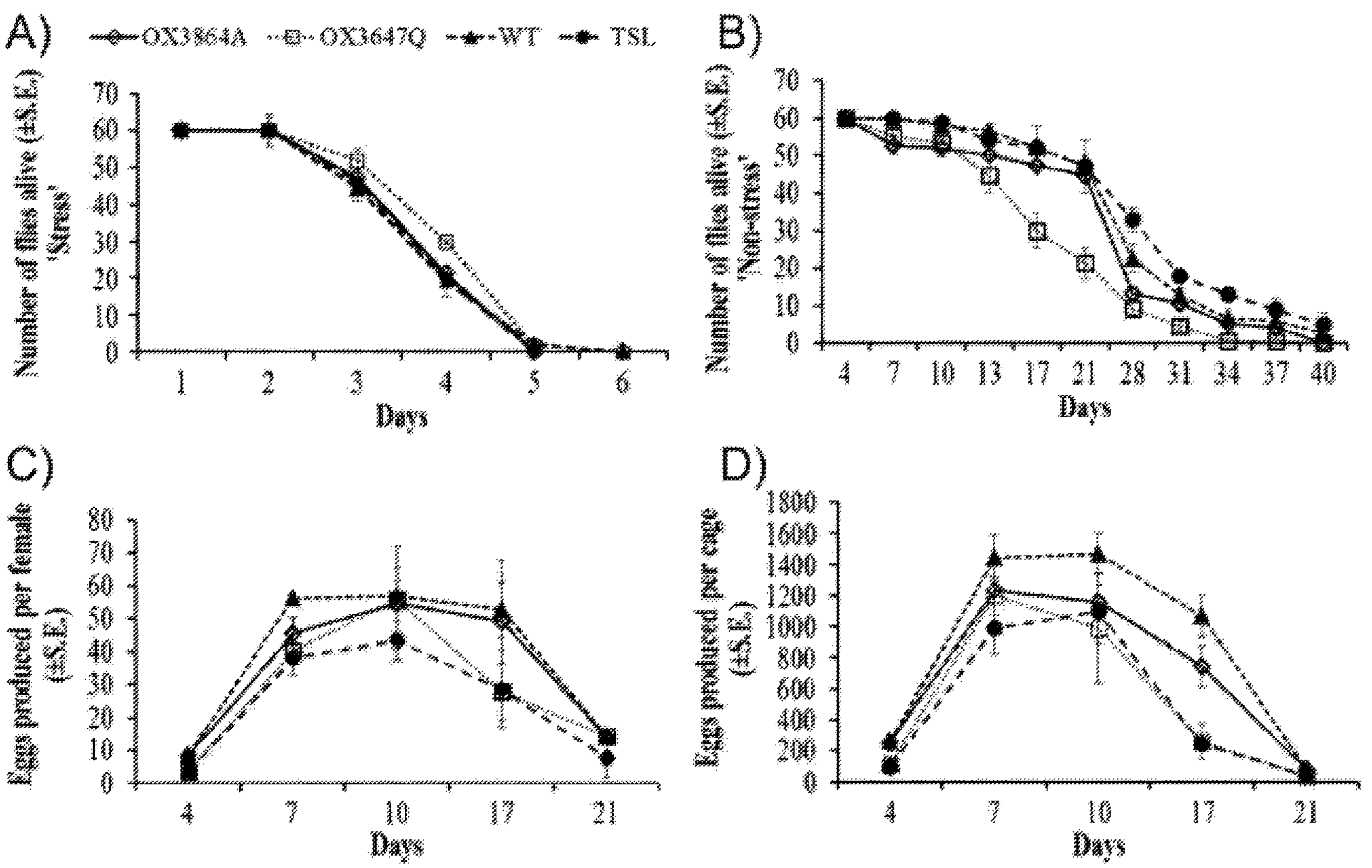
FIG. 4 shows graphs of 7 parameters. Panel A is a graph showing the survival of transformed *C. capitata* under "stress test" conditions, i.e. without food or water post-eclosion. Adult male and female survival data ware combined (n=180). Panel B is a graph showing survival under non-stressed conditions of ad libitum food and water (n=180). Panel C is a graph showing individual female lifetime fecundity. Panel D is a graph showing female lifetime egg productivity, showing the average production from three cages of 30 females over 3 weeks. is a graph showing hatching rates of eggs laid by the females in Panel C. Panel F is a photograph showing DsRed2 fluorescence in males of transformed strains OX3864A (right) and OX3647Q (middle) as compared to wild type males (left). Panel G is a photograph of the same adult males as in Panel F under white light.
Figure 4:
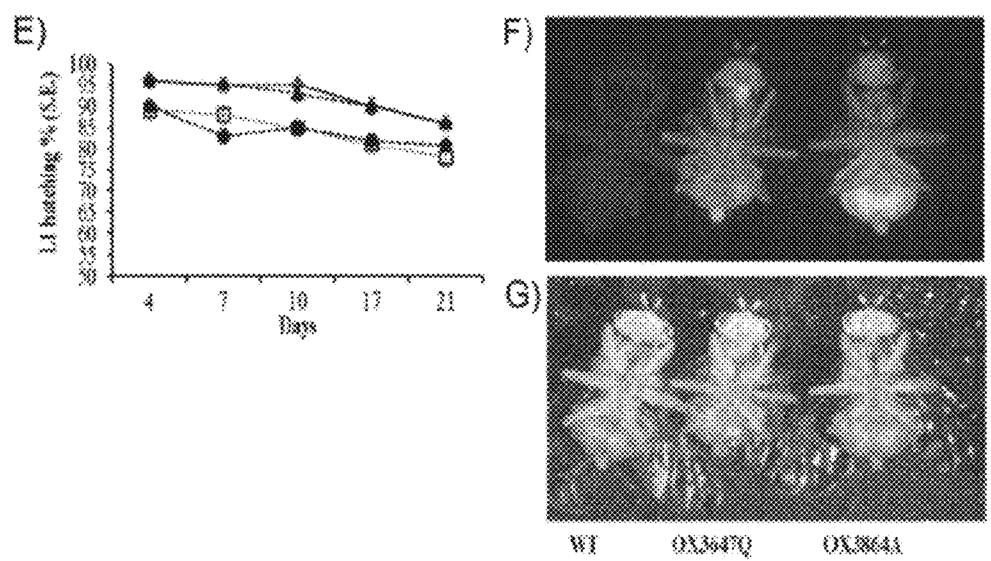

11 lines failed to provide complete penetrance with a single copy of the transgene and were discarded. One line demonstrated incomplete tetracycline repressibility and was also discarded. Two lines did not produce enough progeny, possibly due to fitness penalties imposed by the transgene insertion, and were therefore discontinued. Fluorescence was good in all lines generated; however, construct OX3864 provided in general a stronger and clearer fluorescence phenotype. Photographs of OX3864A and OX3647Q adult male flies can be seen in FIGS. 4F and 4G. Although both of these strains display a recognisable phenotype compared to WT males, it is apparent that the OX3864A fluorescent phenotype (+++) is stronger than that of OX3647Q (++).

TABLE 1

G2 survival analysis of males and females from different OX lines on- and off-tetracycline microinjection survivors (G0) were pooled (either 10 males or 20 females) before being crossed to the TOLIMAN wt. Lines were named according to a number and an alphabetical suffix (e.g. OX3647 Q) to denote the pool from which the G1 offspring were collected. Because of the very high number of OX3647 survivors, the alphabet system was re-used and denoted by a number in parentheses before the alphabetical suffix, e.g. OX3647(2)B. Additional numbers were given to multiple G1 offspring emerging from the same pool (e.g. OX3647 L1, L2) and these were treated initially as potentially separate insertion events. Single transgenic G1 males were each crossed with several virgin wild type females. The G2 progeny were scored for fluorescence (F) or non-fluorescence (NF) and by sex, on tetracycline- (T, 100 μg/ml) or non-tetracycline (NT) containing media.

| | T food | | | | | | NT food | | | | | |
|---|---|---|---|---|---|---|---|---|---|---|---|---|
| | Pupae | | F adults | | NF adults | | Pupae | | F adults | | NF adults | |
| Line | F | NF | ♂ | ♀ | ♂ | ♀ | F | NF | ♂ | ♀ | ♂ | ♀ |
| 3647L1 | 61 | 46 | 5 | 7 | 10 | 2 | 106 | 81 | 0 | 107 | 81 | 0 |
| 3647L2 | 89 | 106 | 41 | 41 | 35 | 44 | 63 | 60 | 33 | 37 | 28 | 37 |
| 3647L3 | 307 | 223 | 55 | 232 | 178 | 21 | 87 | 93 | 8 | 82 | 92 | 1 |
| 3647G | 17 | 26 | 11 | 6 | 10 | 15 | 72 | 58 | 16 | 16 | 29 | 27 |
| 3647M1 | 79 | 32 | 23 | 39 | 24 | 0 | 97 | 60 | 6 | 70 | 47 | 0 |
| 3647M2 | 76 | 2 | 27 | 37 | 1 | 1 | 76 | 17 | 39 | 34 | 4 | 12 |
| 3647M3 | 47 | 47 | 0 | 42 | 43 | 1 | 46 | 27 | 0 | 46 | 26 | 1 |
| 3647Q | 107 | 88 | 49 | 45 | 36 | 32 | 122 | 302 | 92 | 0 | 125 | 112 |
| 3647P | 199 | 199 | 92 | 88 | 84 | 72 | 61 | 96 | 21 | 0 | 24 | 25 |

TABLE 1-continued

G2 survival analysis of males and females from different OX lines on- and off-tetracycline microinjection survivors (G0) were pooled (either 10 males or 20 females) before being crossed to the TOLIMAN wt. Lines were named according to a number and an alphabetical suffix (e.g. OX3647 Q) to denote the pool from which the G1 offspring were collected. Because of the very high number of OX3647 survivors, the alphabet system was re-used and denoted by a number in parentheses before the alphabetical suffix, e.g. OX3647(2)B. Additional numbers were given to multiple G1 offspring emerging from the same pool (e.g. OX3647 L1, L2) and these were treated initially as potentially separate insertion events. Single transgenic G1 males were each crossed with several virgin wild type females. The G2 progeny were scored for fluorescence (F) or non-fluorescence (NF) and by sex, on tetracycline- (T, 100 μg/ml) or non-tetracycline (NT) containing media.

| | T food | | | | | | NT food | | | | | |
|---|---|---|---|---|---|---|---|---|---|---|---|---|
| | Pupae | | F adults | | NF adults | | Pupae | | F adults | | NF adults | |
| Line | F | NF | ♂ | ♀ | ♂ | ♀ | F | NF | ♂ | ♀ | ♂ | ♀ |
| 3647(2)B | 138 | 188 | 61 | 46 | 90 | 71 | 207 | 380 | 171 | 0 | 185 | 159 |
| 3647(2)C1 | 139 | 146 | 53 | 66 | 66 | 58 | 105 | 132 | 63 | 0 | 65 | 65 |
| 3647(2)C2 | 196 | 299 | 95 | 83 | 121 | 127 | 152 | 217 | 132 | 0 | 152 | 142 |
| 3647(2)J | 240 | 196 | 133 | 88 | 83 | 84 | 177 | 231 | 108 | 0 | 92 | 102 |
| 3647(2)W | 194 | 168 | 80 | 82 | 66 | 66 | 141 | 185 | 79 | 0 | 84 | 84 |
| 3647(3)C(?) | 305 | 175 | 125 | 2 | 42 | 50 | 11 | 29 | 8 | 0 | 8 | 12 |
| 3647(3)C(?) | 271 | 321 | 152 | 0 | 0 | 153 | 49 | 45 | 48 | 0 | 1 | 44 |
| 3647(3)F(?) | 105 | 150 | 32 | 37 | 44 | 33 | 66 | 79 | 29 | 18 | 33 | 30 |
| 3647(3)$F_2$ | 71 | 70 | 16 | 17 | 23 | 13 | 28 | 34 | 10 | 0 | 12 | 15 |
| 3647(3)G | 181 | 185 | 51 | 55 | 50 | 50 | 132 | 63 | 49 | 41 | 30 | 19 |
| 3647(3)H(?) | 120 | 19 | 49 | 32 | 54 | 39 | 33 | 33 | 13 | 1 | 17 | 8 |
| 3647(3)H(?) | 124 | 89 | 40 | 40 | 32 | 29 | 1 | 43 | 44 | 0 | 27 | 33 |
| 3647(3)$J_1$ | 12 | 23 | 3 | 0 | 12 | 4 | 21 | 19 | 9 | 0 | 7 | 5 |
| 3647(3)$J_2$ | 39 | 52 | 12 | 7 | 14 | 8 | 4 | 20 | 4 | 0 | 11 | 9 |
| 3647(3)K | 2 | 1 | 0 | 0 | 0 | 0 | 1 | 5 | 1 | 0 | 2 | 3 |
| 3647(3)O(?) | 105 | 47 | 18 | 79 | 43 | 0 | 67 | 54 | 28 | 36 | 34 | 0 |
| 3647(3)$P_1$ | 1 | 2 | 0 | 1 | 0 | 1 | 0 | 0 | 0 | 0 | 0 | 0 |
| 3647(3)$P_2$ | 44 | 66 | 11 | 17 | 13 | 18 | 38 | 62 | 15 | 1 | 18 | 21 |
| 3647(3)$Q_1$ | 68 | 96 | 24 | 18 | 17 | 23 | 31 | 52 | 11 | 0 | 18 | 34 |
| 3647(3)$Q_2$ | 27 | 13 | 14 | 8 | 5 | 6 | 0 | 0 | 0 | 0 | 0 | 0 |
| 3647(3)$R_1$ | 88 | 116 | 38 | 50 | 61 | 58 | 77 | 158 | 20 | 0 | 65 | 44 |
| 3647(3)$R_2$ | 38 | 44 | 24 | 0 | 10 | 42 | 1 | 7 | 0 | 0 | 2 | 2 |
| 64A(?) | 351 | 369 | 176 | 160 | 177 | 168 | 60 | 124 | 50 | 0 | 35 | 34 |
| 64E(?) | 466 | 514 | 191 | 140 | 171 | 154 | 395 | 696 | 212 | 0 | 262 | 236 |

(?) indicates data missing or illegible when filed

Further analysis of the strains generated included:

a single transgene insertion originally measured as marker allele segregation in G2, potential for homozygosis measured as marker allele segregation when males and females of the same line were crossed together, piggyBac end removal via crossing to strain OX3133, which provides a source of transposase, following the method described by Dafa'alla et al. (2006).

Five lines exhibited multiple insertions, and for three lines the transgene insertion was found to be sex linked. All eight lines were, therefore, discarded. Strain OX3864E contained a silent insertion (confirmed by flanking sequence analysis) and was discarded. All remaining strains were positive for homozygosis potential and thus crossed to the medfly strain OX3133 for piggyBac excision (Dafa'alla et al., 2006). Only strains OX3864A and OX3647Q demonstrated complete removal of all piggyBac sequences and were thus selected as potential product strains.

Figure 3:
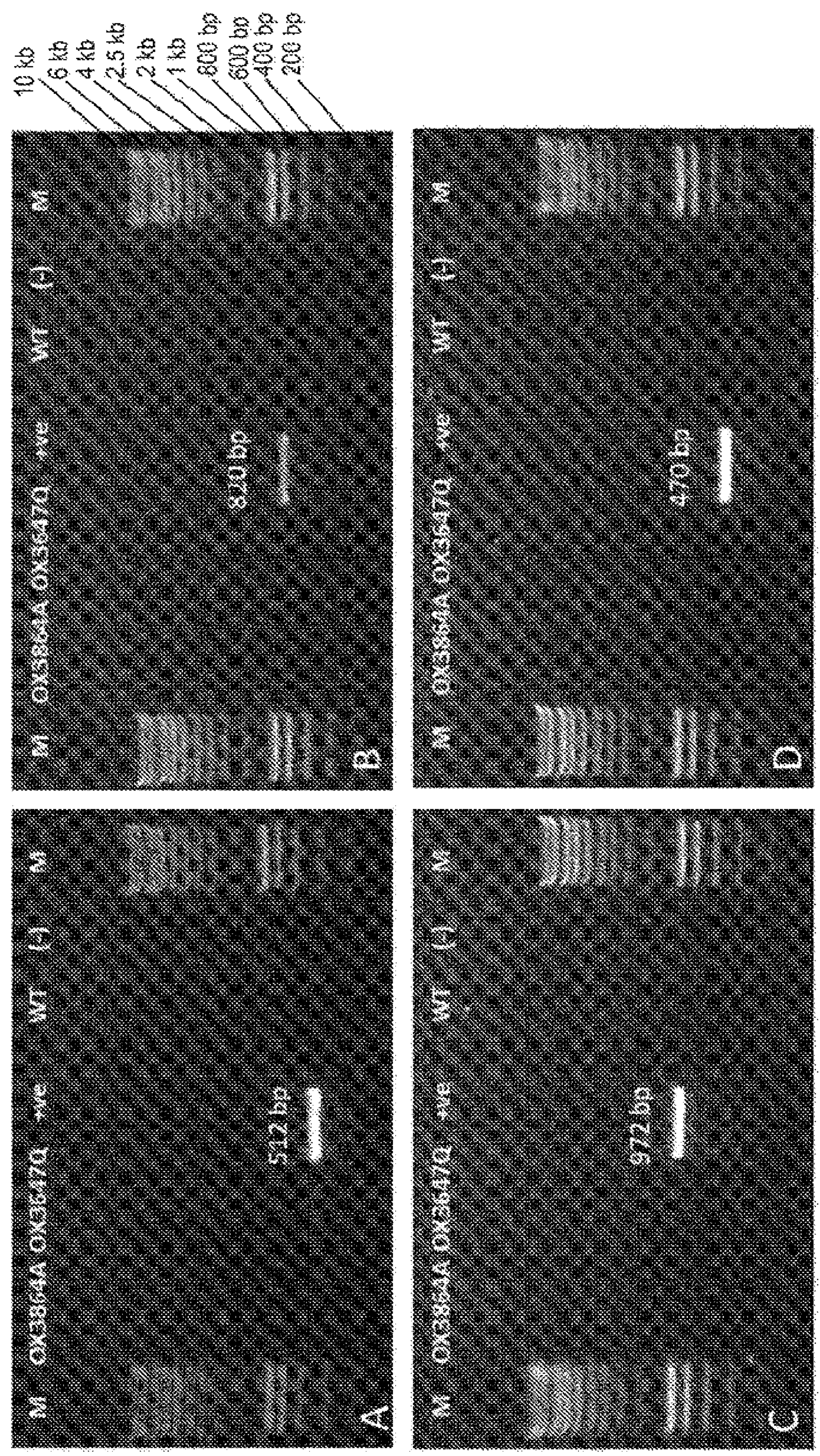
FIG. 3 shows photographs of gel runs from four PCR reactions (Panels A, B, C and D) which span the regions of the constructs where piggyBac sequences should have been removed via cassette exchange after crossing the OX3864A/OX3647Q strains with strain OX3133—a source of transposase—as described by Dafa'alla et al (2006).

Subsequently, homozygous lines of each of OX3864A and OX3647Q were derived by inbreeding to produce putative homozygotes, with confirmation by PCR. Further evidence for complete piggyBac sequence removal is provided by PCR (FIG. 3). As can be seen from FIG. 3, no piggyBac sequences were present in strains OX3864A and OX3647Q, as shown by the lack of gel product for resolved lines when using four PCRs designed to generate a product when piggyBac is present in the constructs. To produce the gels, genomic DNA was extracted from individual adults using the Purelink genomic DNA kit (Invitrogen) according to the manufacturer's instructions. PCR was carried out using Biotaq (PCR biosystems), according to manufacturer's instructions. PCR conditions were: initial denaturation at 94° C. for 2 min, followed by 10 cycles of 94° C. 15 s, 60° C. 30 s, decreasing by 0.5° C./cycle, and 72° C. 15 s, then 25 cycles of 94° C. 15 s, 55° C. 30 s, 72° C. 15 s, and a final elongation of 72° C. for 7 mins.

The PCR reaction resulting in the gel shown in panel A of FIG. 3 used primers 916) AttPF2 (GTCATGTCGGCGACCCTACGC; SEQ ID NO: 5) and TD935)Diag-5PBmin(GCCACCGAGTATGACCGGTAG; SEQ ID NO: 15). The presence of the piggyBac motif generates a DNA fragment of 512 bp. The PCR reaction resulting in the gel shown in panel B of FIG. 3 used primers TD222) Dlag-Pb5 (CTGATTTTGAACTATAACGACCGCGTG; SEQ ID NO: 16) and 432) AmCydiagF (TCACCTACGAGGACGGCGG; SEQ ID NO: 17). The presence of the piggyBac motif generates a DNA fragment of 820 bp. The PCR reaction resulting in the gel shown in panel C of FIG. 3 used primers TD1445)Dlag6-pb3 (GTGCCAAAGTTGTTTCTGACTGAC; SEQ ID NO: 18) and TD154)Dlag-K10-1(CACTTAAGCGACAAGTTTGGCCAAC; SEQ ID NO: 19). The presence of the piggyBac motifs generates a DNA fragment of 972 bp. The PCR reaction resulting in the gel shown in panel D of FIG. 3 used primers TD1312)Diag7-pb3

(CCCTAGAAAGATAATCATATTGTGACG; SEQ ID NO: 20) and TD677)Diag2-hr5 (CATACTTGATTGTGTTTTACGCGTAG; SEQ ID NO: 21) the presence of the piggyBac motifs generates a DNA fragment of 470 bp. PCR products from OX3864A, OX3647Q an unresolved positive control OX3647 and two negative controls (wt TOLIMAN and water) were run on a 1% gel with a smart ladder (Eurogentec, band sizes top to bottom: 10 kb, 8 kb, 6 kb, 5 kb, 4 kb, 3 kb, 2.5 kb, 2 kb, 1.5 kb, 1 kb, 800 bp, 600 bp, 400 bp, 200 bp).

Following insertion and excision analysis, strains OX3864A and OX3647Q were further tested for life history parameters in comparison to the TOLIMAN wild-type strain that they were both derived from and also the temperature-sensitive-lethal (tsl) Vienna 8 strain (reference). tsl is the genetic sexing strain T(Y;5)101 called also Vienna-8 (without the pericentric inversion D53) (Caceres, 2002), introgressed into the TOLIMAN wt that is currently used in many Sterile Insect Technique (SIT) programmes worldwide. Details of the tests performed are given below. Graphs are presented in FIG. 4. Fitness indices are given in Table 2.

Longevity

Longevity tests were performed at 21° C. and a relative humidity (R.H.) 50% in six replicate plastic cages (9 cm×9 cm×9 cm), each containing 30 males and 30 females of the same genotype (1 insect/8.1 $cm^2$). Three of the cages were randomly assigned to a "stress" test of no food and no water. This was done to assess relative measures of nutrient reserves available at eclosion, an important indicator of potential longevity under release conditions. The remaining cages had an ad libitum supply of food and water. Cages were monitored on a daily basis; dead adults were removed and sexed, until all flies were dead, in line with FAO/IAEA/USDA guidelines.

Flies held under the stress conditions had, significantly reduced life spans compared to those provided with food and water (Log Rank Test $\chi^2_1$=1307, P<0.001); all stressed flies were dead within six days (FIG. 4D). In the non-stress cages given food and water, there were significant effects on survival of genotype (i.e. RIDL versus wild type and tsl; $\chi^2_3$=15.6, P<0.001; FIG. 4B). Sex had no significant effect on longevity ($\chi^2_1$=0.17, P=0.68), and therefore the survival data for both sexes were combined. Under stress conditions, OX3647Q showed significantly higher survival in both sexes in comparison to the wt (Means±standard error: wt=4.1 days±0.054; OX3647Q=4.38 days±0.066; Cox's Proportional Hazards: z=−2.1, P=0.035). However, the pattern under full food, non-stressed conditions was reversed (wt=18.9 days±0.52; OX3647Q=13.7 days±0.53; z=5.92, P<0.01). There was no significant difference in the average lifespan of OX3864A and tsl flies in comparison to the wt for either the stressed or non-stressed treatments, (stressed treatment: OX3864A=4.13 days±0.055; z=0.59, P=0.55, tsl=4.13 days±0.064; z=0.53, P=0.33; full food, non-stressed treatment: OX3864A=17.2 days±0.53; z=1.13, P=0.26, tsl=17.0 days±0.52; z=0.7, P=0.49).

Lifetime Female Fecundity

From the non-stressed cages described above, eggs were collected over 24 hour periods and counted under a dissecting microscope. The egg samples were then incubated on wet Whatman filter paper (Fisher Scientific) and sealed into a Petri dish with parafilm (200 eggs per Petri dish, 600 eggs per line in total). 72 hours after egg collection, Petri dishes were unsealed and examined under a dissection microscope in order to count the number of empty versus unhatched egg casings.

Per-cage daily egg production from the "non-stressed" cages declined significantly over time (Repeated Measures ANOVA: $F_{1.6,\ 12.9}$=253.04, P<0.001) and there was a significant effect of genotype ($F_{4.8,\ 12.9}$=5.19, P=0.008). Pairwise comparisons with a Bonferroni correction revealed that significantly fewer eggs were produced over the lifetime for both RIDL and tsl lines in comparison to the wt (wt mean lifetime egg production=4315±48.51; OX3864A=3470±226, P<0.014; OX3647Q=2593±147, P<0.001; tsl=2465±93.29, P<0.001). OX3647Q and tsl strains also produced significantly fewer eggs than OX3864A (OX3647Q vs. wt, P<0.001; tsl versus wt, P=0.005, FIG. 4D).

By recording daily mortality it was also possible to estimate age-specific egg-production per female. Consistent with the above, this also showed that fecundity declined significantly with time (Repeated Measures ANOVA: $F_{1.9,\ 15.2}$=131.85, P<0.001). However, there was no significant effect of genotype on this decline ($F_{5.7,\ 15.2}$=2.19, P=0.104, FIG. 4C). Supporting this, a one-way ANOVA on the number of eggs laid at peak fecundity (day 10), also revealed no significant differences in egg-laying per female between any of the lines ($F_{3,\ 8}$=0.029, P=0.97).

Egg Hatching Rates

There was a significant effect of age on egg hatching rates (Repeated Measures ANOVA $F_{5,40}$=207.3, P<0.001), as well as a significant effect of genotype ($F_{15,40}$=4.52, P<0.001, FIG. 4E). Pairwise comparisons with a Bonferroni correction showed that OX3647Q and tsl, but not OX3864A, had mean percentage egg hatching rates that were significantly lower than the wt (wt=89.56%±0.84; OX3647Q=79.11%±0.84, P<0.001; tsl=78.33%±0.84, P<0.001; OX3864A=87.11%±0.84, P=0.247).

Adult Eclosion Rates 300 pupae from each line were kept singly and monitored for eclosion. Adults were checked for sex and visible deformity before recording. Uneclosed or partially enclosed pupae casings were counted and then discarded.

There was also a significant difference in adult eclosion rates between lines (ANOVA: $F_{3,\ 10}$=9.89, P<0.001). A Tukey HSD post hoc test revealed that this was mostly attributable to a significantly lower adult eclosion rate in OX3647Q in comparison to wt (wt=86.1%±0.69; OX3647Q=75.7%±2.43, P<0.01; OX3864A=84.7%±0.91, P=0.9; tsl=81.2%±1.04, P=0.25). There was a significant effect of genotype on adult sex ratio ($F_{3,\ 10}$=5.06, P=0.036), attributable to a difference in the sex ratio of males to females in OX3647Q but not in the other lines (Tukey HSD post hoc tests: wt=47%±1.8; OX3647Q=54%±1, P=0.035; OX3864A=55%±2.3, P=0.055; tsl=50%±1.5, P=0.83).

Fitness Indices

From the individual life history components, the net reproductive rate per female ($R_0$) and average generation time (G) (spanning the peak of female fertility from one generation to the next) were calculated (Table 2). From these estimates, an index of fitness (r) per female was then derived. The r value for the wt was 0.195, which equates to each female contributing on average 0.195 females per day to the next generation. The other lines had lower fitness indices (OX3864A: r=0.187, OX3647Q: r=0.176, tsl: r=0.165).

TABLE 2

Indices of Fitness for strains OX3864A, OX3647Q, wild type and tsl, calculated from the life history data.

| | WT | OX3864A | OX347Q | TSL |
|---|---|---|---|---|
| Net Reproductive Rate ($R_0$) of Females | 267.6 | 183.7 | 113.1 | 133.1 |
| Generation time in days (G) | 32 | 32.1 | 35.6 | 36 |
| Index of fitness (r) | 0.195 | 0.187 | 0.176 | 0.165 |

Mating Competitiveness of OX3864A and OX3647 Males with Wild Type TOLIMAN Flies

Adult OX3864A, OX3647Q, TOLIMAN wt were obtained from larvae reared off-tet at low density (1 larva/0.5 g medium). Field cages (1.25 m tall with a base of 0.5 $m^2$) were constructed inside a greenhouse at the Zoology Department, Oxford University (Oxford, UK), with small orange trees (~1 m in height) placed inside, experiments took place during August (sunrise 06.00) utilizing natural light and a stable temperature and humidity (25° C., 50% R.H.). 30 males from either OX3864A or OX3647Q were placed together with 30 wt males at 06:30, and 30 females introduced 30 minutes later.

The basic sequence of courtship and copulation is well characterised in the medfly, and follows a distinct sequence of male behaviour patterns (Cayol et al., 2002), consisting of "pheromone calling" and rapid wing vibrations. After courting the male will leap onto the female and if successful intromission occurs, the pair will generally remain still. Copulation generally lasts between 90 to 195 minutes. Mating pairs were removed from cages following intromission, and carefully introduced into horizontally-placed 1.5 ml eppendorfs. Copulation initiation time was recorded and copulations were scored as successful only if the pair mated for >30 minutes after transfer to the eppendorf. Short copulations (<15 minutes) were eliminated from the data as they often result in no sperm transfer. The mating experiments ended 9 hairs after initiation (16:00) or whenever all females had copulated, whichever was sooner. The identity of the mating males was determined by scoring males for the presence or absence of the DsRed2 fluorescent marker under a fluorescence microscope. Tests were performed with 10 replicates for each line. 167 and 237 couples were assessed for OX3864A and OX3647Q, respectively.

The relative sterility index (RSI) was used as a measure of male sexual competitiveness (McInnis et al., 2002; FAO/IAEA/USDA, 2003). RSI ranges between 0 and 1, a RSI of 1 would represent 100% of matings by transgenic males, a value of 0, 100% with the wt and 0.5 representing equal numbers of matings. The results showed that neither transgenic strain showed a significant reduction in competitiveness relative to wt males (t-test: OX3864A: RSI 0.46±0.08, $t_{18}$=−2.09, OX3864A mated males n=77, wt mated males n=90, P=0.05; OX3647Q: RSI 0.47±0.09, $t_{18}$=−1.72, OX3647Q mated males n=112, wt mated males n=125, P=0.1).

No significant differences in female remating frequency between females initially mated with either wt or fsRIDL males were seen (Fisher's Exact test: OX3864A: $\chi^2_1$=0.82, n=40, P=0.775; seven females first mated to OX3864A males remated, eight females first mated to wt males remated; OX3647Q: $\chi^2_1$=0, n=40, P=1, 12 females first mated to OX3647Q males remated and 12 females first mated to wt males remated). For those females that did re-mate when first mated to a RIDL male, the genotype of the second male had no effect on remating frequency (OX3864A: $\chi^2_1$=0.58, P=0.4 (females that first mated with OX3864A then remated with wt n=3, remated with OX3864A n=4; females that first mated with wt then remated with wt n=5, remated with OX3864A n=3); OX3647Q: $\chi^2_1$=0.17, P=0.5 (females that first mated with OX3647Q then remated with wt n=6, remated with OX3647Q n=6, females that first mated with wt then remated with wt n=7, remated with OX3647Q n=5)).

Although both medfly strains displayed good rearing and mating characteristics compared to the tsl Vienna 8 strain and the wt TOLIMAN strain, strain OX3864A outperformed strain OX3647Q and was therefore selected as the lead Medfly product strain.

Example 2: Molecular Characteristics of Strain OX3864A

PCR-Based Assay for Specific Identification of Event OX3864A

In order to carry out quality control on the OX3864A strain and to monitor field use, an event-specific, PCR-based nucleotide detection assay was developed. The protocol for this assay is shown in Example 4, below, and the primers used are described in Table 3.

TABLE 3

| | |
|---|---|
| TG1-2864AttpflR-Flanking genomic primer | 5'-GCTGCCCATTGCTAAGGTTTGTG-3' (SEQ ID NO: 4) |
| TG1-AttPF2-5'-Transgene specific primer | GTCATGTCGGCGACCCTACGC-3' (SEQ ID NO: 5) |
| TG2-3864FRTFIF-Flanking genomic primer | 5'-CAACGAGTGACAGCAATGATATTCCTTA C-3' (SEQ ID NO: 6) |
| TG2-FRTNheF-Transgene specific primer | 5'-GGTGTGGCTAGCTCGAAGAAGTTCCTAT TCCGAAGTTCC-3' (SEQ ID NO: 7) |
| CcAdh2RTF-Cca Adh primer | 5'-GAAGCTGTTCGGGCTTCAGGC-3' (SEQ ID NO: 8) |
| CcAdh2RTR-Cca Adh primer | 5'-CTTGGAGGTGATGTCGAATTTGGTG-3' (SEQ ID NO: 9) |

Each transgene-detecting primer pair comprises one primer that anneals within the transgene and one that anneals in the flanking genomic DNA of OX3864. Thus, only when the transgene is integrated in the genomic position described for OX3864 will a band of the appropriate size amplify. Primer pairs TG1 and TG2 target the flanking DNA at the opposite ends of the transgene. A primer pair that amplifies a fragment of the endogenous Adh gene was used as a positive control to assure the quality of genomic DNA used in this assay.

Figure 5:
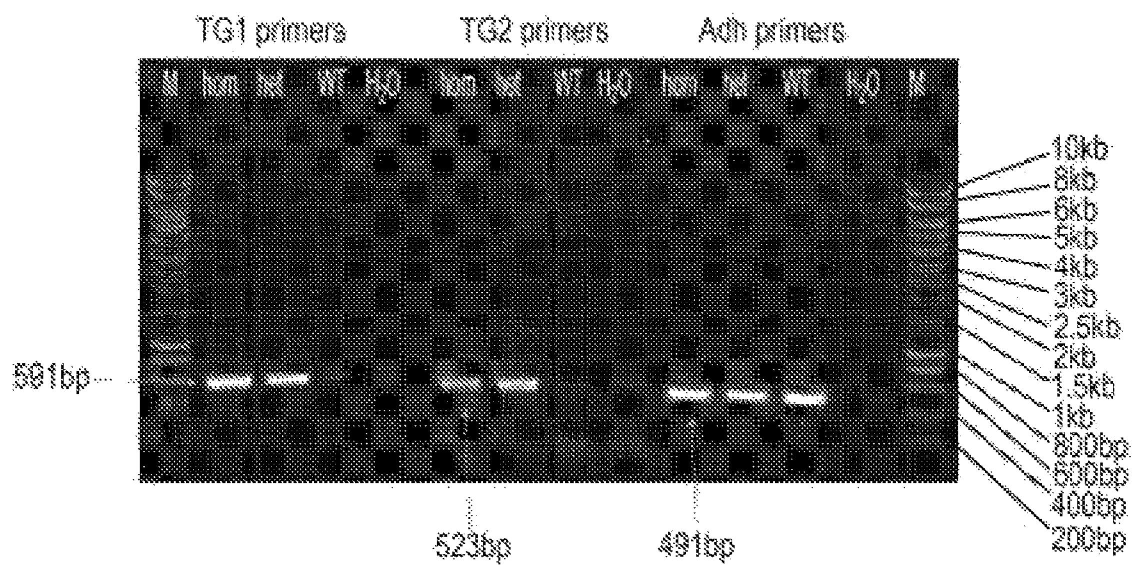
FIG. 5 is a photograph of a gel from a PCR-based assay for specific identification of OX3864A. The gel shows OX3864 homozygous, OX3864 heterozygous, wild-type individuals and a water negative control amplified with OX3864-specific primers, TG1 and TG2, along with Adh primers. Marker (M)=Smart ladder (Eurogentec).

Results from the PCR-based assay are shown in FIG. 5. OX3864 samples showed the expected 591 bp and 523 bp bands, for TG1 and TG2 respectively, whereas WT and water samples were negative. All genomic DNA samples showed the expected 491 bp product with Adh primers, showing that the genomic DNA was of sufficient quality for PCR amplification.

TAQMAN Assay for Specifically Detecting the Junction of the Integrated Transgene and Flanking Sequence This assay was developed to detect the sequence at the junction of the integrated transgene and *Ceratitis capitata* gDNA, which present a unique fingerprint for OX3864. This assay was developed to detect one junction using three specific oligonucleotides (Table 4). Two of the primers allow for the amplification of a 98 bp (52 bp flanking gDNA+46 bp transgene) fragment to which a third, dual-labelled [5' reporter (FAM)-3' quencher (BHQ1)] oligonucleotide, the probe, anneals. The probe specifically bridges the junction of the integration and flanking DNA in the amplified PCR product, requiring this boundary for a positive output. At each step of PCR-amplification, the 5'-3' exonuclease activity of Taq polymerase releases the 5' fluorescent reporter (FAM) from the annealed probe, resulting in an accumulative emission that is detectable in a real time PCR machine in samples bearing OX3864 DNA. The primer and probes used in this assay are shown on Table 4.

quality of the DNA samples analysed. A positive control of 9 wild-type pupae spiked with 1 heterozygous pupa was included, along with a negative control of water. PCR products were run on a 1% agarose gel with a smart ladder (Eurogentec, band sizes top to bottom: 10 kb, 8 kb, 6 kb, 5 kb, 4 kb, 3 kb, 2.5 kb, 2 kb, 1.5 kb, 1 kb, 800 bp, 600 bp, 400 bp, 200 bp).

Example 3: Field Testing of Strain OX3864A

Mating Competition with Wild Medflies from the Mediterranean Region

Competitive mating tests of the strains against wt males for wt females were carried out according to FAO/IAEA/USDA guidelines (FAO/IAEA/USDA, 2003). To test the ability of males to induce refractoriness to re-mating in females, the mated females were separated into two groups of 40 based on their initial mating choice (wt or Oxitec male) then re-exposed them to equal numbers of wt and Oxitec males on the following day. This process was run for 3 days, with cages scored for matings for 9 hours daily. Mating pairs were removed during mating as described above and the males were again genotyped by screening fluorescence. For mating competitiveness tests with wild-derived flies, pupae were recovered from infested oranges gathered from insecticide-free orange orchards in Heraklion province, Crete. Wild-derived adults were separated by sex immediately after eclosion. Wild-derived flies were left at 25° C., 50% relative humidity (R.H.) for 10-13 days to reach sexual maturity. All flies were allowed to adjust to natural light and temperature conditions of the glasshouse for a minimum of 24 hours prior to the start of the experiment. Each experiment began one hour after sunrise and lasted for a minimum of 9 hours. Mating tests were performed in green-house facilities at the University of Crete. OX3864A mating competition tests were performed in 7 replicates with 89 pairs assessed.

TABLE 4

| | |
|---|---|
| Cc3864FRTtaqF flanking specific primer | 5'-CAGGCAATCTGCTCCATTAAC-3' (SEQ ID NO: 10) |
| Cc3864FRTtaqR transgene specific primer | 5'-GACCTAGTCCCAAAGATTTCG-3' (SEQ ID NO: 11) |
| Cc3864FRTprobe OX3864-fla probe | 5' FAM-AGTGCTTACATTCATTTTAA GAGCACCTCAT-BHQ1-3' (SEQ ID NO: 12) |

Plasmid Backbone Analysis on Strain OX3864A

Figure 6:
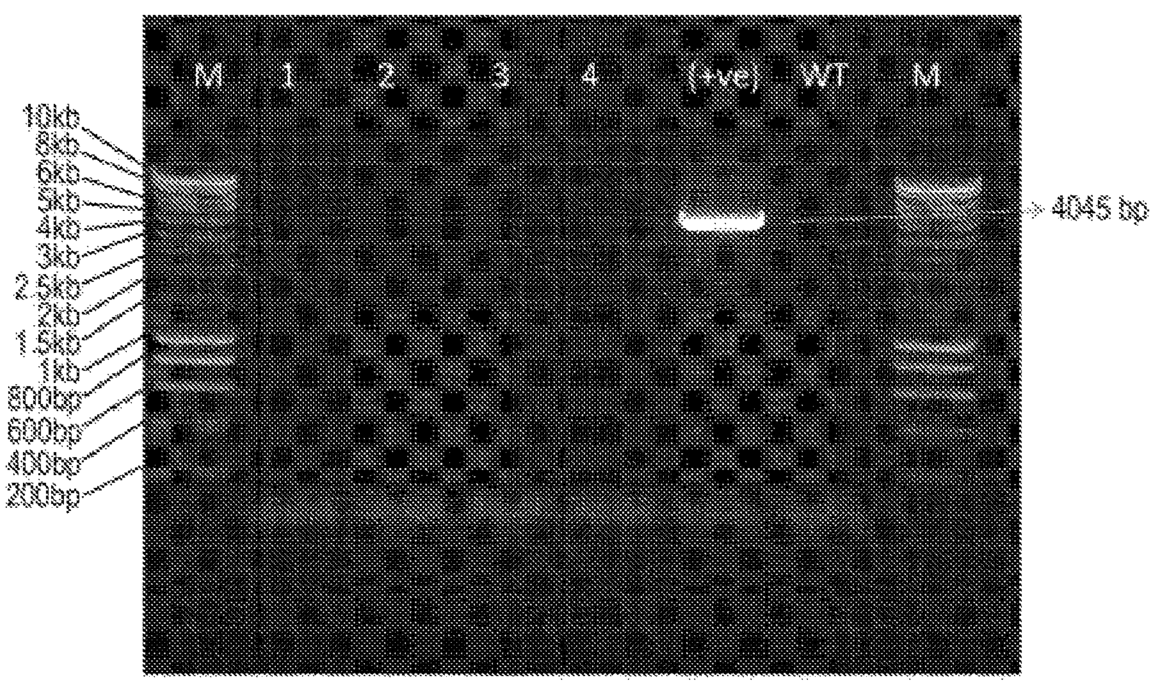
FIG. 6 is a photograph of a gel from PCR-based analysis for the detection of plasmid backbone in OX3864A fly samples. Lanes 1-4: OX3864A homozygous fly samples; Lane 5: positive control—transformed insect in which the plasmid backbone has inserted; lane 6: WT—Medfly wild-type gDNA.

The presence of plasmid backbone in the genome of this strain was verified by PCR utilising primers annealing to the piggyBac elements: PB5out (CTCTGGACGTCATCTTCACTTACGTG) (SEQ ID NO: 13) and PB3out (CTCGATATACAGACCGATAAAACACATGC) (SEQ ID NO: 14), which give a 4045 bp fragment if the plasmid backbone is present. Results are shown in FIG. 6. The complete absence of any plasmid backbone sequence was confirmed in all fly sample tested.

Silent Transgene Insertion(s) in Strain OX3864A

The possibility of silent insertions in this strain was investigated by PCR analysis. Wild-type males were crossed with OX3864A heterozygote females, and vice versa at a ratio of 1:3 (male:female). The next generation were reared to pupae and screened for fluorescence. 1000 non-fluorescent individuals were kept at −20 and analysed by PCR.

Figure 7:
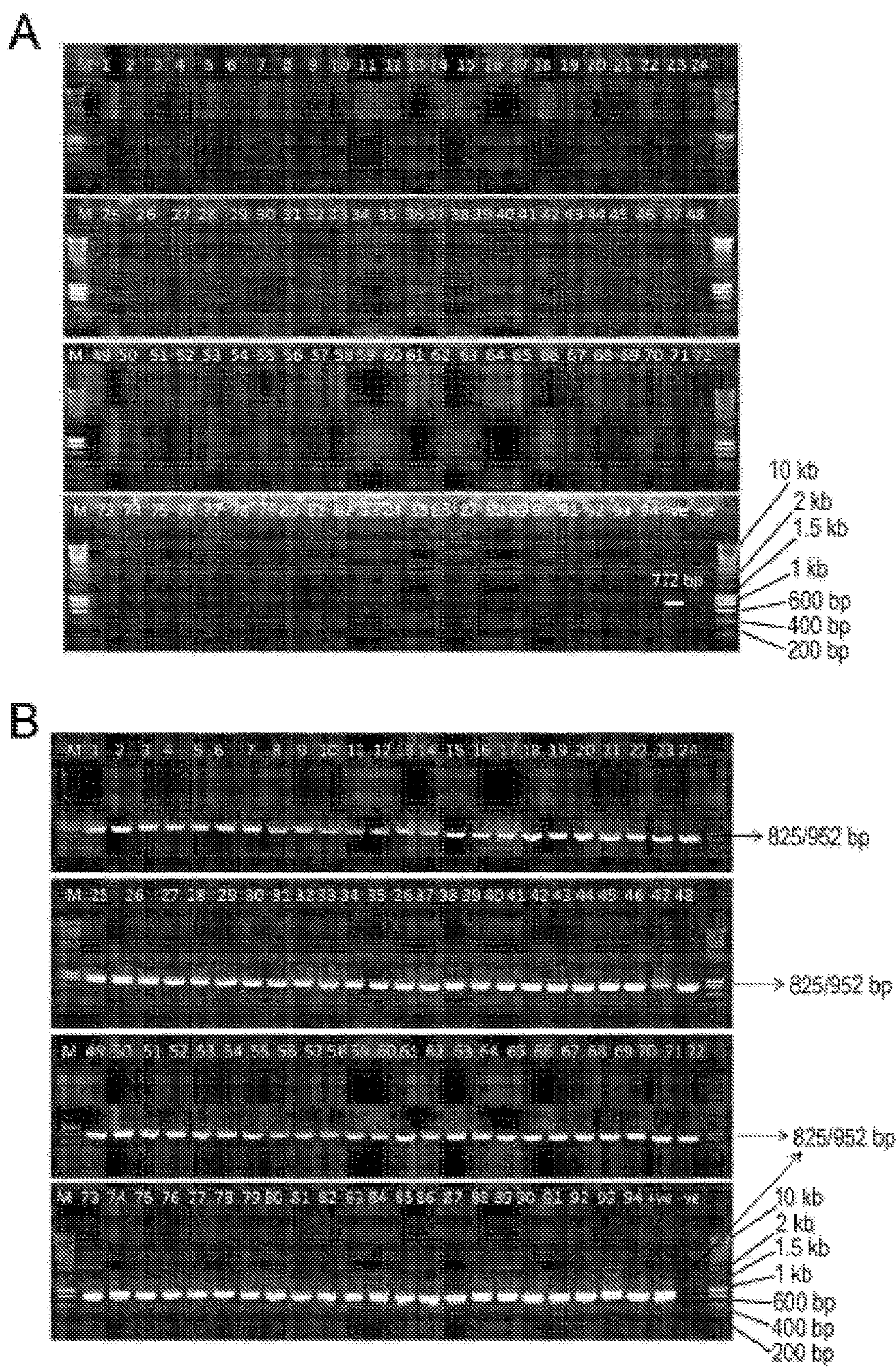
FIG. 7 shows photographs of gels from PCR analysis for detection of silent insertions in OX3864A flies. Positive control: nine wild-type pupae spiked with one heterozygous pupa; negative control: water. Panel A shows the detection of transgene sequences (772 bp) using primers TD539) Diag3K10 (CAACTCTTCTCGTTTTGAAGTCAGC; SEQ ID NO: 22) and 852) ttAVdiagF (CGTCAGGCAATCGAGCTGTTC; SEQ ID NO: 23). Panel B shows the detection of wild-type sequences (852/952 bp based on previously observed WT polymorphism) using primers 1351) Med3864altF (GGATACCGAATTCATAGCGGCG; SEQ ID NO: 24) and 1366) Med3864fldiagR2 (GGTGAGAAGCATCCATTCCAGGC; SEQ ID NO: 25). Marker (M): Smart ladder (Eurogentec).

Results are shown in FIG. 7. The use of primers for the amplification of wild-type sequences was to ensure the The mean RSI value of the OX3864A flies, when mating with wild-derived medfly from Crete, was 0.45±0.13 (t-test: $t12=-0.9$, $n=89$, $P=0.38$), which gave no evidence of a significant difference in mating competitiveness between OX3864A and wild-derived males.

Caged Suppression of Stable Wild-Type Populations

Stable populations of wt medfly were established in four large field cages with two cages chosen at random to be "treatment" cages into which, in addition to the normal number of pupae added to the cages, approximately 1500 RIDL males per week were released. This protocol was based on that of Wise de Valdez et al. The greenhouse-based field cages were 8 $m^3$ each and contained a 1.5 m tall lemon tree, and were housed at the University of Crete, Heraklion, utilising natural light and a stable temperature and humidity (c. 25° C., 50% R.H.,). Cages contained three food and water sources and two oviposition pots filled with deionised water (emptied daily), each with two 40 $cm^2$ egg laying surfaces.

Wt populations were established over an 8 week period by introducing a fixed number of pupae to each cage per week (200 in week 1, 300 in week 2, 180 in week 3 and 230 thereafter weeks 4-8). Pupal additions for the first 4 weeks originated from a wt stock colony; thereafter all pupal additions were from eggs caught in the oviposition pots, and reared in the laboratory at low density (1 larva/0.5 g medium) before re-introduction to field cages as pupae. Egg numbers were counted daily from the oviposition pots, while adult numbers were calculated weekly.

Figure 8:
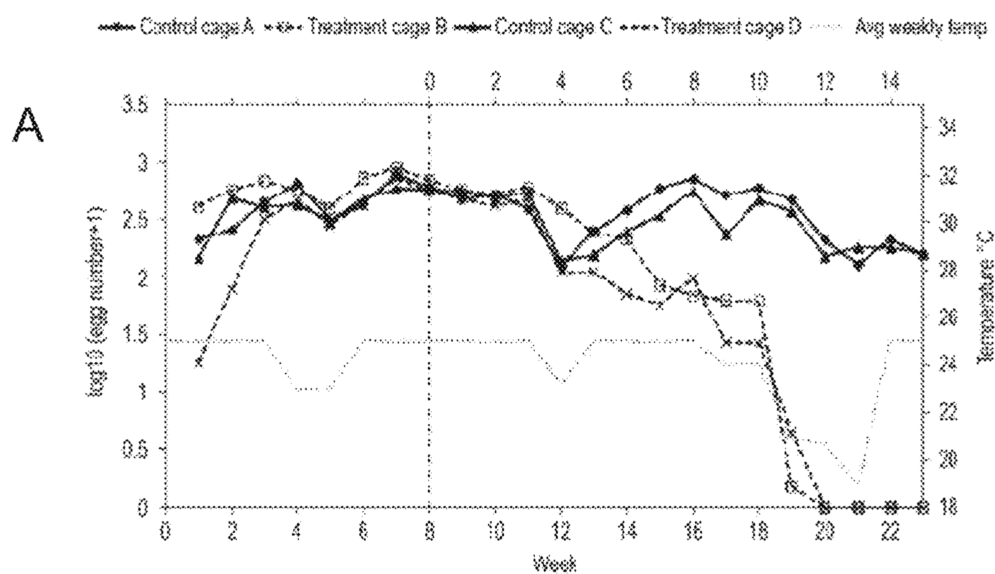
FIG. 8 shows graphs of the changing Medfly population dynamics through introduction of OX3864A males. Panel A is a graph showing average daily egg production rates for each given week in treatment and control cages. The lowest line denotes the average weekly daytime temperature (centigrade), taken from daily midday temperature readings. Panel B shows calculated numbers of females from treatment and control cages. Panel C shows the proportion of progeny returned to each of the treatment cages from the oviposition traps displaying the DsRed2 fluorescent phenotype.
Figure 8:
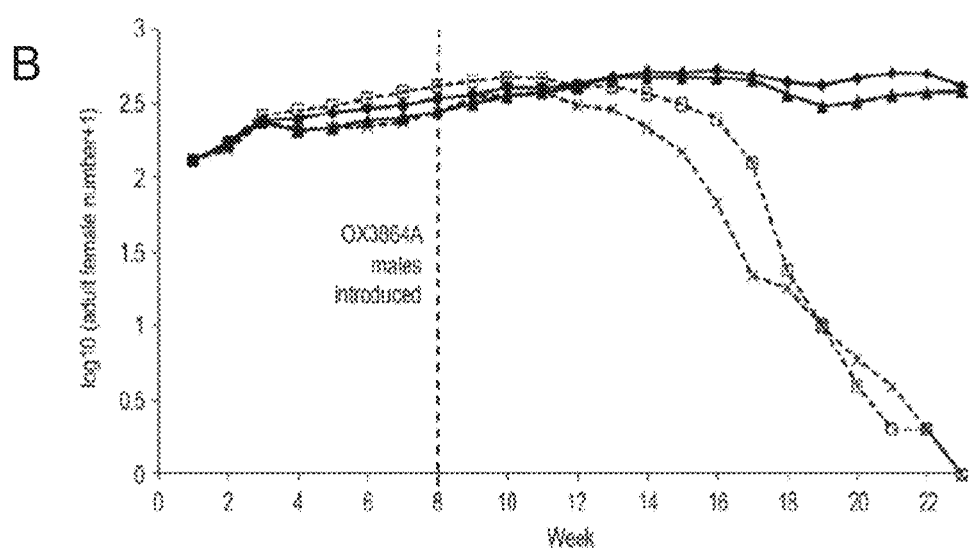
Figure 8:
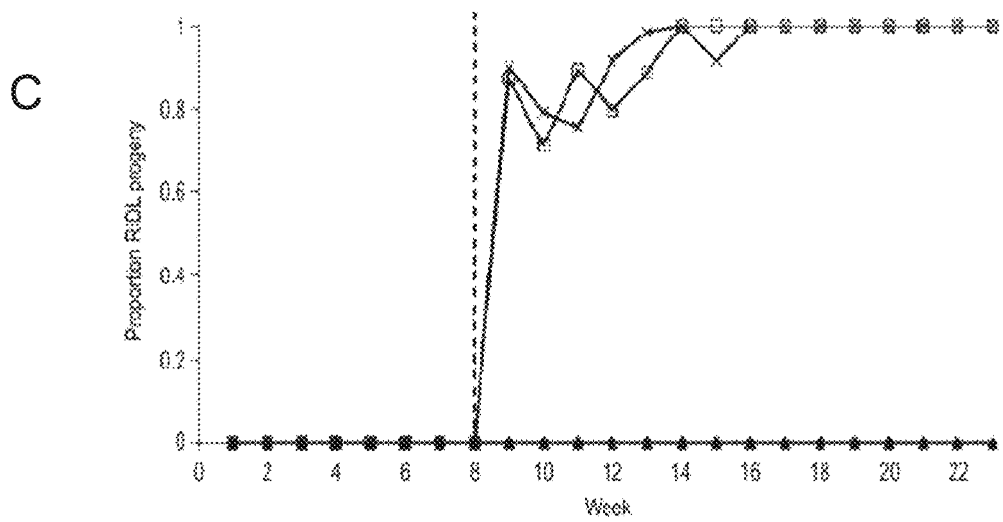

At week 7, cages were randomly divided into treatment or control. From week 8 onwards, RIDL treatment cages received weekly additions of 1700 OX3864A pupae reared off-tet (resulting in the addition of approximately 1,500 adult males per week). This gave an initial ratio of .about.7 OX3864A males to 1 wt male in week 8, based on estimates of cage populations (1500 males released into cages with an approximate population of 220 wt males) and a weekly recruitment ratio of roughly 15:1 (OX3864A to wt males). Once OX3864A introductions began, the pupal return to a treatment cage was made proportional to its rate of pupae production, with the control cages providing a stable weekly pupal return coefficient for this calculation. For example, in week 16 the mean number of pupae recovered from the control cages was 300. Because returns to the control cages were set at a constant 230 per week, the number of pupae to return to all cages, out of all of those which developed is set by a coefficient of (230/300=0.76). For example in the same week one of the treatment cages produced a total of 126 pupae. The number of pupae which were returned to this cage (using the coefficient), was therefore 96 (126×0.76). This methodology allowed for a dynamic pupal return that was dependent on egg production and pupal survival, and reflects the number of eggs laid and the action of RIDL on female larval survival. Results are shown in FIG. 8.

Dramatic decreases in weekly egg production were observed by 7 weeks post-RIDL release (PR) in treatment cages, compared with a continued stable rate of egg production in control cages, and continued until eventual extinction of the wild-type population in both treatment cages (as assessed by two weeks of no egg production) by week 22 (FIG. 8A). This was due to the proportion of returned progeny carrying the OX3864A transgene increasing in treatment cages, resulting in a rapid decline in the female population (FIG. 8B). Transgene frequency in the treatment cage populations was monitored by screening the returning pupae (chosen from all the pupae produced at random) for the presence of the DsRed2 fluorescent marker. The frequency of the transgene in the returning progeny of the treatment cages was at 100% by week 8 PR (FIG. 8C), with both cages considered extinct by week 14 PR (extinction defined as zero egg production for two consecutive weeks).

Example 4: Protocol for Detection of OX3864 Transgene

This assay was used to detect the presence or absence of the OX3864 transgene in a variety of OX3864 insect samples (field, mass-rearing and laboratory). The same protocol can also be used to provide evidence of stability of the OX3864 transgene over time. Successful amplification of the OX3864 transgene over time provides evidence of its stability, as one primer anneals to the transgene, the other to the flanking genomic sequence, so mobilisation of the transgene results in a negative PCR.

a. Materials

Purelink genomic extraction kit (supplied by Invitrogen)
BioTaq DNA Polymerase (PCR Biosystems)
Primers—described in section C (synthesized by Life Technologies)
10× Bovine serum albumin (BSA, New England Biolabs)
Smart Ladder 200 bp-10 kb (Eurogentec)
Milli-Q de-ionised pure water
Agarose (Web Scientific)
Tris-acetate-EDTA solution (10×TAE)
Ethidium Bromide
6× gel loading solution (comprising 30% glycerol, 0.25% bromophenol blue)

b. Equipment

Biometra Thermocyclers (T3000)
Gilson pipettes,
Pipette tips,
96-well micro-titre plates or 0.2 ml PCR tubes, adhesive plate lids or 8 well strip lids,
2 ml microfuge tubes,
Gel electrophoresis tank, Power pack, cast and combs.
Ultra-violet (UV) visualisation system.

c. Methods i. Extraction of Genomic DNA

Genomic DNA was isolated from individual insects using the protocol below (also found in TD/SOP/00142) using the Invitrogen Purelink genomic extraction kit.

1. Add 96-100% ethanol to PureLink™ Genomic Wash Buffer 1 and PureLink™ Genomic Wash Buffer 2 according to Instructions on each label. Mix well. Mark on the labels that ethanol is added. Store both wash buffers with ethanol at room temperature.
2. Set a water bath or heat block at 55° C.
3. Add 180 μl PureLink™ Genomic Digestion Buffer and 20 μl Proteinase K to each pool of abdomens. Break the insect samples up with a sterile pestle. After use, put the pestles in a beaker of Virkon for at least 24 hours before washing and autoclaving. Ensure the tissue is completely immersed in the buffer mix.
4. Incubate at 55° C. with occasional vortexing until lysis is complete (1-4 hours). You may perform overnight digestion.
5. To remove any particulate materials, centrifuge the lysate at maximum speed for 3 minutes at room temperature. Transfer supernatant to a new microcentrifuge tube.
6. Add 20 μl RNase A to lysate, mix well by briefly vortexing, and incubate at room temperature for 2 minutes.
7. Add 200 μl PureLink™ Genomic Lysis/Binding Buffer and mix well by vortexing to yield a homogenous solution.
8. Add 200 μl 96-100% ethanol to the lysate. Mix well by vortexing to yield a homogenous solution. The Lysis/binding buffer and 100% Ethanol can be mixed before adding.
9. Remove a PureLink™ Spin Column in a Collection Tube from the kit. Add the lysate (.about.640 μl) prepared with PureLink™ Genomic Lysis/Binding Buffer and ethanol to the spin column.
10. Centrifuge the column at 10,000×g for 1 minute at room temperature. Discard the collection tube and place the spin column into a clean PureLink™ Collection Tube supplied with the kit.
11. Add 500 μl Wash Buffer 1 prepared with ethanol to the column. Centrifuge column at 10,000×g for 1 minute at room temperature. Discard the collection tube and place the spin column into a clean PureLink™ collection tube supplied with the kit.

12. Add 500 μl Wash Buffer 2 prepared with ethanol to the column. Centrifuge the column at maximum speed for 3 minutes at room temperature. Discard flow through and re-spin for a further minute at 10,000×g.
13. Place the spin column in a sterile 1.5-ml microcentrifuge tube. Add 100 μl of PureLink™ Genomic Elution Buffer to the column.
14. Incubate at room temperature for 1 minute. Centrifuge the column at maximum speed for 1 minute at room temperature.
15. Remove and discard the column. Use DNA for the desired downstream application or store the purified DNA at 4° C. (short-term) or −20° C. (long-term).
16. Record all details in lab book.

ii. PCR Protocol

Primers are from the Oxitec catalogue; numbers refer to Oxitec internal primer catalogue and are synthesised off site by Life Technologies Transgene specific and Actin 4 endogenous gene sequences were amplified by PCR using PCR BIO polymerase as follows:

OX3864 Transgene Primers:

1087)FRTNheF (GGTGTGGCTAGCTCGAAGAAGTTCCTATTCCGAAGTTCC; SEQ ID NO: 7) and 1272) 3864FRTFIF (CAACGAGTGACAGCAATGATATTCCTTAC; SEQ ID NO: 6) produces a product of 532 bp. FRTNheF anneals to the transgene, whereas 3864FRTFIF anneals to the genomic sequence flanking the transgene. This primer set will only amplify samples containing the OX3864 transgene.

Adh Control Primers:

A primer set was included to check amplification of *Ceratitis capitata* genomic DNA, as an internal control. The primers are 1131)CcAdh2RTF (GAAAGCTGTTCGGGCTTCAGGC; SEQ ID NO: 8) and 1132)CcAdh2RTR (CTTGGAGGTGATGTCGAATTTGGTG; SEQ ID NO: 9) producing a 491 bp product.

PCR master mix was prepared (enough for the number of samples plus 1-5 extras, to allow for pipetting error), by adding the following ingredients to a microfuge tube, in the order they appear below:

| | x (n + 1) |
|---|---|
| $H_2O$ | 12.3 μl |
| Biotaq buffer | 4 μl |
| 10x BSA | 0.5 μl |
| Primer 1087 or 1131 | 0.5 μl |
| Primer 1272 or 1132 | 0.5 μl |
| Biotaq polymerase | 0.2 μl |

18 μl master mix was pipetted into each PCR tube or well of the 96 well plate.

2 μl gDNA template was added.

Templates include a known positive control of OX3864 homozygous gDNA sample (from the mass-rearing stock, or previously shown to be positive) a negative control of a wild type gDNA sample and milli-Q water negative control.

PCRs were run on a Biometra T3000 thermocycler using the following program:

1. 94° C. 2 min
2. 94° C. 15 s
3. 60° C. 30 s (reduce temperature by 0.5° C. each cycle)
4. 72° C. 15 s Go to step 2×10 cycles
5. 94° C. 15 s
6. 55° C. 30 s
7. 72° C. 15 s Go to step 5×25 cycles 8. 72° C. 7 mins 9. 4.° C. hold. 8 μl of the PCR product is mixed with 1.5 μl gel loading buffer (30% glycerol with 0.25% bromophenol blue) and run on a 1% agarose gel (see below) at 120V for 25 minutes for visualisation. The Eurogentec Smart Ladder is loaded at each end of the gel. Gels are visualised and photographed using a Uvitec gel visualisation system.

iii. Agarose Gel Preparation 1 g agarose mixed with 100 ml 1×TAE buffer, dissolved by microwaving for about 2 minutes, cooled under cold running water for 30 seconds, 1.5 μl 1% Ethidium Bromide was added, then poured into a cast and allowed to set.

REFERENCES

Caceres, C. (2002). "Mass rearing of temperature sensitive genetic sexing strains in the Mediterranean fruit fly (*Ceratitis capitata*)". Genetica, 116: 107-116.

Cande C, Cecconi F, Dessen P, Kroemer G. (2002). "Apoptosis-inducing factor (AIF): key to the conserved caspase-independent pathways of cell death?". J Cell Sci., 115 (24):4727-34.

Cayol J. P., et al. 2002. "Recent findings on Medfly sexual behaviour: Implications for SIT". Florida Entomologist, 85(1): 171-181.

Choi J. and Guarino A. (1995). "The Baculovirus Transactivator IE1 Binds to Viral Enhancer Elements in the Absence of Insect Cell Factors". Journal of Virology, 69(7): 4548-4551.

Dafa'alla T. H., Condon G. C., Condon K. C., Phillips C. E., Morrison N. I., Jin L., Epton M. J., Fu G. L., Alphey L. (2006). "Transposon-free insertions for insect genetic engineering". Nat Biotechnol, 24(7), 820-821. (doi: 10.1038/nbt1221).

FAO/IAEA/USDA. 2003 Product quality control and shipping procedures for sterile mass-reared tephritid fruit flies. Vienna, Austria: International Atomic Energy Agency IAEA.

Fu G. L., Condon K. C., Epton M. J., Gong P., Jin L., Condon G. C., Morrison N. I., Dafa'alla T. H., Alphey L. (2007). "Female-specific insect lethality engineered using alternative splicing. Nat Biotechnol, 25(3), 353-357. (doi: 10.1038/nbt1283).

Gong P., Epton M. J., Fu G. L., Scaife S., Hiscox A., Condon K. C., Condon G. C., Morrison N. I., Kelly D. W., Dafa'alla T., et al. (2005). "A dominant lethal genetic system for autocidal control of the Mediterranean fruitfly". Nat Biotechnol, 23(4), 453-456.

Handler A. M. and Harrel R. A. (2001) "Polyubiquitin-Regulated DsRed Marker for Transgenic Insects". Biotechniques 31, 820-828

Harris A. F., Nimmo D., McKemey A. R., Kelly N., Scaife S., Donnelly C. A., Beech C., Petrie W. D. & Alphey L. (2011). "Field performance of engineered male mosquitoes". Nature Biotechnology 29(11): 1034-1037

Horn C, Wimmer EA. (2003). "A transgene-based, embryo-specific lethality system for insect pest management". Nat Biotechnol., 21(1):64-70.

Huang, Q., Deveraux, Q. L., Maeda, S., Salvesen, G. S., Stennicke, H. R., Hammock, B. D. and Reed, J. C. (2002). "Evolutionary conservation of apoptosis mechanisms: Lepidopteran and baculoviral inhibitor of apoptosis proteins are inhibitor of mammalian caspase-9". Agricultural Sciences 97(4):1427-1432.

McInnis, D. O., Rendon P., Komatsu J. (2002) Mating and remating of medflies (Diptera: Tephritidae) in Guatemala: individual fly marking in field cages". Florida Entomologist 85(1): 126-137

Mumford, J. (2012). "Science, Regulation, and Precedent for Genetically Modified Insects". PLoS Negl Trop Dis, 6(1).

Olson, M. R., Holley, C. L., Gan, E. C., Colon-Ramos, D. A., Kaplan, B. and Kornbluth, S. (2003). "A GH3-like domain in reaper is required for mitochondrial localization and induction of IAP degradation". J. Biol. Chem., 278(45):44758-44768.

Pane, A., Salvemini, M., Delli Bovi, P., Polito, C., and Saccone, G. (2002). "The transformer gene in *Ceratitis capitata* provides a genetic basis for selecting and remembering the sexual fate". Development, 129, 3715-3725.

Simmons G. S., McKemey A. R., Morrison N. I., O'Connell S., Tabashnik B. T., Claus J., Fu G., Tang G., Sledge M., Walker A. S., Phillips C. E., D. Miller, Rose R. I., Staten R. T., Donnelly C. A., Alphey L. (2011) Field Performance of a Genetically Engineered Strain of Pink Bollworm PLoS ONE 6(9): e24110

Valdez de M. R. W., Nimmo D., Betz J., Gong H. F., James A. A., Alphey L., Black W. C. (2011). "Genetic elimination of dengue vector mosquitoes". Proc Natl Acad Sci USA 108(12), 4772-4775.

Vernooy, S. Y., Copeland, J., Ghaboosi, N., Griffin, E. E., Yoo, S. J. and Hay, B. A. (2000). J. Cell Biol. 150(2): F69-F75.

White, K., Tahoaglu, E. and Steller, H. (1996). "Cell killing by the *Drosophila* gene reaper". Science, 271 (5250): 805-807.

Wing, J. P., Zhou, L., Schwartz, L. M. and Nambu, J. R. (2001). "Distinct cell killing properties of the *Drosophila* reaper, head involution defective, and grim genes". Cell Death Diffn 5(11): 930-939.

The invention claimed is:

1. An isolated polynucleotide construct, wherein said polynucleotide construct comprises a first and a second gene expression system forming a first and second positive feedback loop to be expressed in an insect:

i) the first gene expression system comprises the following components: a first dominant lethal gene operably linked to a first promoter, a gene encoding a first activating transcription factor, and a first splice control sequence, ii) the second gene expression system comprises the following components: a second dominant lethal gene operably linked to a second promoter, a gene encoding a second activating transcription factor, and a second splice control sequence, wherein:

each of said activating transcription factors is capable of activating at least one of said promoters, and both of said promoters are activated when both of said transcription factors are expressed, each of the first and second splice control sequences mediates female-specific expression of the first and second dominant lethal genes in female insects, respectively, by alternative splicing, and such expression leads to the death of said female insects at an early stage of development, the transactivation activity of each of the first and second activating transcription factors is repressible by a first and a second exogenous control factor, respectively, wherein said first exogenous control factor is the same as or different from said second exogenous control factor, and each of said components of said first gene expression system are the same as or different from said components of said second gene expression system;

wherein one of the first and second gene expression systems comprises a VP16 encoding sequence and a third promoter operably linked to the VP16 sequence, wherein the activating transcription factor capable of activating the first or second promoter of said gene expression system is also capable of activating the third promoter, wherein:

the first dominant lethal gene is tTAV (SEQ ID NO: 26), the first activating transcription factor is the tTAV gene product, the first promoter is Hsp70, the first splice control sequence is Cctra, the second dominant lethal gene is tTAV3 (SEQ ID NO: 28), the second activating transcription factor is the tTAV3 gene product, the second promoter is srya, and the second splice control sequence is Bztra, the first gene expression system further comprises a first enhancer associated with the first promoter, wherein the first enhancer is tetOx7, the second gene expression system further comprises a second enhancer associated with the second promoter, wherein the second enhancer is tetOx14, the polynucleotide construct further comprises a third dominant lethal gene operably linked to a third promoter, the third promoter being associated with the second enhancer, wherein the third dominant lethal gene is VP16 and the third promoter is Hsp70, wherein the second promoter is associated with one end of the second enhancer and the third promoter is associated with the other end of the second enhancer, and the polynucleotide construct further comprises a first genetic marker, which is DsRed2.

2. A polynucleotide comprising a first and a second gene expression system to be expressed in an insect, wherein:

i) the first gene expression system comprises the following components: a first dominant lethal gene operably linked to a first promoter, a gene encoding a first activating transcription factor, and a first splice control sequence, and ii) the second gene expression system comprises the following components: a second dominant lethal gene operably linked to a second promoter, a gene encoding a second activating transcription factor, and a second splice control sequence, wherein:

each of said activating transcription factors is capable of activating at least one of said promoters, and both of said promoters are activated when both of said transcription factors are expressed, each of the first and second splice control sequences mediates female-specific expression of the first and second dominant lethal genes in insects, respectively, by alternative splicing, the transactivation activity of each of the first and second activating transcription factors is repressible by a first and a second exogenous control factor, respectively, wherein said first exogenous control factor is the same as or different from said second exogenous control factor, each of said components of said first gene expression system are the same as or different from said components of said second gene expression system, and the polynucleotide comprises the nucleotide sequence of SEQ ID NO: 1.

3. The polynucleotide of claim 2, wherein the insect comprises the nucleotide sequence of SEQ ID NO: 2.

4. The polynucleotide of claim 2, wherein the insect comprises the nucleotide sequence of SEQ ID NO: 3.

* * * * *